(12) United States Patent
Mostoslavsky et al.

(10) Patent No.: US 8,865,467 B2
(45) Date of Patent: Oct. 21, 2014

(54) SINGLE LENTIVIRAL VECTOR SYSTEM FOR INDUCED PLURIPOTENT (IPS) STEM CELLS DERIVATION

(75) Inventors: Gustavo Mostoslavsky, West Roxbury, MA (US); Cesar A. Sommer, Jamaica Plain, MA (US)

(73) Assignee: Boston Medical Center Corporation, Boston, MA (US)

( * ) Notice: Subject to any disclaimer, the term of this patent is extended or adjusted under 35 U.S.C. 154(b) by 442 days.

(21) Appl. No.: 13/080,728

(22) Filed: Apr. 6, 2011

(65) Prior Publication Data

US 2011/0236966 A1    Sep. 29, 2011

Related U.S. Application Data

(63) Continuation of application No. PCT/US2009/059660, filed on Oct. 6, 2009.

(60) Provisional application No. 61/103,091, filed on Oct. 6, 2008.

(51) Int. Cl.
*C12N 15/00* (2006.01)
*A01N 63/00* (2006.01)

(52) U.S. Cl.
USPC .......................................... 435/455; 424/93.1

(58) Field of Classification Search
USPC .......................................... 424/93.1; 435/455
See application file for complete search history.

(56) References Cited

U.S. PATENT DOCUMENTS

2006/0263882 A1    11/2006    Fazio et al.

FOREIGN PATENT DOCUMENTS

WO    03/072797    4/2003
WO    2009/115295    9/2009

OTHER PUBLICATIONS

Szymczak (Nature Biotech., May 2004, vol. 22, No. 5, p. 589-594).*
Moore (2002, DNA and Cell Biol., vol. 21(5/6), pp. 443-451).*
Thomson (1995, PNAS, vol. 92, pp. 7844-7848).*
Takahashi (Cell, 2006, vol. 126:663-676).*
Yu (Science, Nov. 20, 2007, vol. 318, p. 1917-1920).*
Nakagawa (Nat Biotechnol, 2008, vol. 26: 101-106).*
Shao (Cell Res., Mar. 2009, vol. 19, No. 3, p. 296-306).*
Kaji (Nature, Apr. 9, 2009, vol. 458, p. 771-776).*
Ellis, J. and Hotta, A., SickKids The Hospital for Sick Children, Oct. 29, 2008. "EOS vectors select for pluripotency during iPS cell reprogramming (RDLP# 605)."
Stadtfeld et al., Science, 945-949 (2008). "Induced pluripotent stem cells generated without viral integration."
Takahashi, K. and Yamanaka, S., Cell, 126, 663-676 (2006). "Induction of pluripotent stem cells from mouse embryonic and adult fibroblast cultures by defined factors."
Tsai, S. et al., 6th Annual International Society for Stem Cell Research, Philadelphia, PA, 2008. "Development of reagents for generation of induced pluripotent stem (iPS) cells in swine."
Azzouz et al., The Journal of Neuroscience, 22(23):10302-10312 (2002). "Multicistronic lentiviral vector-mediated striatal gene transfer of aromatic L-amino acid decarboxylase, tyrosine hydroxylase, and GTP cyclohydrolase I induces sustained transgene expression, dopamine production, and functional improvement in a rat model of Parkinson's disease."
De Felipe and Izquierdo, Human Gene Therapy, 11(13):1921-1931 (2000). "Tricistronic and tetracistronic retroviral vectors for gene transfer."
Fussenegger et al., Cytotechnology, 28(1-3):229-35 (1998). "pQuattro vectors allow one-step multigene metabolic engineering and autoselection of quattrocistronic artificial mammalian operons."
Gascon et al., Journal of Neuroscience Methods, 168:104-112 (2007). "Dual-promoter lentiviral vectors for constitutive and regulated gene expression in neurons."
Hasegawaa et al., Stem Cells, 25:1707-1712 (2007). "Efficient multicistronic expression of a transgene in human embryonic stem cells."
Brambrink et al., Cell Stem Cell, 2(2):151-159 (2008). "Sequential expression of pluripotency markers during direct reprogramming of mouse somatic cells."
Carey et al., PNAS USA, 106(1):157-162 (2009). "Reprogramming of murine and human stomatic cells using a single polycistronic vector."
Chang et al., Stem Cells, 27(5):1042-1049 (2009). "Polycistronic lentiviral vector for hit and run reprogramming of adult skin fibroblasts to induced pluripotent stem cells."
Chinnasamy et al., Virology Journal, 3:14 (2006). "Multicistronic lentiviral vectors containing the FMDV 2A cleavage factor demonstrate robust expression of encoded genes at limiting MOI."
Gonzalez et al., PNAS USA, 106(22):8918-8922 (2009). "Generation of mouse-induced pluripotent stem cells by transient expression of a single nonviral polycistronic vector."
Lowry et al., PNAS USA, 105(8):2883-2888 (2008). "Generation of human induced pluripotent stem cells from dermal fibroblasts."
Okita et al., Science, 322(5903):949-953 (2008). "Generation of mouse induced pluripotent stem cells without viral vectors."
Papapetrou et al., PNAS USA, 106(31):12759-12764 (2009). "Stoichiometric and temporal requirements of Oct4, Sox2, Klf4, and c-Myc expression for efficient human iPSC induction and differentiation."
Pei, The Journal of Biological Chemistry, 284(6):3365-3369 (2008). "Regulation of pluripotency and reprogramming by transcription factors."

(Continued)

*Primary Examiner* — Michael C. Wilson
(74) *Attorney, Agent, or Firm* — Ronald I. Eisenstein; Nixon Peabody LLP

(57) ABSTRACT

The present invention is based on the discovery that a single lentiviral vector expressing multiple individual transcription factor proteins from a single multi-cistronic mRNA can reprogram a fibroblast cell to a stem cell-like cell. These reprogrammed induced pluripotent stem (iPS) cells are pluripotent. Additions of the Cre-LoxP sequences into the single lentiviral vector facilitate excision of the vector after reprogramming in achieved. Addition of a maker gene into the single lentiviral vector facilitates detection of the presence of the vector in an iPS. The invention provides compositions and methods of producing iPS cells using a single multi-cistronic lentiviral vector.

7 Claims, 22 Drawing Sheets

(56) References Cited

OTHER PUBLICATIONS

Shao et al., Cell Research, 19(3):296-306 (2009). "Generation of iPS cells using defined factors linked via the self-cleaving 2A sequences in a single open reading frame."

Sommer et al., Stem Cells, 27(3):543-549 (2009). "Induced pluripotent stem cell generation using a single lentiviral stem cell cassette."

Stadtfeld et al., Cell Stem Cell, 2(3):230-240 (2008). "Defining molecular cornerstones during fibroblast to iPS cell reprogramming in mouse."

Szymczak et al., Expert Opinion on Biological Therapy, 5(5):627-638 (2005). "Development of 2A peptide-based strategies in the design of multicistronic vectors."

Yu et al., Science, 318(5858):1917-1920 (2007). "Induced pluripotent stem cell lines derived from human somatic cells."

* cited by examiner

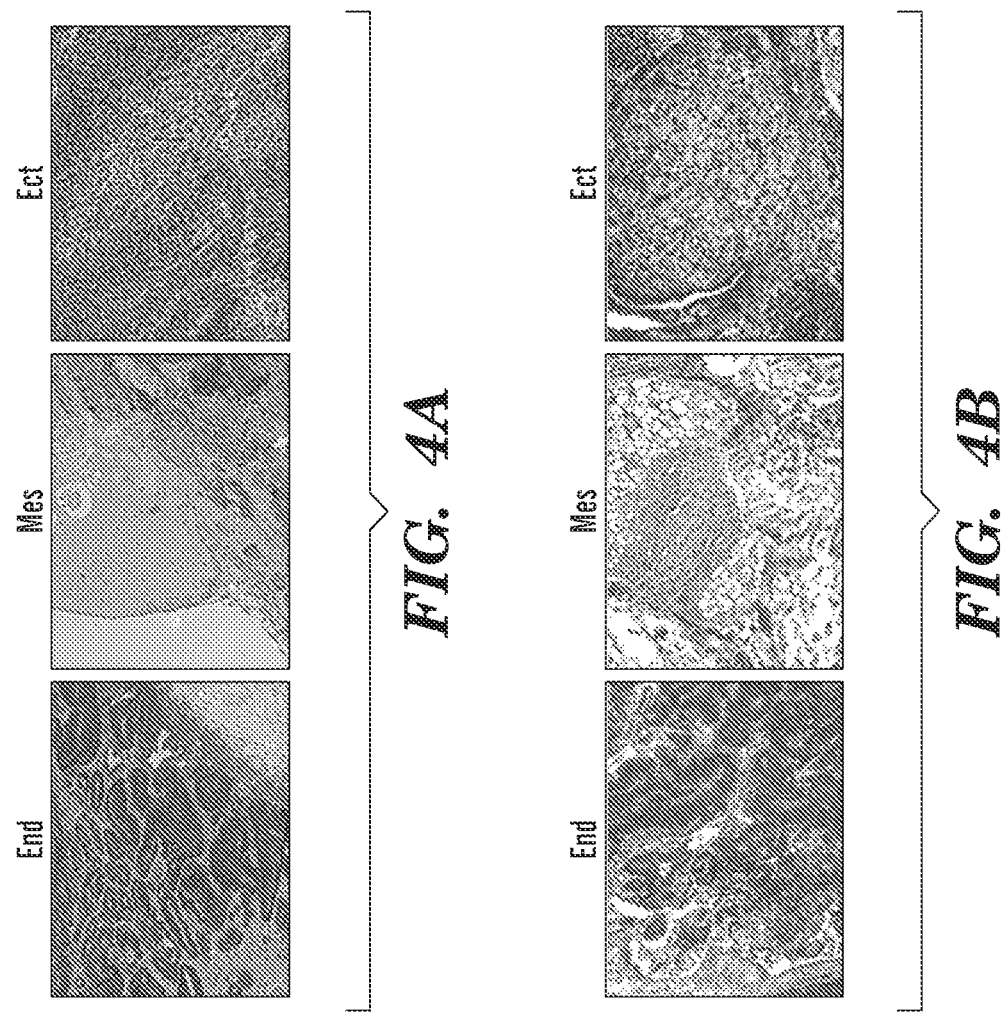

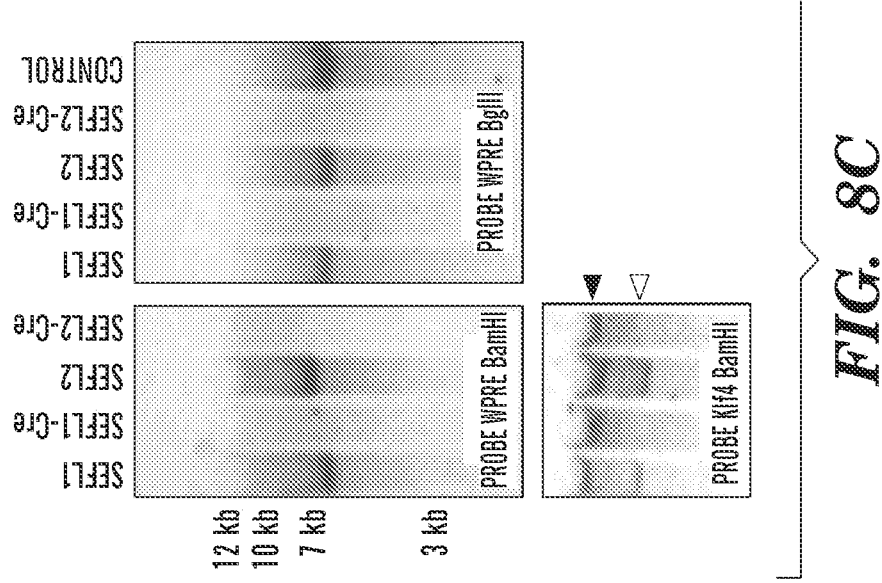
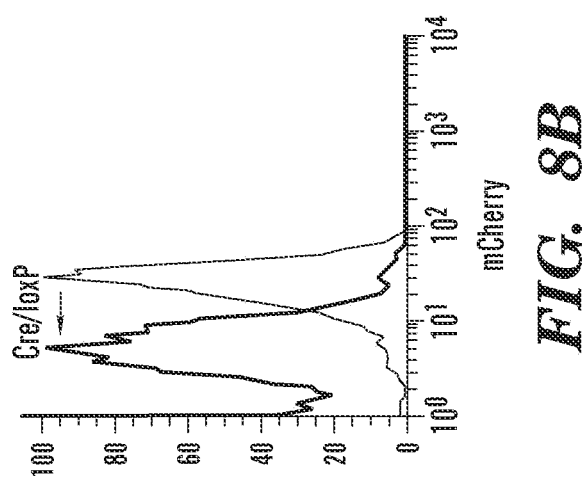
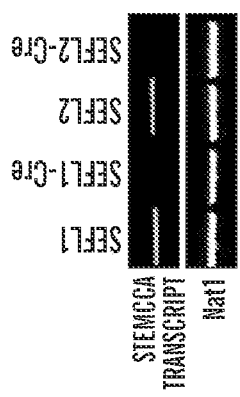

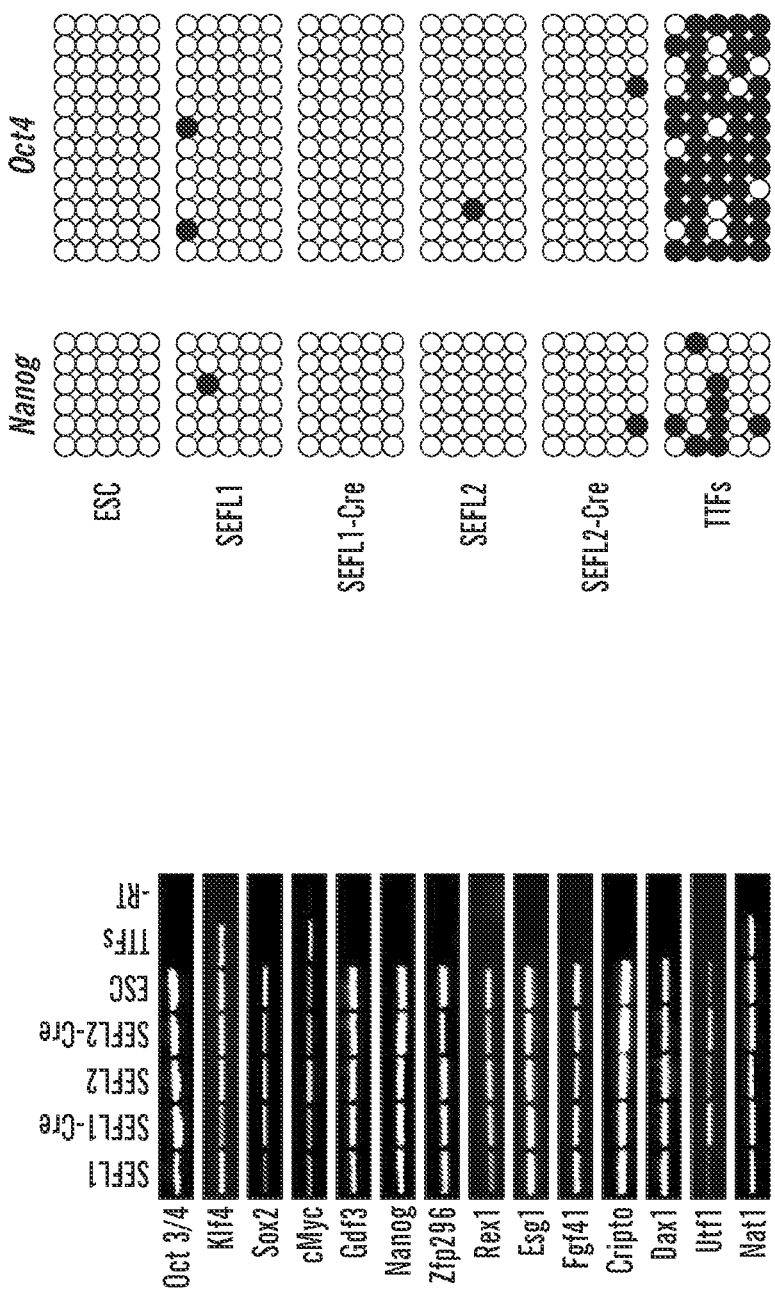

US 8,865,467 B2

SINGLE LENTIVIRAL VECTOR SYSTEM FOR INDUCED PLURIPOTENT (IPS) STEM CELLS DERIVATION

CROSS REFERENCE TO RELATED APPLICATIONS

This application is a continuation application of the International Application No. PCT/US2009/059660, filed Oct. 6, 2009, which designates the United States, which claims benefit under 35 U.S.C. §119(e) of the U.S. Provisional Application No. 61/103,091 filed on Oct. 6, 2008, the contents of which are incorporated herein by reference in their entirety.

BACKGROUND OF INVENTION

The capacity of embryonic stem cells (ESCs) to give rise to all types of somatic cells together with their ability to grow indefinitely in culture underscores their potential for in vivo therapeutic applications. However, many challenges exist, for example, ES cells are not genetically identical to the organism from which they are harvested, and thus rejection and immunogenicity are two concerns that potentially limit their future use in clinical transplantation. In addition, ethical concerns have been raised regarding the derivation of human ES cells from human embryos. For these reasons considerable effort has been invested in attempting to derive pluripotent stem cells from post-natal tissue that may be employed for isogenic or autologous transplantation. However, the generation of patient-specific autologous ESCs is technically challenging and further complicated by ethical concerns, significantly limiting their potential for clinical transplantation. The reprogramming of fibroblasts to an ESC-like state, pioneered by Yamanaka and colleagues, has advanced stem cell research (Takahashi and Yamanaka, 2006, Cell 126:663-676) by circumventing these obstacles. These so called 'induced Pluripotent Stem (iPS) cells' derived from mouse or human fibroblasts have demonstrated that an entire organism can be derived from readily accessible post-natal somatic cells. iPS cells provide a powerful in vitro model system for the study of the molecular mechanisms of reprogramming and have been successfully employed in proof-of-principle cell-based therapies in mouse models of disease. However, to date the derivation of iPS cells has required multiple individual viral vectors to deliver the constellation of transcription factors (typically OCT4, SOX2, KLF4, and c-MYC) required to induce reprogramming. The application of sufficient quantities of each virus needed to deliver four factors simultaneously to each target cell results in high numbers of genomic integrations in successfully reprogrammed progeny. This presence of multiple viral integrations across the genome makes their genetic elimination to produce safer iPS cells very difficult. Moreover, many cells will receive only one, two or three factors, making it difficult to study the biochemistry of reprogramming on a homogeneous population of cells. Hence there is a need for improved methods that provide consistent delivery of reprogramming transcription factors and with minimal or no viral integrations across the genome to produce safer iPS cells.

SUMMARY OF THE INVENTION

The present invention is based on the discovery that a single lentiviral vector expressing multiple individual transcription factor proteins from a single multi-cistronic mRNA can reprogram a fibroblast cell to a stem cell-like cell. These reprogrammed iPS cells are pluripotent as evidenced by their ability to divide unlimited times to form teratomas and to contribute to chimeric embryos. The integration of a single copy of the lentiviral vector was sufficient to reprogram the fibroblast cell.

Furthermore, the inventors demonstrate efficient derivation of transgene-free iPS cells using an excisable polycistronic lentiviral vector. In other words, after the integration of the polycistronic lentiviral vector that brought about the deprogramming of differentiated cells, the integrated polycistronic lentiviral vector can be efficiently excised to leave behind lentivirus-free iPS cells. A direct comparison of iPS cell clones before and after excision reveals that removal of the reprogramming vector markedly improves the developmental potential of iPS cells and significantly augments their capacity to undergo directed differentiation in vitro.

Furthermore, a specific marker gene can be incorporated into the polycistronic lentiviral vector for the purpose of monitoring the presence or absence of the lentivirus in the lentivirus-integrated iPS cells or lentivirus-free iPS cells respectively. The specific marker gene can be one that expresses optically visible proteins such as the green fluorescent protein or the red "cherry" fluorescent protein described herein or an enzyme whose activity can be assayed, e.g., thymidine kinase.

Accordingly, in one embodiment, the invention described herein provides a lentiviral vector particle capable for reprogramming a somatic cell to a stem-cell-like cell, the vector particle comprising a nucleic acid sequence comprising encoding sequences of multiple individual transcription factor proteins sufficient to reprogram a somatic cell. For example, a sequence encoding: (a) a Oct4 gene; (b) a Klf4 gene; (c) a Sox2 gene; (d) a c-Myc gene; (e) a first 'self-cleaving' 2A peptide; (f) a second 'self-cleaving' 2A peptide; (g) an internal ribosome entry site (IRES); wherein the nucleic acid sequence is operably linked to a promoter; and wherein the sequences encoding OCT4, KLF4, SOX2, c-MYC, first and second 'self-cleaving' 2A peptides, and the IRES are transcribed from the promoter as a multi-cistronic RNA.

In another embodiment, the sequence encoding: (a) a Oct4 gene; (b) a Klf4 gene; (c) a Sox2 gene; (d) a specific marker gene; (e) a first 'self-cleaving' 2A peptide; (f) a second 'self-cleaving' 2A peptide; (g) an internal ribosome entry site (IRES); wherein the nucleic acid sequence is operably linked to a promoter; and wherein the sequences encoding OCT4, KLF4, SOX2, c-MYC, first and second 'self-cleaving' 2A peptides, and the IRES are transcribed from the promoter as a multi-cistronic RNA, wherein the specific marker gene encodes a fluorescent protein or an enzyme, e.g. thymidine kinase.

In one embodiment, the nucleic acid sequence comprising encoding sequences of multiple individual transcription factor proteins sufficient to reprogram a somatic cell can be selected from the group consisting of OCT4, KLF4, SOX2, LIN28, NANOG and c-MYC. In some embodiments, the nucleic acid sequence comprises encoding sequences of multiple individual transcription factor proteins sufficient to reprogram a somatic cell comprises three or four of the transcription factors selected from the group consisting of OCT4, KLF4, SOX2, LIN28, NANOG and c-MYC. For example, the nucleic acid sequence comprises encoding sequences of OCT4, KLF4 and SOX2, sequences of OCT4, KLF4, LIN28 and NANOG, sequences of OCT4, LIN28, NANOG and c-MYC.

In one embodiment, the somatic cell is a mammalian cell. In one embodiment, the somatic cell is a mammalian cell derived from internal organs-heart, kidney, liver, lungs, bladder, intestines; skin, bone, blood, cartilage and connective tissues.

In one embodiment, the sequences encoding the multiple individual transcription factors such as the four genes: Oct4, Klf4, Sox2, and c-Myc, are arranged in tandem, wherein the genes are oriented in the sense direction, and wherein the genes are arranged in any order.

In some embodiments, the sequence encodes only four genes selected from the group consisting of Oct4, Klf4, Sox2, Lin28, Nanog and c-Myc. In other embodiments, sequence encodes only three genes selected from the group consisting of Oct4, Klf4, Sox2, Lin28, Nanog and c-Myc, e.g. Oct4, Klf4, and Sox2; Oct4, Klf4, and c-Myc; or Oct4, Sox2 and Lin28. In the embodiments where only three genes are used, the specific marker gene can form the fourth gene in the tandemly arranged sequence. For example, Oct4, Klf4, Sox2 and a specific marker gene, Oct4, Klf4, Lin28 and a specific marker gene, and Oct4, Lin28, c-Myc and a specific marker gene.

In one embodiment, the sequence encoding internal ribosome entry site (IRES) is between the second and third genes in the tandem arrangement of the four genes, e.g. Oct4, Klf4, Sox2, and c-Myc. The arrangement is then Oct4, Klf4, IRES, Sox2, and c-Myc.

In one embodiment, the sequence encoding the first 'self-cleaving' 2A peptide is between the first and second genes in the tandem arrangement the four genes, e.g. Oct4, Klf4, Sox2, and c-Myc. The arrangement is then Oct4, 1$^{st}$ 2A, Klf4, IRES, Sox2, and c-Myc.

In one embodiment, the sequence encoding the second 'self-cleaving' 2A peptide is between the third and forth genes in the tandem arrangement the four genes, e.g. Oct4, Klf4, Sox2, and c-Myc. The arrangement is then Oct4, first 'self-cleaving' 2A peptide, Klf4, IRES, Sox2, second 'self-cleaving' 2A peptide, and c-Myc.

In some embodiments, the first and the second 'self-cleaving' 2A peptide is selected from the group consisting of F2A, E2A, T2A and P2A, wherein the second 'self-cleaving' 2A peptide is different from the first 'self-cleaving' 2A peptide.

In one embodiment, the promoter is inducible, for example, a tetracycline regulated promoter.

In another embodiment, the promoter is constitutive, for example, a EF-1alpha promoter In one embodiment, the polycistronic lentiviral vector comprises sequences that facilitate the excision of the integrated vector, e.g. Cre-LoxP and Cre-ERT2 sequences wherein the excision is executed with Cre recombinase protein or tamoxifen via the inducible Cre-ERT2 recombinase respectively.

In another embodiment, the invention described herein provides a method of reprogramming a somatic cell; the method comprising contacting a somatic cell with a lentiviral vector described herein. In one embodiment, the somatic cell is a mammalian cell. In one embodiment, the somatic cell is a mammalian cell derived from internal organs-heart, kidney, liver, lungs, bladder, intestines; skin, bones, blood, cartilage and connective tissues.

BRIEF DESCRIPTION OF THE DRAWINGS

FIG. 4A shows the teratomas derived from iPS lines produced with pHAGE-EF1α-STEMCCA vector, showing differentiation into cell types of all three germ layers: endoderm (end), mesoderm (mes) and ectoderm (ect). Images are representative of two independent experiments testing three individual iPS clones for each construct.

FIG. 4B shows the teratomas derived from iPS lines produced with pHAGE-Tet-STEMCCA vector, showing differentiation into cell types of all three germ layers: endoderm (end), mesoderm (mes) and ectoderm (ect). Images are representative of two independent experiments testing three individual iPS clones for each construct.

M2rtTA mouse show high levels of embryonic contribution following injections into blastocysts. Chimerism is evidenced by Sox2-GFP expression in neural crest-derived tissues in 9 of 12 mid-term embryos.

Figure 5:
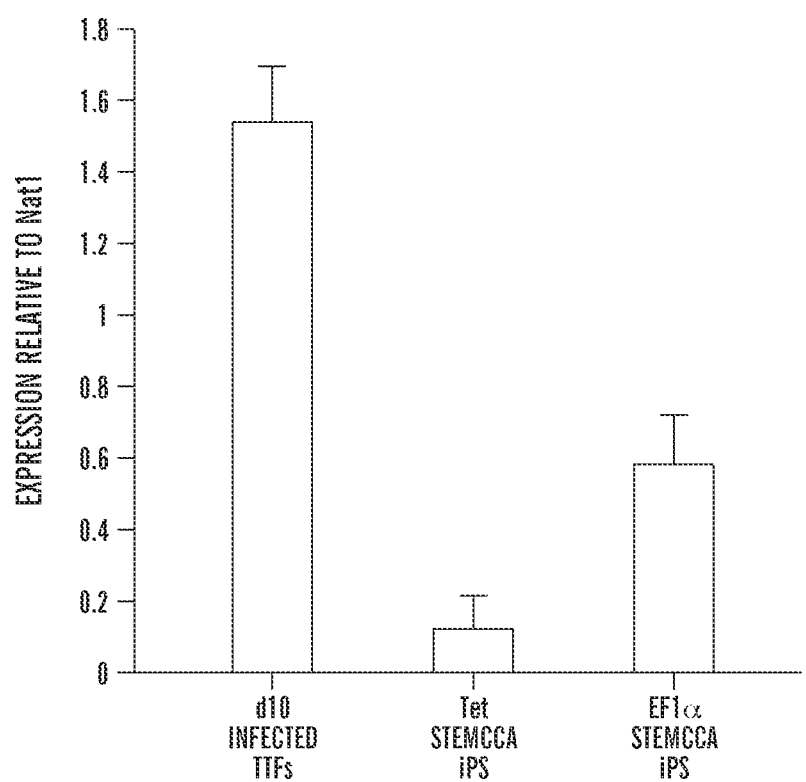

FIG. 5: STEMCCA transgene expression in transduced fibroblasts and in established iPS cell lines. Expression of the multicistronic STEMCCA transcript in transduced tail tip fibroblasts (TTFs) and established iPS clones was assessed by semi-quantitative RT-PCR. Estimated expression levels of the STEMCCA transcript relative to expression of the control constitutively expressed gene, Nat1 is shown for each sample. Ten days after doxycycline (dox) exposure, TTFs transduced with pHAGE-Tet-STEMCCA lentivirus (d10 infected TTFs) express easily detected levels of the STEMCCA transcript. In contrast, following dox withdrawal, an established iPS clone (Tet STEMCCA iPS) shows significant downregulation of expression. An established iPS clone generated using the 'constitutive' pHAGE-EF1a-STEMCCA lentivirus (EF1a STEMCCA iPS), expresses the STEMCCA transcript at lower levels than the dox-exposed TTFs, but at higher levels than the Tet STEMCCA iPS clone. Error bars indicate standard deviations (n=3).

Figure 6A:
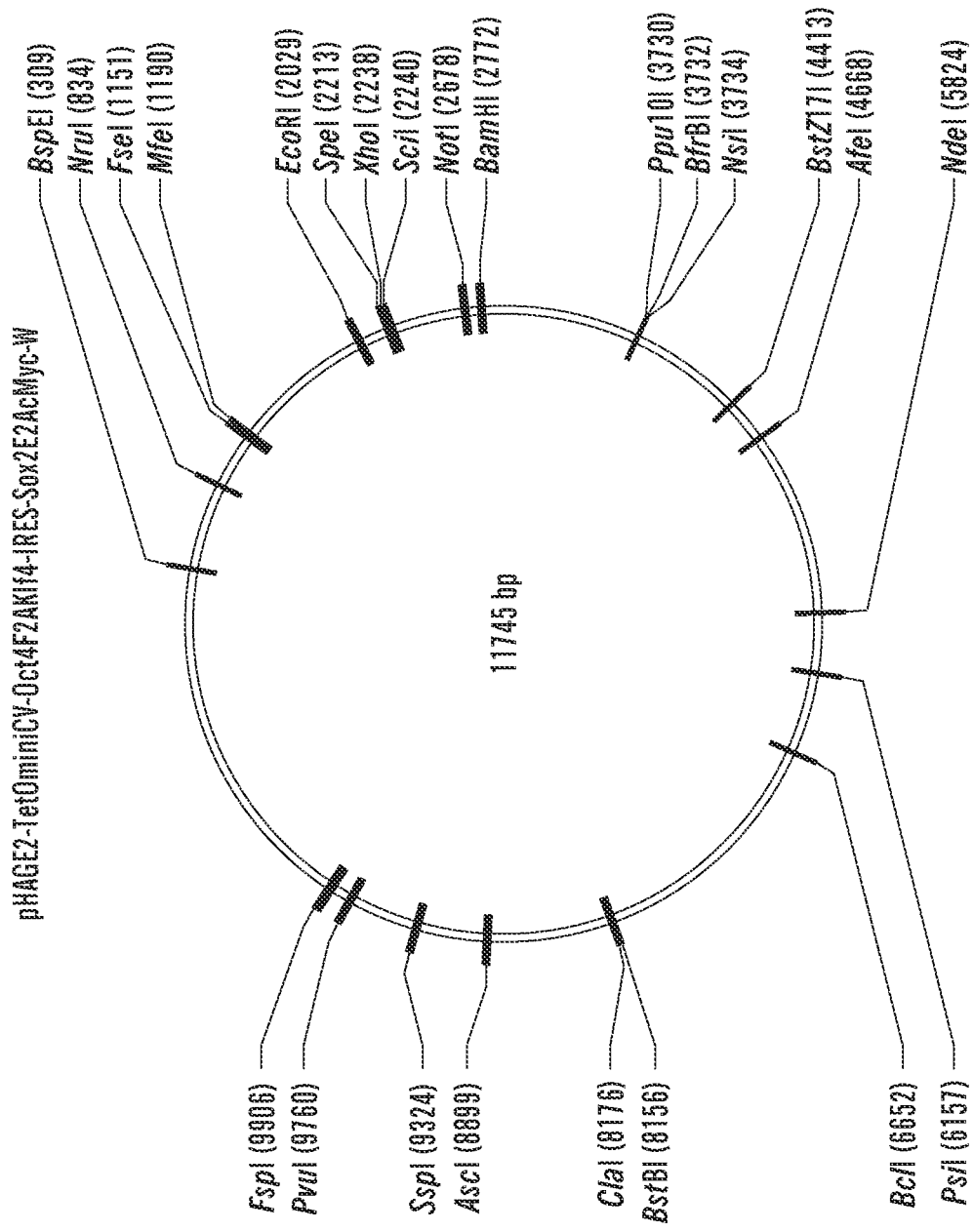

FIG. 6A is a map of pHAGE-Tet-STEMCCA gene transfer plasmid showing the restriction enzyme sites. The transfer plasmid is also known as pHAGE2-TetOminiCV-Oct4F2aK1f4-IRES-Sox2E2AcMyc-W.

Figure 6B:
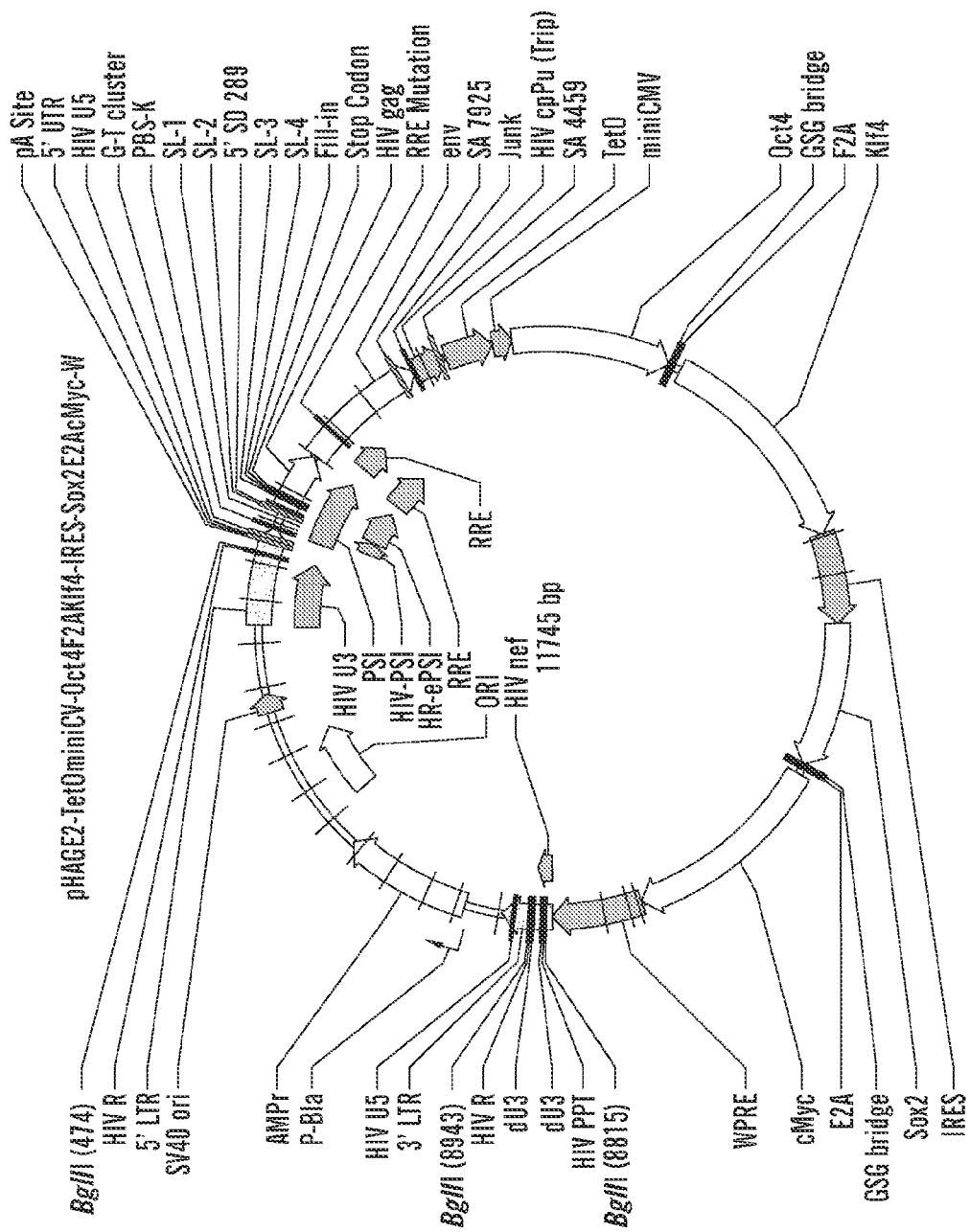

FIG. 6B is a map of pHAGE-Tet-STEMCCA gene transfer plasmid showing the major operational elements of the plasmid. The transfer plasmid is also known as pHAGE2-TetOminiCV-Oct4F2aK1f4-IRES-Sox2E2AcMyc-W.

Figure 7A:
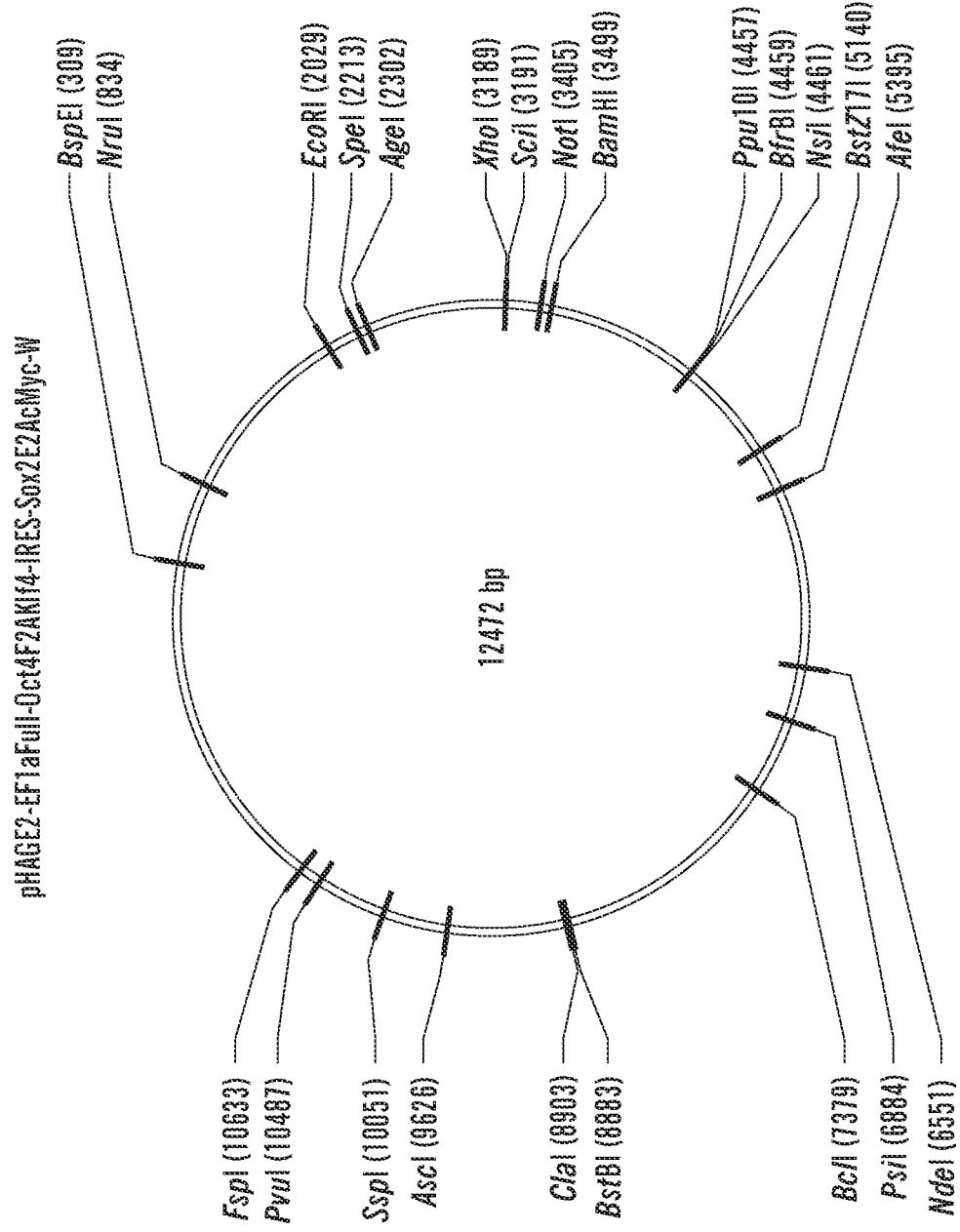

FIG. 7A is a map of pHAGE-EF1α-STEMCCA gene transfer plasmid showing the restriction enzyme sites. The transfer plasmid is also known as pHAGE2-EF1αFull-Oct4F2aK1f4-IRES-Sox2E2AcMyc-W.

Figure 7B:
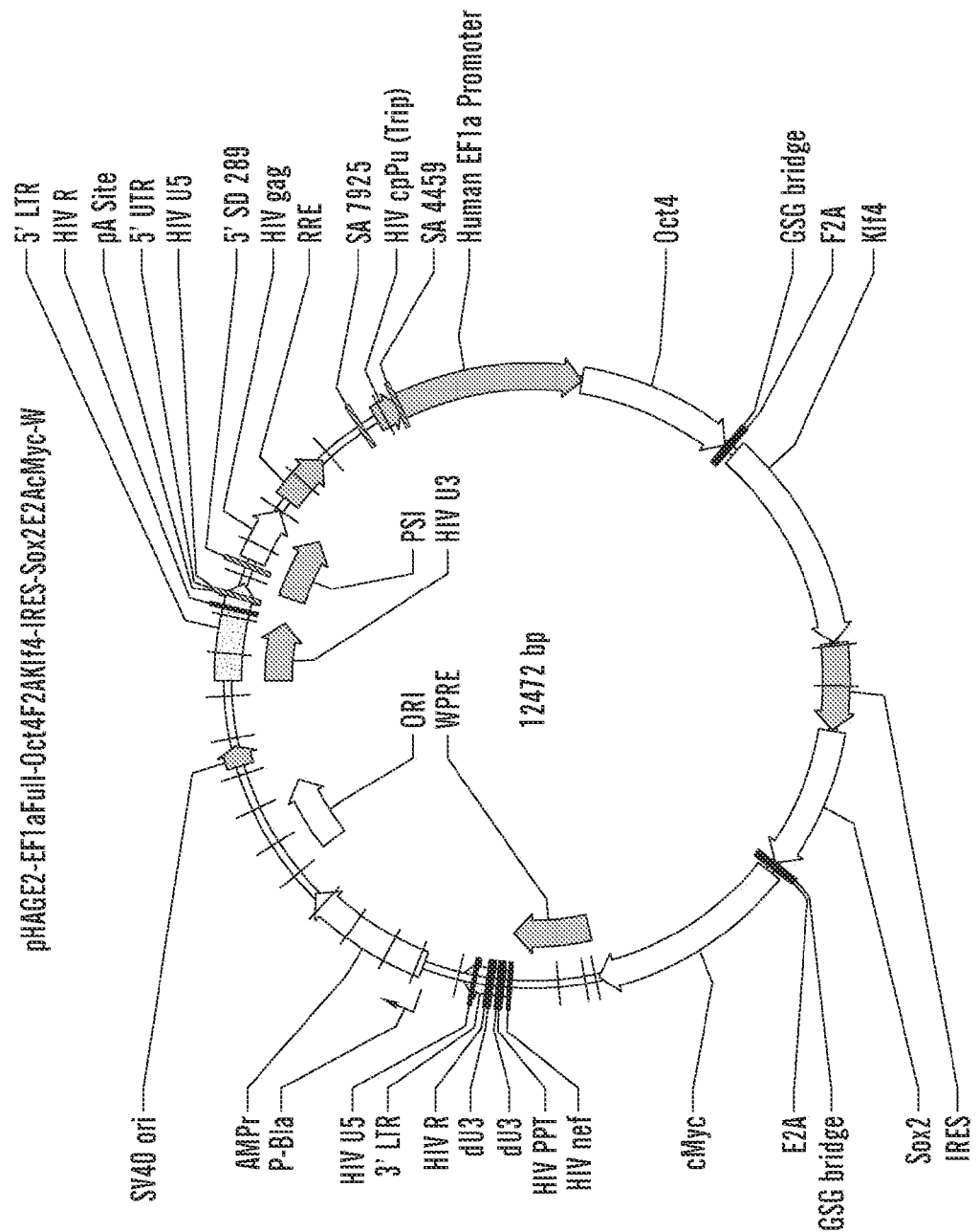

FIG. 7B is a map of pHAGE-EF1α-STEMCCA gene transfer plasmid showing the major operational elements of the plasmid. The transfer plasmid is also known as pHAGE2-EF1αFull-Oct4F2aK1f4-IRES-Sox2E2AcMyc-W.

Figure 8A:
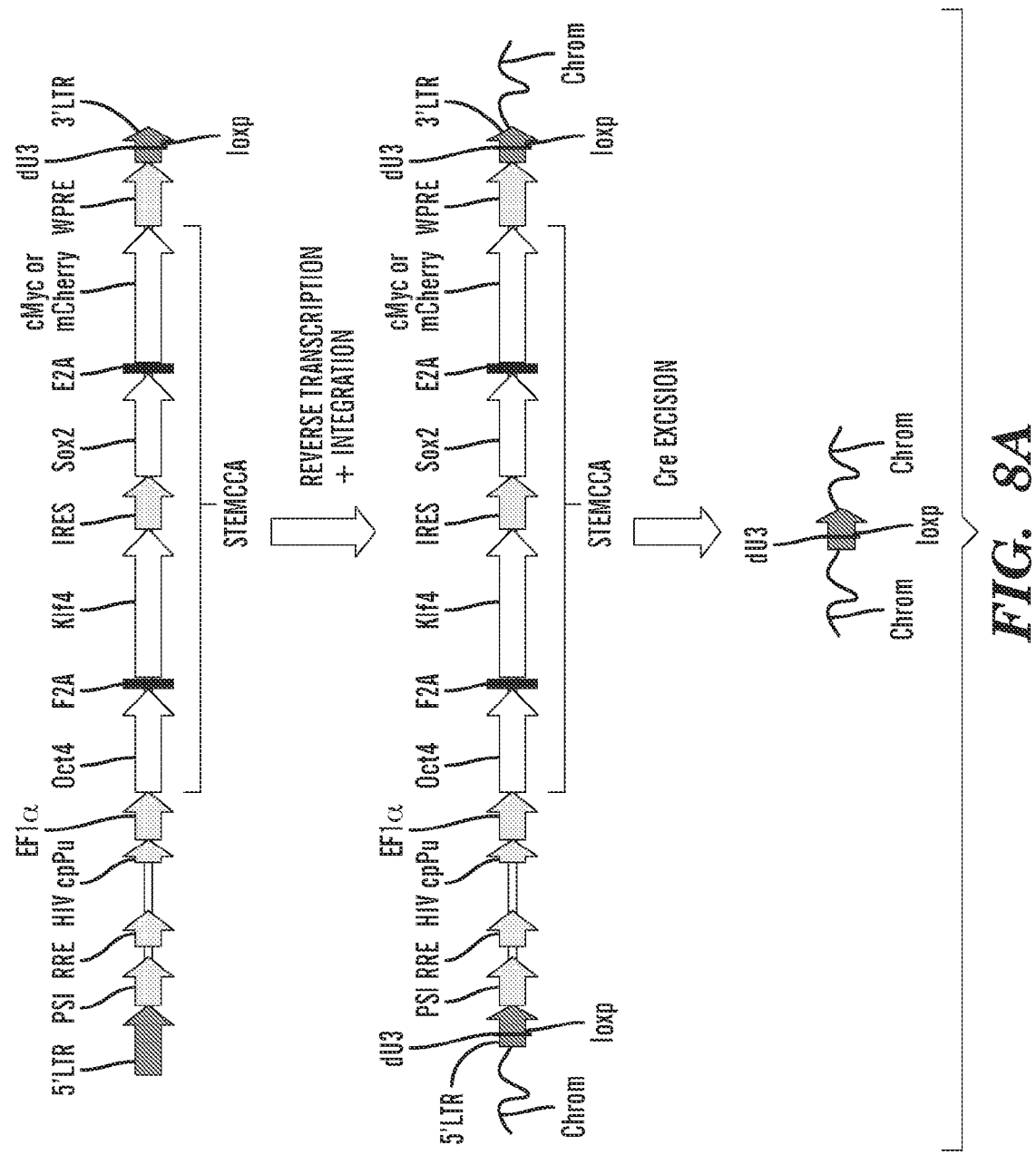

FIG. 8A shows the schematic representation of the STEMCCA-loxP (SEFL) or STEMCCA-loxP-RedLight (SEFCL) lentiviral vector, excisable single lentiviral vectors for the generation of iPS cells free of exogenous transgenes. The 'RedLight' indicate the mCherry gene in the vector. This vector is a constitutive promoter EF1α.

FIG. 8B shows the analysis of iPS cells created using the STEMCCA-loxP-RedLight vector using flow cytometry to detect mCherry fluorescence. Cells before and after Cre treatments are shown.

FIG. 8C shows the Southern blot analysis of genomic DNA (gDNA) purified from two representative iPS clones produced with the STEMCCA-loxP vector, before and after Cre-mediated excision.

FIG. 8D shows the expression of the STEMCCA transcript was analyzed by RT-PCR to confirm excision. As expected, clones SEFL1-Cre and SEFL2-Cre showed no detectable STEMCCA transcript. Nat1 is a constitutively expressed gene and serves as a control for loading.

Figure 9A:
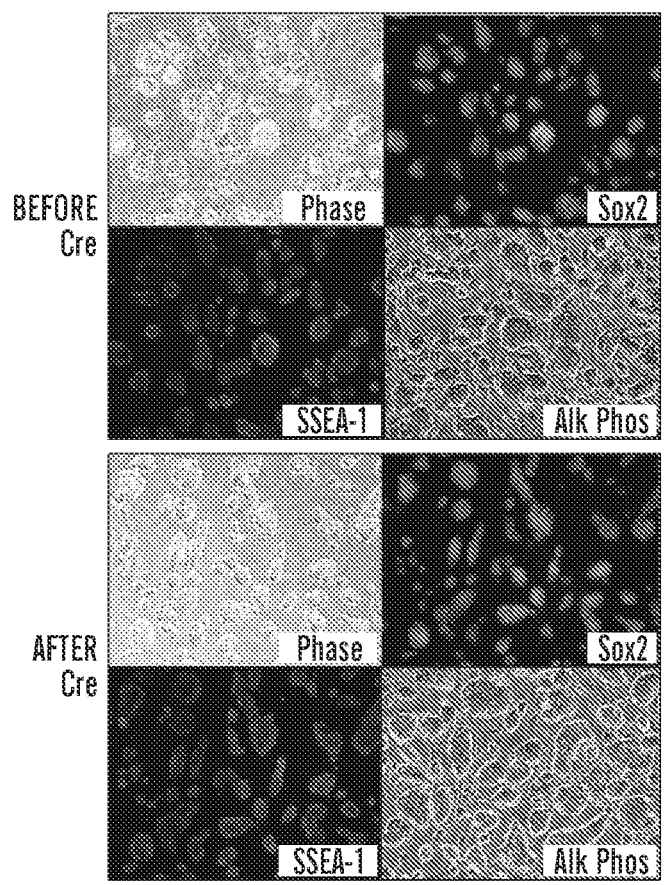

FIG. 9A shows representative images of iPS cells derived using the constitutive STEMCCA-loxP vector before and after Cre-mediated excision showing normal colony morphology (Phase), Sox2-GFP reporter gene expression, SSEA1 positive immunostaining, and robust alkaline phosphatase activity (Alk Phos).

FIG. 9B shows the expression of ESC 'marker' genes detected by RT-PCR in iPS cell clones before (SEFL1 and SEFL2) and after excision (SEFL1-Cre and SEFL2-Cre). Representative samples from murine ESC and unmanipulated tail tip fibroblasts (TTFs) are also shown for comparison. An iPS cell sample prepared without RT was used as negative control (—RT).

FIG. 9C shows the analysis of the promoter regions of Nanog and Oct4 genes by determining the methylation status using bisulfite sequencing. Similar to ESC, all iPS cell clones (SEFL1, SEFL1-Cre, SEFL2 and SEFL2-Cre) showed mostly unmethylated CpG motifs (open circles) in sharp contrast to parental TTFs, in which the extracted DNA was mostly methylated (closed circles).

Figure 10A:
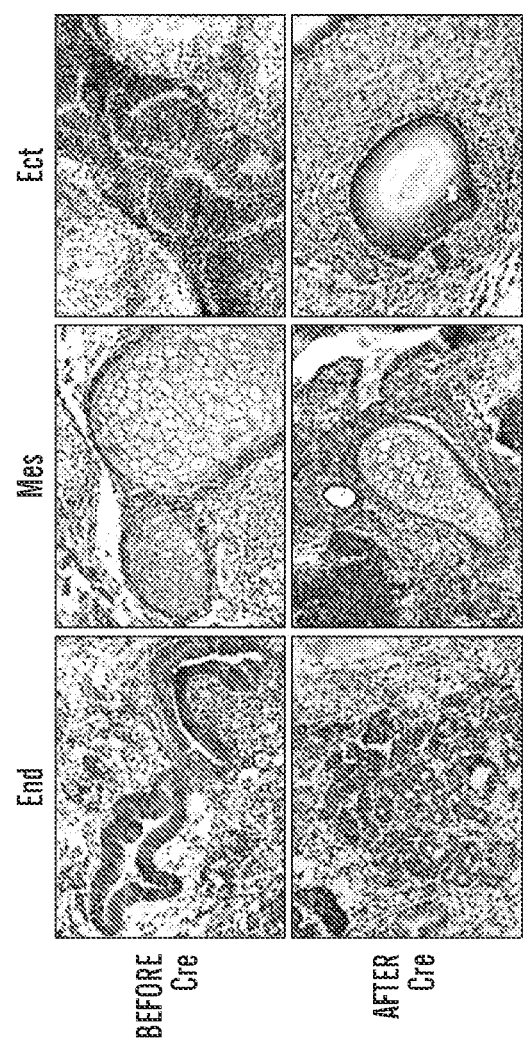

FIG. 10A shows the teratomas derived from iPS cell lines produced with STEMCCA-loxP vector, before and after Cre excision, showing differentiation into cell types of all three germ layers: endoderm (end), mesoderm (mes) and ectoderm (ect).

Figure 10B:
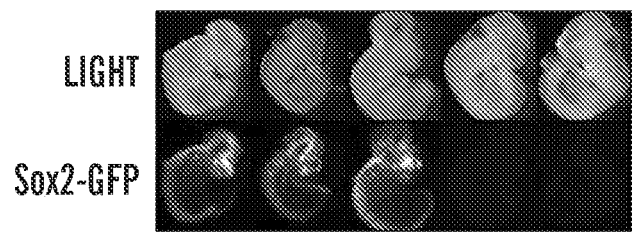
Figure 10C:
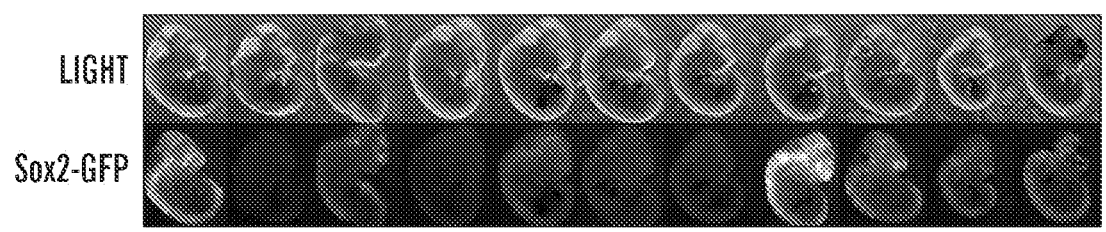

FIG. 10B shows representative images of embryos with iPS cells generated with the constitutive STEMCCA vector (no Cre-excision) displayed high levels of embryonic contribution following injection into blastocysts, but also induced gross morphological abnormalities FIG. 10C shows representative images of embryos with iPS cells generated using the STEMCCA-loxP vector with subsequent Cre excision produces a higher percentage of chimeric embryos with normal developmental morphology. Chimerism is evidenced by Sox2-GFP expression in neural crest-derived tissues.

Figure 10D:
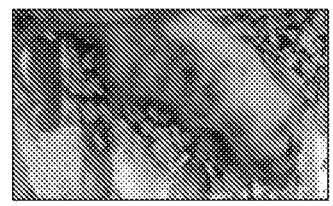

FIG. 10D shows the derivation of neonatal chimeric mice from blastocysts injected with iPS cells generated using the STEMCCA-loxp vector with subsequent Cre excision. Chimerism is evidenced by dark coat color.

Figure 11A:
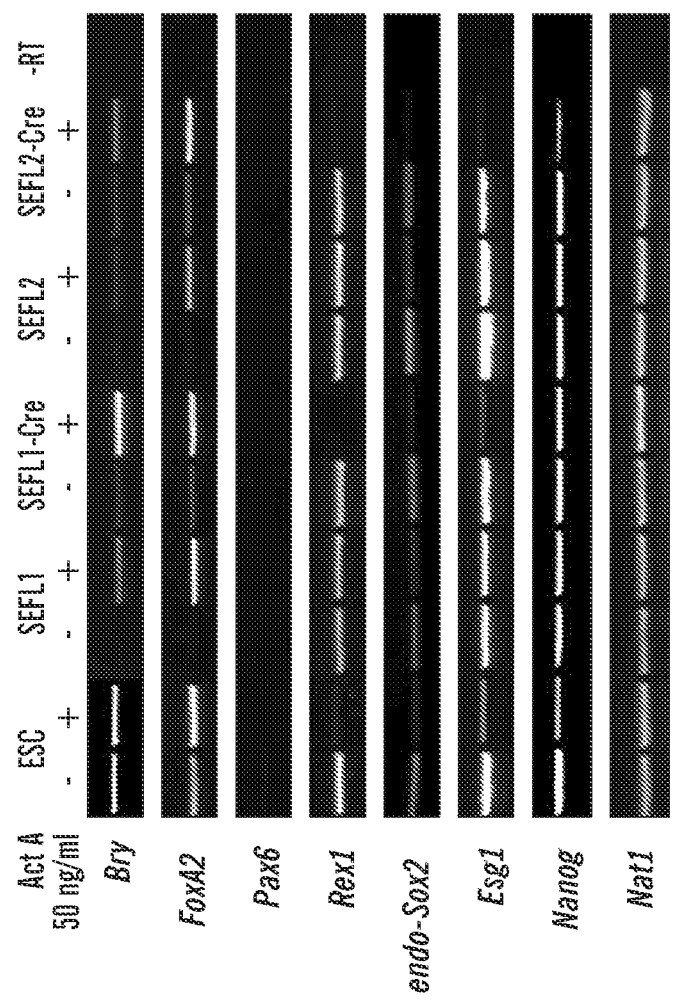

FIG. 11A shows representative RT-PCR data of iPS clones subjected to in vitro differentiation toward primitive streak/endoderm using activin A stimulation (Act A).

Figure 11B:
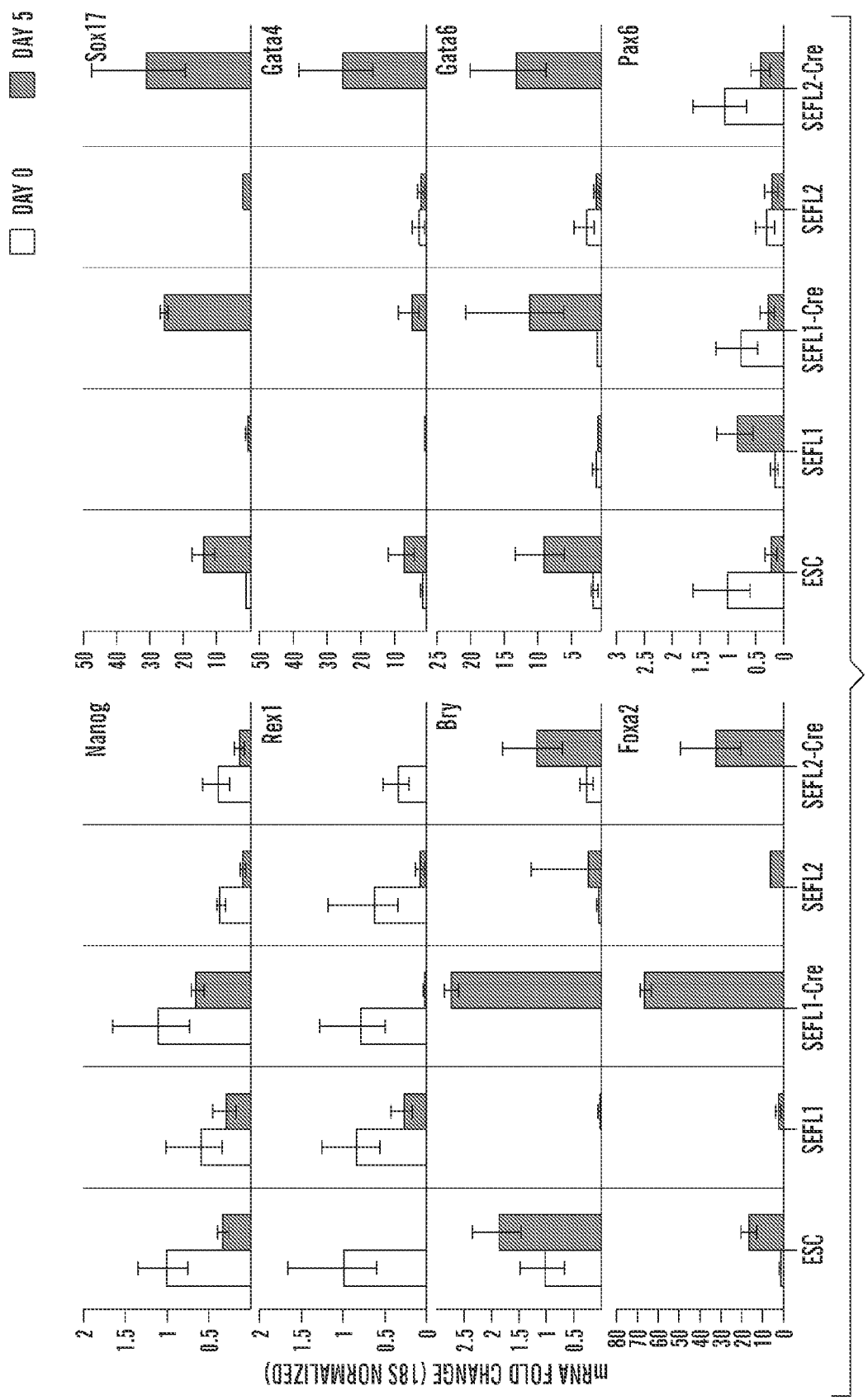

FIG. 11B shows the quantitative RT-PCR data for iPS cells stimulated in vitro using activin A. Data is expressed as fold change normalized to 18S expression. mRNA extracted on day 0 (light grey columns) or day 5 (dark grey columns) of activin A stimulation served as the template for qRT-PCR.

Figure 12:
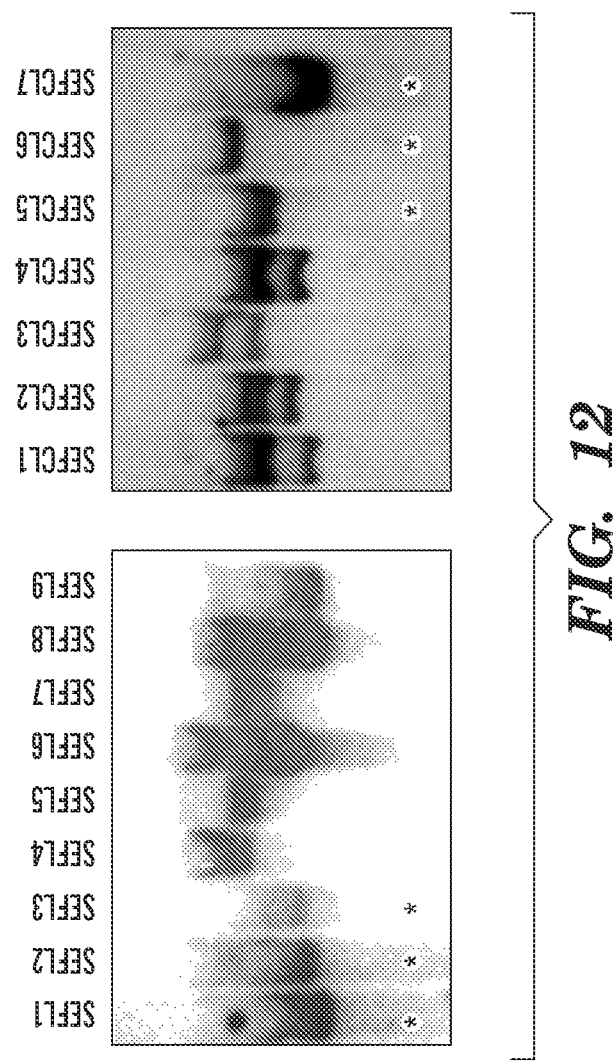

FIG. 12 shows the Southern blot analysis of iPS cell clones generated with STEMCCA-loxP (SEFL) or STEMCCA-loxP-RedLight (SEFCL) showing number of proviral integrations. Several clones displaying a single integration are shown (asterisk). gDNA was digested with BamHI that cuts once within the provirus. Blots were probed against the WPRE element present in both STEMCCA vectors.

Figure 13:
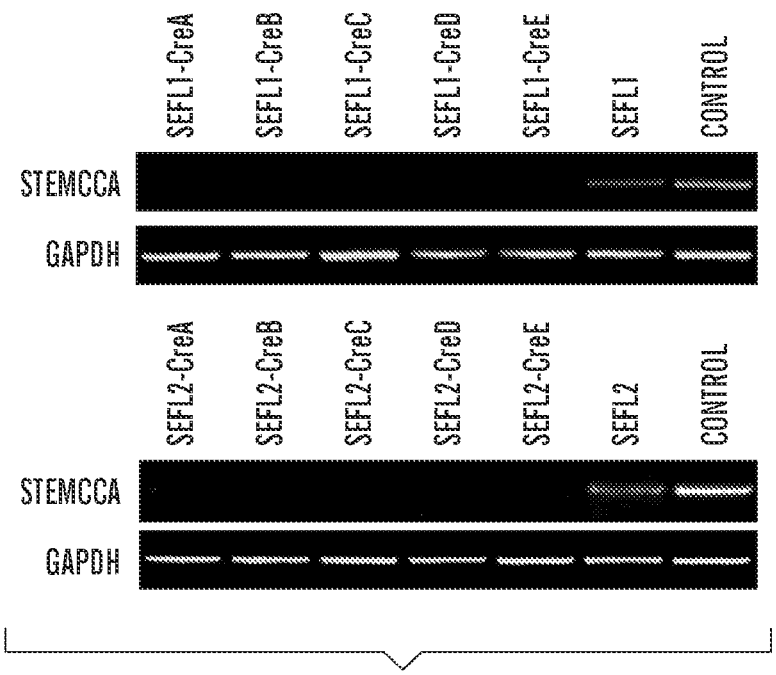

FIG. 13 shows that the PCR of a c-Myc to WPRE fragment using gDNA isolated from several iPS sub-clones post Cre excision (SEFL1-Cre and SEFL2-Cre) shows absence of band. gDNA samples isolated from the parental lines (SEFL1 and SEFL2) show positive PCR amplification. gDNA isolated from a previously generated iPS clone containing a single copy of the constitutive STEMCCA was used as positive control for PCR reaction (Control).

Figure 14:
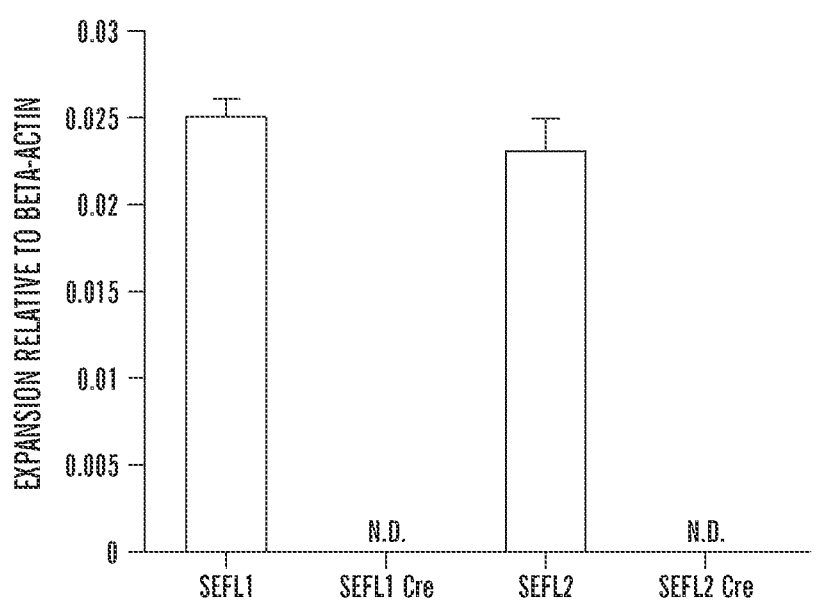

FIG. 14 shows that the quantitative real time PCR (qRT-PCR) performed on two independent iPS clones generated with the STEMCCA-loxP vector (SEFL1 and SEFL2) produces equivalent levels of STEMCCA expression. The STEMCCA transcript was not present after Cre-mediated excision of the STEMCCA vector (SEFL1 Cre and SEFL2-Cre). N.D.: Not Detected.

Figure 15A:
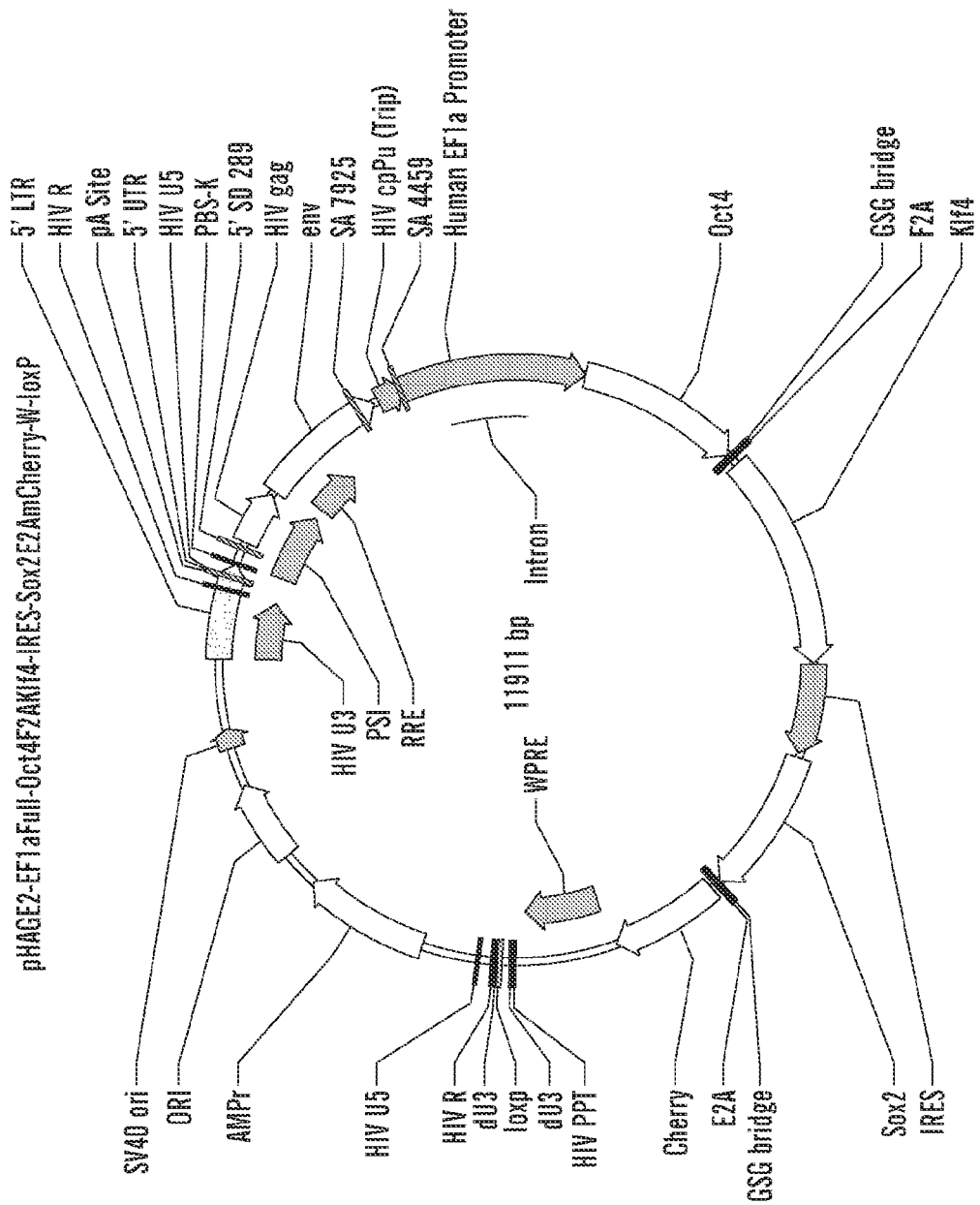

FIG. 15A is a map of pHAGE-EF1αFull-STEMCCA-W-RedLight-LoxP gene transfer plasmid showing the restriction enzyme sites. This vector has the LoxP flanking the STEMCCA and the fourth gene in the cassette, c-Myc, has been replaced with a marker gene, mCherry, which codes for a red fluorescent protein. This transfer plasmid is also known as pHAGE-EF1α-STEMCCA-LoxP-RedLight and pHAGE2-EF1αFull-Oct4F2aK1f4-IRES-Sox2E2AmCherry-W-LoxP.

Figure 15B:
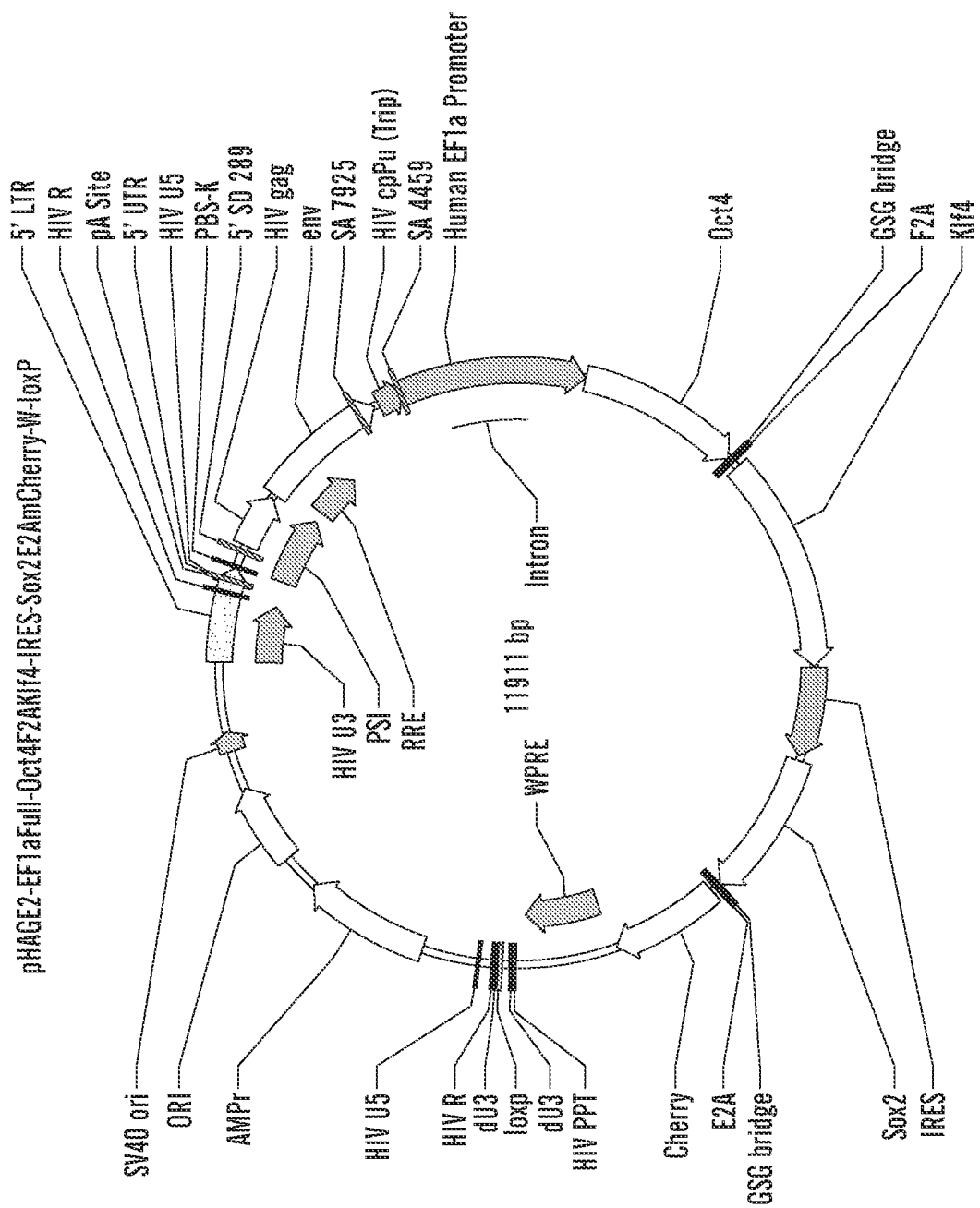

FIG. 15B is a map of pHAGE-EF1αfull-STEMCCA W-RedLight-LoxP gene transfer plasmid showing the major operational elements of the plasmid. This vector has the LoxP flanking the STEMCCA and the fourth gene in the cassette, c-Myc, has been replaced with a marker gene, mCherry, which codes for a red fluorescent protein. This transfer plasmid is also known as pHAGE-EF1α-STEMCCA-LoxP-RedLight and pHAGE2-EF1αFull-Oct4F2aK1f4-IRES-Sox2E2AmCherry-W-LoxP.

DETAILED DESCRIPTION OF THE INVENTION

Definitions of Terms

As used herein, the term "a somatic cell" refers to any cell forming the body of an organism that are not germline cells (e.g. sperm and ova, the cells from which they are made (gametocytes)) and undifferentiated stem cells. Internal organs, skin, bones, blood and connective tissue are all made up of somatic cells.

As used herein, the term "self-cleaving 2A peptide" refers to relatively short peptides (of the order of 20 amino acids long, depending on the virus of origin) containing the consensus motif D-V/I-E-X-N-P-G-P (SEQ ID NO: 52; preferred embodiments disclosed as SEQ ID NOS 1-2). They were originally thought to mediate the autocatalytic proteolysis of the large polyprotein, but are now understood to act co-translationally, by preventing the formation of a normal peptide bond between the glycine and last proline, resulting in the ribosome skipping to the next codon, and the nascent peptide cleaving between the Gly and Pro. After cleavage, the short 2A peptide remains fused to the C-terminus of the 'upstream' protein, while the proline is added to the N-terminus of the 'downstream' protein. The 2A peptide was identified among Picornaviruses but in a different sub-group, the Aphthoviruses, a typical example of which is the Foot-and-mouth disease virus.

As used herein, the term "promoter" refers to a regulatory region of DNA generally located upstream (towards the 5' region of the sense strand) of a gene that allows transcription of the gene. The promoter contains specific DNA sequences and response elements that are recognized by proteins known as transcription factors. These factors bind to the promoter sequences, recruiting RNA polymerase, the enzyme that synthesizes the RNA from the coding region of the gene.

As used herein, the term "cistron" refers to a section of the DNA molecule that specifies the formation of one polypeptide chain, i.e. coding for one polypeptide chain. A fusion cistron refers to two or more sections of different DNA molecule fused together to specify the formation of one polypeptide chain.

As used herein, the term "multi-cistronic RNA" or "multi-cistron RNA" refers to an RNA that contains the genetic information to translate to several proteins. In contrast, a monocistronic RNA contains the genetic information to translate only a single protein. In the context of the present invention, the multi-cistronic RNA transcribed from the lentivirus in the Example 1 is translated to four proteins: OCT4, KLF4, SOX2, and c-MYC. Likewise, the multi-cistronic RNA transcribed from the lentivirus in the Example 2 is translated to four proteins: OCT4, KLF4, SOX2, and mCHERRY fluorescent protein.

As used herein, the term "arranged in tandem" refers to the arrangement of the genes back to back, one following or behind the other, in a single file on a nucleic acid sequence. The genes are ligated together back to back in a single file on a nucleic acid sequence, with the coding strands (sense strands) of each gene ligated together on a nucleic acid sequence.

As used herein, the term "sense strand" refers to the DNA strand of a gene that is translated or translatable into protein. When a gene is oriented in the "sense direction" with respect to the promoter in a nucleic acid sequence, the "sense strand" is located at the 5' end downstream of the promoter, with the first codon of the protein is proximal to the promoter and the last codon is distal from the promoter.

The term "constitutive" use herein refers to "all the time" or constantly. For example, a gene product that is expressed all the time is constitutively expressed. A "constitutive" promoter is active all the time, transcribing the attached gene to primary RNA transcript all the time. Such a promoter is unregulated and it allows for continual transcription of its associated gene. Examples of "constitutive" eukaryotic promoters are elongation factor 1 alpha (EF1α) and cytomegalovirus (CMV).

As used herein, the term "inducible" refers to regulatable. For example, the activity of an inducible promoter can be turned on or off, i.e. regulated by the presence or absence of biotic or abiotic factors. Examples of inducible promoters include: chemically-regulated promoters, including promoters whose transcriptional activity is regulated by the presence or absence of alcohol, tetracycline, steroids, metal and other compounds; and physically-regulated promoters, including promoters whose transcriptional activity is regulated by the presence or absence of light and low or high temperatures. Examples chemically inducible promoters can have hormone-responsive elements (HREs), metal-responsive elements (MREs), heat shock-responsive elements (HSREs), tetracycline operator sequence (TetO) and interferon-responsive elements (IREs).

As used herein the term "comprising" or "comprises" is used in reference to vector particles, vector systems, methods, and respective component(s) thereof, that are essential to the invention, yet open to the inclusion of unspecified elements, whether essential or not.

The term "consisting of" refers to vector particles, vector systems, methods, and respective components thereof as described herein, which are exclusive of any element not recited in that description of the embodiment.

As used herein, the term "exogenous copy" of a gene refers to the non-genomic copy of a gene, an added copy of gene that is introduced into the cell, for example, in the form of a cDNA copy. The term "endogenous" use herein means the original copy of the gene found in the genome of the cell.

As used herein, the term "transgene" refers to a nucleic acid sequence which is partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can be operably linked to one or more transcriptional regulatory sequences and any other nucleic acid, such as introns, that may be necessary for optimal expression of a selected nucleic acid.

"Functional variant" refers to a nucleic acid or protein having a nucleotide sequence or amino acid sequence, respectively, that is "identical," "essentially identical," "substantially identical," "homologous" or "similar" to a reference sequence which can, by way of non-limiting example, be the sequence of an isolated nucleic acid or protein, or a consensus sequence derived by comparison of two or more related nucleic acids or proteins, or a group of isoforms of a given nucleic acid or protein. Non-limiting examples of types of isoforms include isoforms of differing molecular weight that result from, e.g., alternate RNA splicing or proteolytic cleavage; and isoforms having different post-translational modifications, such as glycosylation; and the likes.

As used herein, the term "variants" or "variant" refers to a nucleic acid or polypeptide differing from a reference nucleic acid or polypeptide, but retaining essential properties thereof. Generally, variants are overall closely similar, and, in many regions, identical to the reference nucleic acid or polypeptide. Thus "variant" forms of a transcription factor are are overall closely similar, and capable of binding DNA and activate gene transcription.

As used herein, the term "conservative amino acid substitution" is one in which the amino acid residue is replaced with an amino acid residue having a side chain with a similar charge and size. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

As used herein, the term "stem cell-like cell" refers to refers to a cell that has been transfected with exogenous gene copies of multiple individual transcription factors such as OCT4, KLF4, SOX2, C-MYC, LIN28 and NANOG and the cell has acquired characteristics of an unspecialized "stem cell" such as the ability to self-renewal and potency. The potency can be pluripotent or multipotent. A stem cell-like cell is less differentiated than its oricinal cell prior to the transfection with the exogenous genes described herein.

As used herein, the term "stem cell" refers to a cell that has the ability to self-renewal, i.e., to go through numerous cycles of cell division while maintaining the undifferentiated state, and has potency, i.e. the capacity to differentiate into specialized cell types, e.g. a nerve cell or a skin cell.

As used herein, the term "pluripotent" refers to the potential of a stem cell to make any differentiated cell in the body but not those of the placenta which is derived from the trophoblast.

As used herein, the term "multipotent" refers to the ability to only differentiate into a limited number of types. For example, the bone marrow contains multipotent stem cells that give rise to all the cells of the blood but not to other types of cells. Multipotent stem cells are found in adult animals; perhaps most organs in the body (e.g., brain, liver) contain them where they can replace dead or damaged cells. These adult stem cells may also be the cells that—when one accumulates sufficient mutations—produce a clone of cancer cells.

As used herein, the term "viral vector" refers to a nucleic acid vector construct that includes at least one element of viral origin and has the capacity to be packaged into a viral vector particle, encodes at least an exogenous nucleic acid. The vector and/or particle can be utilized for the purpose of transferring any nucleic acids into cells either in vitro or in vivo. Numerous forms of viral vectors are known in the art. The term virion is used to refer to a single infective viral particle. "Viral vector", "viral vector particle" and "viral particle" also refer to a complete virus particle with its DNA or RNA core and protein coat as it exists outside the cell.

The term "replication incompetent" as used herein means the viral vector cannot further replicate and package its genomes. For example, when the cells of a subject are infected with replication incompetent recombinant lentivirus such as the human immunodeficiency virus (HIV) or feline immunodeficiency virus (FIV), the heterologous (also known as transgene) gene is expressed in the patient's cells, but, the rHIV is replication defective (e.g., lacks essential packaging elements of the virus) and viral particles cannot be formed in the patient's cells.

The term "gene" means the nucleic acid sequence which is transcribed (DNA) and translated (mRNA) into a polypeptide in vitro or in vivo when operably linked to appropriate regulatory sequences. The gene may or may not include regions preceding and following the coding region, e.g. 5' untranslated (5'UTR) or "leader" sequences and 3' UTR or "trailer" sequences, as well as intervening sequences (introns) between individual coding segments (exons).

The term "nucleic acid" refers to deoxyribonucleotides or ribonucleotides and polymers thereof ("polynucleotides") in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid molecule/polynucleotide also implicitly encompasses conservatively modified variants thereof (e.g. degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyino sine residues (Batzer et al., Nucleic Acid Res. 19: 5081 (1991); Ohtsuka et al., J. Biol. Chem. 260: 2605-2608 (1985); Rossolini et al., Mol. Cell. Probes 8: 91-98 (1994)). Nucleotides are indicated by their bases by the following standard abbreviations: adenine (A), cytosine (C), thymine (T), and guanine (G).

As used herein, the term "operably linked" refers to that the regulatory elements in the nucleic acid construct are in-frame with a nucleic acid coding for a protein or peptide.

Embodiments of the present invention is based on the discovery that a single lentiviral cassette can be used to create a single lentiviral vector, expressing four individual transcription factor proteins from a single multi-cistronic mRNA to reprogram a fibroblast cell to a stem cell-like cell having the capacity to divide unlimited times to form teratomas. The integration of a single copy of the lentiviral vector was sufficient to reprogram the fibroblast cell. In one embodiment, the lentiviral vector comprising the transcription factors is not integrated.

The reprogramming of fibroblasts to an ESC-like state, pioneered by Yamanaka and colleagues, has advanced stem cell research (Takahashi and Yamanaka, 2006, Cell 126, 663-676) by circumventing certain obstacles. Takahashi and Yamanaka described retroviral transfer of four transcription factors (OCT4, SOX2, KLF4, and c-MYC) into fibroblasts, resulting in extensive reprogramming of the fibroblast epigenetic state and transcriptome towards a state reminiscent of ES cells. The fibroblasts employed in those studies were highly engineered, featuring an antibiotic resistance cassette knocked into the Fbx15 locus, allowing antibiotic selection of pluripotent clones that possessed broad differentiative repertoire in teratoma assays, including the ability to differentiate into cells of all 3 germ layers. The cells created by this breakthrough have been termed induced pluripotent stem (iPS) cells to distinguish their method of derivation from that of ES cells. These so called 'induced Pluripotent Stem (iPS) cells' derived from mouse (Maherali et al., 2007, Cell Stem Cell 1, 55-70.; Okita et al., 2007, Nature 448, 313-317; Wernig et al., 2007, Nature 448, 318-324) or human fibroblasts (Takahashi et al., 2007, Cell 131, 861-872.; Yu et al., 2007, Science 318, 1917-1920) have demonstrated that an entire organism can be derived from readily accessible postnatal somatic cells. iPS cells provide a powerful in vitro model system for the study of the molecular mechanisms of reprogramming (Brambrink et al., 2008, Cell Stem Cell 2, 151-159.; Meissner et al., 2008, Nature; Mikkelsen et al., 2008, Nature 454, 49-55; Mikkelsen et al., 2007, Nature 448, 553-560.; Stadtfeld et al., 2008, Cell Stem Cell 2, 230-240) and have been successfully employed in proof-of-principle cell-based therapies in mouse models of disease (Hanna et al., 2007, Science 318, 1920-1923 Wernig et al., 2008, Proc Natl Acad Sci USA 105, 5856-5861).

However, to date the derivation of iPS cells has required multiple individual viral vectors to deliver the constellation of transcription factors (typically OCT4, SOX2, KLF4, and c-MYC) required to induce reprogramming. The application of sufficient quantities of each virus needed to deliver four factors simultaneously to each target cell results in high numbers of genomic integrations in successfully reprogrammed progeny. This presence of multiple viral integrations across the genome prohibits their genetic elimination to produce safer iPS cells (Takahashi and Yamanaka, 2006, Cell 126, 663-676). Furthermore, the use of multiple vectors severely limits its use for human clinical applications.

The inventors presented herein the generation of a single lentiviral virion (sometimes also known as capsid or vector) expressing the transcription factors necessary to induced reprogramming a somatic cell, turning it to an induced programmed stem cell (iPS) cell. For example, by expressing OCT4, SOX2, KLF4, and c-MYC from a single multicistronic RNA transcript. The coding sequences for the four transcription factors, OCT4, SOX2, KLF4, and c-MYC, are constructed into a cassette termed herein as the 'stem cell cassette' wherein the coding sequences of OCT4, SOX2, KLF4, and c-MYC are ligated in one embodiment, in tandem and in the sense orientation such that the coding sense strands of each gene are on the same strand in the cassette. An example of a recombinant lentiviral gene transfer plasmid comprising the stem cell cassette is pHAGE-STEMCCA. The lentiviral plasmid pHAGE is a third-generation self-inactivating lentiviral vector (A. B. Balazs and R. C. M., unpublished work). The detailed DNA structures of two examples of pHAGE-STEMCCA are described herein in FIGS. 6 and 7, and SEQ. ID. Nos. 23 and 24. These pHAGE-STEMCCA plasmids are packaged into lentiviruses in 293T cells.

Figure 1A:
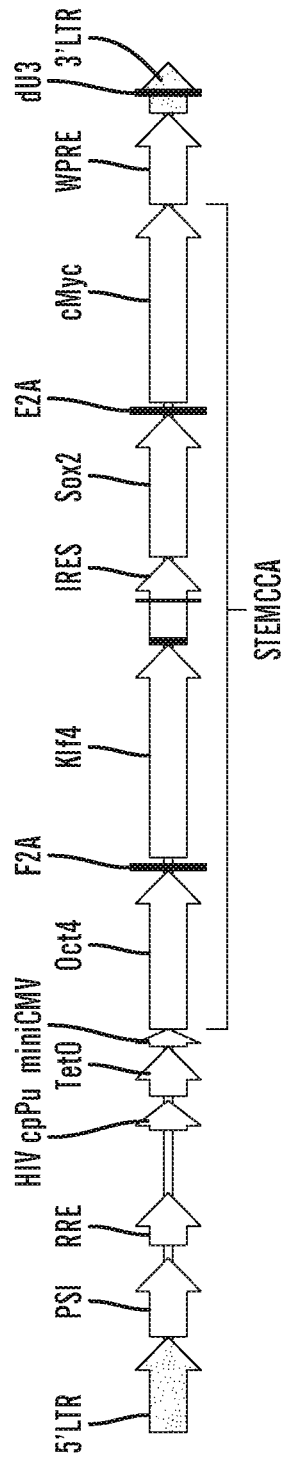
FIG. 1A shows the schematic representation of pHAGE-STEMCCA TetO/minmCMV, inducible version) generation of a single lentiviral vector expressing a stem-cell cassette. The engineered stem cell cassette consists of a single multicistronic mRNA transcribed under the control of a doxycycline-inducible TetO-miniCMV promoter. The mRNA contains an IRES element separating two fusion cistrons. The two cistrons consist of Oct4 and Sox2 coding sequences fused to Klf4 and c-Myc, respectively, through the use of intervening sequences encoding 'self-cleaving' 2A peptides (F2A and E2A). LTR: long terminal repeat; PSI: packaging signal; RRE: rev responsive element; cpPu: central polypuryne tract; WPRE: Woodchuck hepatitis virus post-transcriptional regulatory element.

This stem cell cassette achieves expression of four individual transcription factor proteins from a single multicistronic mRNA containing an IRES element separating two fusion cistrons. One fusion cistron comprises Oct4 and Klf4 coding sequences in tandem. The second cistron comprises Sox2 and c-Myc coding sequences in tandem. Sequences encoding 'self-cleaving' 2A peptides (FIG. 1A) separate the two genes in each fusion cistron. The two fusion cistrons are joined so that the Oct4 and Klf4 coding sequences are fused to Sox2 and c-Myc coding sequences, but separated by an IRES element. The single multi-cistronic mRNA contains the mRNAs of the following proteins and peptides in this order: Oct4, 'self-cleaving' 2A peptide F2A, Klf4, Sox2, E2A and c-Myc (FIG. 1A). The IRES element is found between the sequences of Sox2 and Klf4 (FIG. 1A).

Furthermore, the inventors demonstrate efficient derivation of transgene-free iPS cells using an excisable polycistronic lentiviral vector, pHAGE-STEMCCA-loxP. In other words, after the integration of the polycistronic lentiviral vector that brought about the deprogramming of differentiated cells, the integrated polycistronic lentiviral vector can be efficiently excised to leave behind lentivirus-free iPS cells. A direct comparison of iPS cell clones before and after excision reveals that removal of the reprogramming vector markedly improves the developmental potential of iPS cells and significantly augments their capacity to undergo directed differentiation in vitro.

Furthermore, a specific marker gene is incorporated into the polycistronic lentiviral vector for the purpose of monitoring the presence or absence of the lentivirus in the integrate iPS cells or lentivirus-free iPS cells respectively. The specific marker gene can be one that expresses optically visible proteins such as the green fluorescent protein or the "cherry" fluorescent protein described herein or an enzyme whose activity can be assayed, e.g. thymidine kinase.

In one embodiment, the stem cell cassette comprises only four genes selected from the group consisting of Oct4, Klf4, Sox2, Lin28, Nanog and c-Myc. In another embodiment, only three genes selected from the group consisting of Oct4, Klf4, Sox2, Lin28, Nanog and c-Myc, e.g. Oct4, Klf4, and Sox2; Oct4, Klf4, and c-Myc; or Oct4, Sox2 and Lin28. In these embodiments where only three genes are used, a specific marker gene takes the place of the fourth gene in the cassette.

Figure 1B:
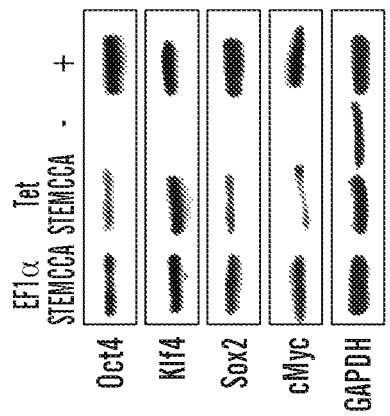
FIG. 1B shows the Western blot analysis of lysates from 293T transfected cells. Cells were transfected with pHAGE-Tet-STEMCCA and maintained in doxycycline for 72 hr before lysate preparation. Cells transfected with either mock vectors or four monocistronic pHAGE vectors encoding the four individual transcription factors were used as negative (−) or positive (+) controls, respectively.

The transcript elements in the recombinant lentiviral gene transfer plasmid comprising the stem cell cassette can be expressed constitutively or induced. For example, the inventors generated two forms of pHAGE-STEMCCA in which the multi-cistronic transcript is driven by either a constitutive EF1α promoter or a doxycycline (dox)-inducible TetO-miniCMV promoter. Both vectors resulted in the expression of all four individual proteins (OCT4, SOX2, KLF4, and c-MYC) as detected by western blot and immunohistochemistry (FIG. 1B and FIG. 1C).

Figure 2A:
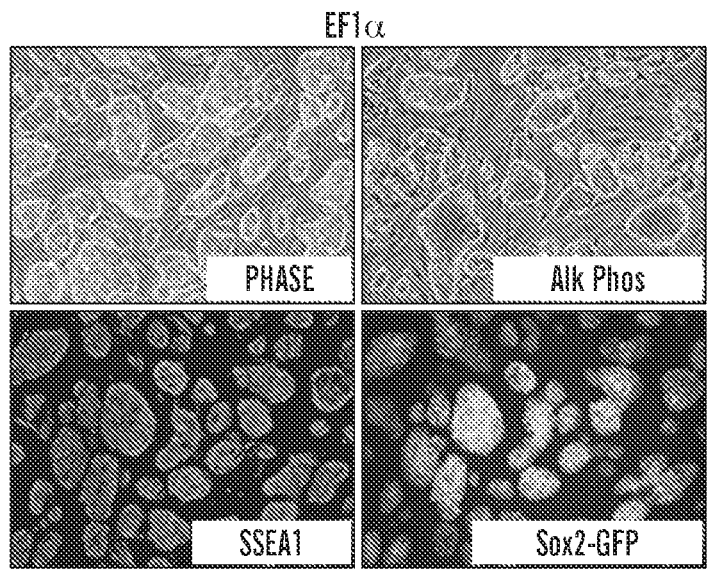
FIG. 2A shows representative pictures of iPS cells derived using the constitutive pHAGE-EF1α-STEMCCA: the colony morphology (Phase), high alkaline phosphatase activity (Alk Phos), SSEA1 immunostaining, and Sox2-GFP reporter gene expression.

The inventors tested the capacity of pHAGE-STEMCCA to derive iPS clones from mouse embryonic or post-natal fibroblasts. Due to the large size of the proviral genome of these vectors (>9 Kb), pHAGE-STEMCCA viral titers (2-3×$10^8$/ml) were lower than those obtained using mono-cistronic pHAGE vectors (5×$10^9$/ml). Nevertheless, mouse embryonic fibroblasts (MEFs) and tail-tip fibroblasts (TTFs) transduced with the constitutive EF1α STEMCCA construct showed a dramatic change in morphology already evident 6 days post-infection and formed colonies that were clonally expanded and displayed the typical morphology of ES cell colonies (FIG. 2A).

Figure 2B:
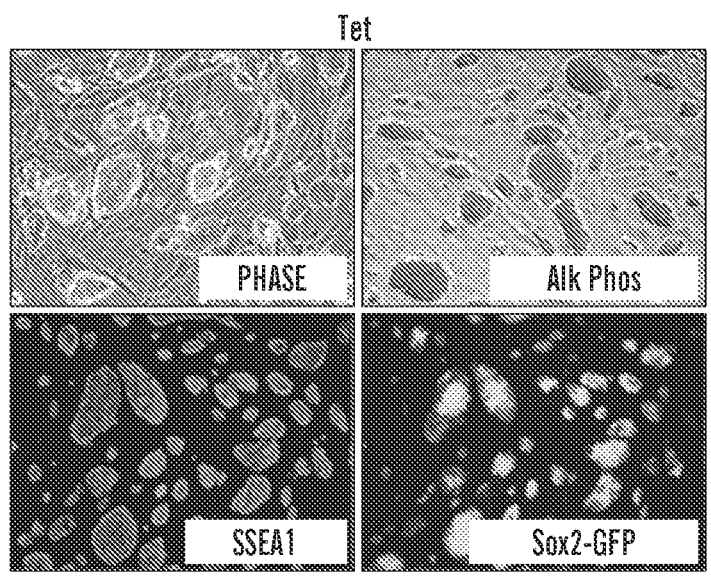
FIG. 2B shows representative pictures of iPS cells derived using the inducible pHAGE-Tet-STEMCCA vector: the colony morphology (Phase), high alkaline phosphatase activity (Alk Phos), SSEA1 immunostaining, and Sox2-GFP reporter gene expression.
Figure 2C:
FIG. 2C shows the expression of ES cell 'marker' genes detected by RT-PCR in four representative iPS cell clones generated by the constitutive (EF1α) or inducible (Tet) STEMCCA vector. Nat1 is a constitutively expressed gene and serves as a control for loading. Representative samples from unmanipulated mouse embryonic fibroblasts (MEF) and mouse ES cells are also shown. An iPS cell sample prepared without RT was used as negative control (−RT).
Figure 2D:
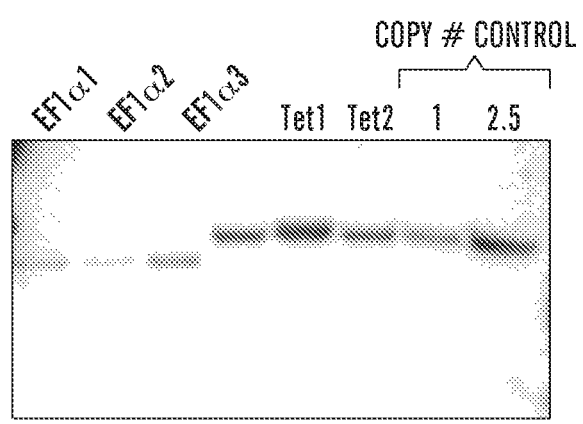
FIG. 2D shows the Southern blot analysis of genomic DNA (gDNA) purified from 6 representative iPS clones produced with the constitutive (EF1α) or inducible (tet) vector. gDNA was digested with BglII to obtain a band of 6.7 Kb in the EF1α colonies or 8.3 Kb in the Tet colonies, representing most of the proviral genome. For control, pHAGE-Tet-STEMCCA plasmid DNA representing 1 or 2.5 copies of the insert was digested with BglII. A single band of the expected size of the proviral gene insertion is present in all clones. The density of each band indicates between 1-3 proviral integrations in each clone.

For dox-inducible reprogramming, TTFs from a Sox2-GFP Rosa26-M2rtTA double knock-in mouse were transduced with pHAGE-STEMCCA that has a doxycycline (dox)-inducible TetO-miniCMV promoter. Cells from this mouse express rtTA constitutively and express GFP only upon activation of the Sox2 locus, which is silent in fibroblasts but active in ES cells. TTFs transduced with pHAGE-Tet-STEMCCA were exposed to doxycycline and changes in cell morphology were evident 6-8 days post induction with colonies appearing at day 12-14 (FIG. 2B). iPS colonies derived using either the constitutive (EF1α-) or inducible (Tet-) pHAGE-STEMCCA vector showed similarly positive alkaline phosphatase (AP) and stage-specific embryonic antigen 1(SSEA1) staining as well as consistent and strong GFP expression from the Sox2 locus (FIG. 2A and FIG. 2B). In addition, iPS clones generated with either vector expressed a variety of classic ES cell marker genes. These genes are not expressed in fibroblasts prior to reprogramming (FIG. 2C). Furthermore each iPS clone evidenced the correct transmission of the full lentiviral vector genome and contained only 1-3 integrated viral copies (FIG. 2D).

The inventors showed that the expression of this 'stem cell cassette' transcript in mouse fibroblasts accomplishes the efficient derivation of iPS cells with a single viral integration. Using the loxp/Cre technology, the integrated stem-cell cassette and viral genome were efficiently removed as shown in FIGS. 8C and 8D where the exogenous DNA was not detected by qRT-PCR and Southern Blots. The single non-integrating polycistronic lentiviral viral vector provides advances for the potential application of iPS technology in human clinical trials.

Reprogramming mediated by an Oct4-Klf4-Sox2-c-Myc stem-cell cassette containing lentiviral vector such pHAGE-STEMCCA recombinant lentiviral gene transfer plasmid offers several advances over existing multi-vector approaches. By using a single vector-based approach, the possibility to induce reprogramming with limited numbers of viral integrations can be achieved. One can obtain a uniform population of reprogrammed cells, i.e., one does not have to worry about only infecting a cell with 1, 2, or 3 genes encoding the transcription factors as opposed to all desired transcription factors, for example, Oct4-Klf4-Sox2-c-Myc, with a single infection. Indeed, the inventors were able to derive iPS clones with only a single integrated viral copy (FIG. 2D). This is in marked contrast to previous reports using multiple vectors, each with a different transcription factor, which required >15 viral integrations (Takahashi and Yamanaka, 2006, Cell 126, 663-676; Wernig et al., 2007, Nature 448, 318-324).

Accordingly, the present invention provides a vector system comprising: (a) a first vector containing a lentiviral gag gene encoding a lentiviral Gag protein, wherein the lentiviral gag gene is operably linked to a promoter and a polyadenylation sequence, (b) a second vector containing an env gene encoding a functional envelope protein, wherein the env gene is operably linked to a promoter and a polyadenylation sequence; (c) a lentiviral pol gene encoding a lentiviral Pol protein, wherein the pol protein is at least an integrase, and the pol gene is on the first or second vectors or on at least a third vector, wherein the lentiviral pol gene is operably linked to a promoter and a polyadenylation sequence; wherein the at least first, second and third vectors do not contain sufficient nucleotides to encode the lentiviral Gag and Pol and the envelope protein on a single vector; and wherein the vectors do not contain nucleotides of the lentiviral genome referred to as a packaging segment to effectively package lentiviral RNA; and wherein the lentiviral proteins and the envelope protein when expressed in combination form a lentivirus virion containing an envelope protein around a lentiviral capsid; and (d) a packaging gene transfer plasmid comprising a stem cell cassette nucleic acid sequence encoding: a Oct4 gene; a Klf4 gene; a Sox2 gene; a c-Myc gene; a first 'self-cleaving' 2A peptide; a second 'self-cleaving' 2A peptide; an internal ribosome entry site (IRES); wherein the nucleic acid sequence is operably linked to a promoter, wherein the sequences encoding Oct4, Klf4, Sox2, c-Myc, first and second 'self-cleaving' 2A peptides, and the IRES are transcribed from the promoter as a multi-cistronic RNA.

In one embodiment, the packaging gene transfer plasmid comprising a stem cell cassette nucleic acid sequence encoding: a first gene; a second gene; a third gene; an optional fourth gene; a first 'self-cleaving' 2A peptide; a second 'self-cleaving' 2A peptide; and an internal ribosome entry site (IRES); wherein the first, second, third and optional fourth genes are selected from the group consisting of Oct4, Klf4, Sox2, c-Myc, Lin28, and Nanog; and wherein the first, second, third and optional fourth genes are not identical; and wherein if the optional fourth gene is selected from the group consisting of Oct4, Klf4, Sox2, c-Myc, Lin28, and Nanog, a marker gene is included in its place, wherein the marker gene encodes an optically visible protein or an enzyme.

In one embodiment, the packaging gene transfer plasmid comprises a stem cell cassette nucleic acid sequence encoding four transcription factor genes selected from a group consisting of Oct4, Klf4, Sox2, c-Myc, Lin28 and Nanog; a first 'self-cleaving' 2A peptide; a second 'self-cleaving' 2A peptide; an internal ribosome entry site (IRES); wherein the nucleic acid sequence is operably linked to a promoter, wherein the sequences encoding the four transcription factor genes, first and second 'self-cleaving' 2A peptides, and the IRES are transcribed from the promoter as a multi-cistronic RNA.

In one embodiment, the packaging gene transfer plasmid comprises a stem cell cassette nucleic acid sequence encoding three transcription factor genes selected from a group consisting of Oct4, Klf4, Sox2, c-Myc, Lin28 and Nanog; a first 'self-cleaving' 2A peptide; a second 'self-cleaving' 2A peptide; an internal ribosome entry site (IRES); wherein the nucleic acid sequence is operably linked to a promoter, wherein the sequences encoding the three transcription factor genes, first and second 'self-cleaving' 2A peptides, and the IRES are transcribed from the promoter as a multi-cistronic RNA.

In one embodiment, the packaging gene transfer plasmid comprises a stem cell cassette nucleic acid sequence encoding: three transcription factor genes selected from a group consisting of Oct4, Klf4, Sox2, c-Myc, Lin28 and Nanog; a marker gene, a first 'self-cleaving' 2A peptide; a second 'self-cleaving' 2A peptide; an internal ribosome entry site (IRES); wherein the nucleic acid sequence is operably linked to a promoter, wherein the sequences encoding the three transcription factor genes, the marker gene, first and second 'self-cleaving' 2A peptides, and the IRES are transcribed from the promoter as a multi-cistronic RNA.

In one embodiment, the packaging gene transfer plasmid further comprises two Cre-LoxP sequences that flank the stem cell cassette nucleic acid sequence (see schematic design in FIG. 8A).

In one embodiment, the packaging gene transfer plasmid further comprises a Cre-ERT2 sequence. The Cre-ERT2 encodes a Cre recombinase (Cre) fused to a mutant estrogen ligand-binding domain (ERT2) that requires the presence of tamoxifen for activity. Excision of the integrated viral vector equipped with Cre-LoxP siets can be induced with the administration of tamoxifen.

In one embodiment, the integrase of the vector system has been modified so that it is not capable of integration.

In one embodiment, the vector system described herein comprises lentivirus selected from the group consisting of HIV, HIV-2, FIV, and SIV.

In one embodiment, the vector system described herein comprises lentivirus wherein the env gene encodes an envelope from a different virus, and is of a different source from the gag and pol genes.

In another embodiment, the present invention also provides a lentiviral vector particle capable for reprogramming a somatic cell to a stem-cell-like cell, the vector particle comprises a nucleic acid sequence comprising a sequence encoding: (a) a Oct4 gene; (b) a Klf4 gene; (c) a Sox2 gene; (d) a c-Myc gene; (e) a first 'self-cleaving' 2A peptide; (f) a second 'self-cleaving' 2A peptide; (g) an internal ribosome entry site (IRES); wherein the nucleic acid sequence is operably linked to a promoter, and wherein the sequences encoding the Oct4, Klf4, Sox2, c-Myc, first and second 'self-cleaving' 2A peptides, and the IRES are transcribed from the promoter as a multi-cistronic RNA.

In some embodiments, the nucleic acid sequence encodes a Nanog and/or Lin 28 gene.

In some embodiments, the nucleic acid sequence encodes several types of transcription factors sufficient to reprogram a somatic cell into an induced pluripotent stem cell that have the characteristics of a stem cell, for example having self renewal capability and/or expresses embryonic stem cell markers that are well known in the art and also described herein. The several types of transcription factors can be selected from the group consisting of OCT4, KLF4, SOX2, c-MYC, NANOG and LIN28. In some embodiments, at least three types of transcription factors are selected. Various combinations of transcription factors of OCT4, KLF4, SOX2, c-MYC, NANOG AND LIN 28 are contemplated. For example, OCT4, KLF4, SOX2, and c-MYC are selected and encoded in the nucleic acid sequence described herein.

In one embodiment, the present invention provides a lentiviral vector particle capable for reprogramming a somatic cell to a less differentiated state. This can range from a pluripotent stage to a relatively more differentiated stage. The key is that the cell is less differentiated than the original cell. In this manner one can reprogram cells to a desired state. The vector particle comprising a nucleic acid sequence comprising a sequence encoding: (a) a first gene; (b) a second gene; (c) a third gene; (d) an optional fourth gene; (e) a first 'self-cleaving' 2A peptide; (f) a second 'self-cleaving' 2A peptide; and (g) an internal ribosome entry site (IRES); wherein the first, second, third and optional fourth genes can be selected from the group consisting of Oct4, Klf4, Sox2, c-Myc, Lin28, and Nanog; wherein the first, second, third and optional fourth genes are not identical; wherein the nucleic acid sequence is operably linked to a promoter, wherein the sequences encoding the first, second, third and optional fourth genes, first and second 'self-cleaving' 2A peptides, and the IRES are transcribed from the promoter as a multi-cistronic RNA. Other combinations of reprogramming genes are knows and the present vector system can be used with any of them.

In some embodiments, if the fourth optional gene is not selected, a marker gene is included in its place, wherein the marker gene encodes an optically visible protein or an enzyme.

In some embodiments, alternate slice variants, functional conservative amino acid substitutions and truncations of these transcription factors are also contemplated (Atlasi Y., Stem Cells. 2008 Epub. September 11; A. E. F. Smith and K. G. Ford, Nucleic Acids Res. 2005, 33:6011-23; T. K. Nowling, J Biol Chem, 275: 3810-3818; Kit-Ling Sze, J. Cellular Physiology, 214:334-344). In some embodiments, family members of these transcription factors are used. For example, OCT4 is of the POU family of transcription factors. POU proteins are eukaryotic transcription factors containing a bipartite DNA binding domain referred to as the POU domain. The various members of the POU family have a wide variety of functions, all of which are related to the development of an organism. POU proteins are: POU1F1, POU2F1, POU2F2, POU2F3, POU3F1, POU3F2, POU3F3, POU3F4, POU4F1, POU4F2, POU4F3, POU5F1, POU6F1, and POU6F2.

In some embodiments, these transcription factor genes are derived from human. In other embodiments, these transcription factor genes are derived from other mammals such as mouse, rat, and also other organism such as the nematode worm *Caenorhabditis elegans*.

In one embodiment, the somatic cell is a mammalian cell. In one embodiment, the somatic cell is a mammalian cell derived from internal organs-heart, kidney, liver, lungs, bladder, intestines; skin, bones, blood, cartilage and connective tissues.

In one embodiment, the sequences encoding the four genes, e.g. Oct4, Klf4, Sox2, and c-Myc, in the lentiviral vector particle are arranged in tandem, wherein the genes are oriented in the sense direction, and wherein the genes are arranged in any order. This form a stem-cell-cassette. Some examples of tandem arrangement are Oct4-Klf4-Sox2-c-Myc, Oct4-Sox2-Klf4-c-Myc, Sox2-Klf4-Oct4-c-Myc, Klf4-Sox2-Oct4-c-Myc, and c-Myc-Sox2-Oct4-Klf4. Similarly, the sequences encoding the three transcription factor genes and a marker gene in the lentiviral vector particle are arranged in tandem, wherein the genes are oriented in the sense direction, and wherein the genes are arranged in any order. In all embodiments, the end of the 5' upstream (front) gene is fused to the beginning of the immediate downstream gene, thus the genes are oriented in the sense direction. Following transcription, a multi-cistronic mRNA can be translated to result in four individual proteins.

SOX2 is the human SRY (sex determining region Y)-box 2, (Genbank Accession No. BC013923; NM_003106.2; cDNA clone MGC:2413 IMAGE:2823424, SEQ. ID. No. 3). It is also known as ANOP3, MCOPS3, and MGC2413. This intronless gene encodes a member of the SRY-related HMG-box (SOX) family of transcription factors involved in the regulation of embryonic development and in the determination of cell fate. The product of this gene is required for stem-cell maintenance in the central nervous system, and also regulates gene expression in the stomach.

c-MYC is the human v-myc myelocytomatosis viral oncogene homolog (avian). It is also known as MYC and bHLHe39 (Genbank Accession No. NM_002467.3, SEQ. ID. No. 4). The protein is a multifunctional, nuclear phosphoprotein that plays a role in cell cycle progression, apoptosis and cellular transformation. It functions as a transcription factor that regulates transcription of specific target genes. Mutations, overexpression, rearrangement and translocation of this gene have been associated with a variety of hematopoietic tumors, leukemias and lymphomas, including Burkitt lymphoma.

KLF4 is the human Kruppel-like factor 4 (gut) (Genbank Accession No. NM_004235.4, SEQ. ID. No. 5). It is also known as EZF and GKLF. It is expressed transiently in certain mesenchymal cell and is an inhibitor of cell growth.

OCT4 is POU class 5 homeobox 1 (Genbank Accession No. NM_002701.4, SEQ. ID. No. 6; NM_203289.3, SEQ. ID. No. 7). It is also known as OCT3, OTF3, OTF4, POU5F1, and MGC22487.

NANOG is a transcription factor critically involved with self-renewal of undifferentiated embryonic stem cells. NANOG is a gene expressed in embryonic stem cells (ESCs) and is thought to be a key factor in maintaining pluripotency. NANOG is thought to function in concert with other factors such as POU5F1 and SOX2 to establish ESC identity. (Genbank Accession No. NM_024865, SEQ. ID. No. 47).

LIN28 is the human homolog of lin-28 of worms. It is also known as CSDD1; LIN-28; LIN28A; ZCCHC1; FLJ12457. (Genbank Accession No. NM_024674.4, SEQ. ID. No. 48).

In one embodiment, the sequence encoding an internal ribosome entry site (IRES) is between the second and third genes in the tandem arrangement of the four genes, e.g. Oct4, Klf4, Sox2, and c-Myc. However, other combinations are known in the art and are envisioned herein.

An internal ribosome entry site, abbreviated IRES, is a nucleotide sequence that allows for translation initiation in the middle of a messenger RNA (mRNA) sequence as part of the greater process of protein synthesis. Usually, in eukaryotes, translation can only be initiated at the 5' end of the mRNA molecule, since 5' cap recognition is required for the assembly of the initiation complex. IRES as cis-acting RNA sequences are able to mediate internal entry of the 40S ribosomal subunit on some eukaryotic and viral messenger RNAs upstream of a translation initiation codon. These sequences are very diverse and are present in a growing list of mRNAs. The IRES database is a comprehensive World Wide Web resource for internal ribosome entry sites and presents currently available general information as well as detailed data for each IRES. It is a searchable, periodically updated collection of IRES RNA sequences. Sequences are presented in FASTA form and hotlinked to NCBI GenBank files. Several subsets of data are classified according to the viral taxon (for viral IRESes), to the gene product function (for cellular IRESes), to the possible cellular regulation or to the trans-acting factor that mediates IRES function. This database is accessible at the World Wide Web site of "ifr31w3" "period" "Toulouse" "period" "inserm" "period" "fr" "/IRESdatabase/" and at the World Wide Web site of "rangueil" "period" "inserm" "period" "fr" "/IRESdatabase/".

Use of the IRES sequences are well known in the art. For example, in U.S. Pat. Nos. 4,937,190, 6,159,709, and 6,171,821. One skilled in the art would be able to search for known IRES sequences and incorporate an IRES element between the coding sequences of two genes. For example, the IRES sequence of encephalomyocarditis virus can be isolated from the LXIN retroviral vector, pLXIN vector, (Clontech, Palo Alto, Calif.) with restriction enzyme digestions, isolated and then inserted into the stem-cell-cassette described. Alternatively, commercial lentiviral vectors with IRES can be used. The coding sequences of the four genes: Oct4, Klf4, Sox2, and c-Myc can be inserted into these commercial lentiviral vectors. Examples of such commercial lentiviral vectors include but not limited to pReceiver-Lv31Lv32, -Lv33, -Lv35, -Lv36, -Lv40, -Lv43, -Lv44, and -Lv47 from Capital Biosciences, Inc., pLenti4/V5-DEST™, pLenti6/V5-DEST™, and pLenti6.2/V5-GW/lacZ (Invitrogen), and TREAutoR2 lentiviral vectors described in D. Markusic et. al. (Nucleic Acids Research 2005 33(6):e63).

In one embodiment, the sequence encoding the first 'self-cleaving' 2A peptide is between the first and second genes in the tandem arrangement of the four genes, e.g. Oct4, Klf4, Sox2, and c-Myc. In another embodiment, the sequence encoding the second 'self-cleaving' 2A peptide is between the third and fourth genes in the tandem arrangement the four genes, e.g. Oct4, Klf4, Sox2, and c-Myc.

The use of the 2A peptide in multi-cistronic constructs has emerged as an attractive alternative to the IRES. Like the IRES, the 2A peptide was identified among picornaviruses but in a different sub-group, the Aphthoviruses, a typical example of which is the Foot-and-mouth disease virus (Robertson B H, et. al., J Virol 1985, 54:651-660) 2A-like sequences have since been found in other Picornaviridae like the Equine rhinitis A virus, as well as unrelated viruses such as the Porcine teschovirus-1 and the insect Thosea asigna virus (TaV) (Donnelly M L, et. al., J. Gen. Virol. 2001, 82:1027-1041). In such viruses, multiple proteins are derived from a large polyprotein encoded by a single open reading frame. The 2A peptide mediates the co-translational cleavage of this polyprotein at a single site that forms the junction between the virus capsid and replication polyprotein domains.

The 2A sequences are relatively short peptides (of the order of 20 amino acids long, depending on the virus of origin) containing the consensus motif D-V/I-E-X-N-P-G-P (SEQ ID NO: 52; preferred embodiments disclosed as SEQ ID NOS 1-2). They were originally thought to mediate the autocatalytic proteolysis of the large polyprotein, but are now understood to act co-translationally, by preventing the formation of a normal peptide bond between the glycine and last proline, resulting in the ribosome skipping to the next codon (Donnelly M L, et. al., J Gen Virol 2001, 82:1013-1025) and the nascent peptide cleaving between the Gly and Pro. After cleavage, the short 2A peptide remains fused to the C-terminus of the 'upstream' protein, while the proline is added to the N-terminus of the 'downstream' protein. Based on highly inefficient peptide bond formation between Gly and Pro residues within the 2A peptide, placement of 2A peptide sequence as a linker region between tandem cDNA's, e.g. between Oct4 and Sox2, allows the stoichiometric translation of multiple unfused protein products.

Examples of self-processing peptides 2A peptides include but not limited to: F2A: VKQTLNNFDLLKLAGDVESN-PGP (SEQ. ID. No. 8), E2A: QCTNYALLKLAGDVESN-PGP (SEQ. ID. No. 9), T2A: EGRSLLTCGDVEENPGP (SEQ. ID. No. 10), and P2A: ATNFSLLKQAGDVEENPGP (SEQ. ID. No. 11)

In one embodiment, the coding sequence for a 2A peptide is 5' TGG GCC AGG ATT CTC CTC GAC GTC ACC GCA TGT TAG CAG ACT TCC TCT GCC CTC TCC ACT GCC 3' (SEQ. ID. No. 12).

In one embodiment, the first 'self-cleaving' 2A peptide between the first and second genes in the stem cell cassette is selected from the group consisting of F2A, E2A, T2A and P2A. In another embodiment, the second 'self-cleaving' 2A peptide between the third and fourth genes in the stem cell cassette is selected from the group consisting of F2A, E2A, T2A and P2A. In a further embodiment, the second 'self-cleaving' 2A peptide is different from the first 'self-cleaving' 2A peptide.

In one embodiment, the promoter for the described stem cell cassette is inducible. In one embodiment, the promoter is tetracycline regulated. In another embodiment, the promoter is a TetO/miniCMV promoter. The TetO/miniCMV promoter comprises the tetracycline-responsive transcriptional regulatory element of *Escherichia coli* (tetO) sequence linked to a minimal CMV promoter (miniCMV). The minimal CMV promoter is the core immediate early promoter of the human cytomegalovirus, in which the enhancer sites have been deleted. The TetO is bound by the Tet repressor protein (tetR) and gene transcription from the miniCMV promoter is blocked. The repression in relieved with tetracycline or its analogue such as doxycyclin. In the presence of tetracycline, the tetracylin repressor binds tetracycline, which binding displaces the repressor from the tetracycline operator sequence, so repression is relieved and transcription can begin. Construction of a TetO/miniCMV promoter vector is well known in the art, for example, in Bohl et al. (1998) Blood 92 (5): 1512-1517 and Haberman et al. (1998) Gene Ther. 5: 1604-1611. The tetracycline operator sequence is described by Baron U. et al., Nucleic acid research, Vol. 17, p. 3605-3606 (1995). The minimal CMV promoter construction and use are described in U.S. Pat. No. 6,368,825 and it is hereby incorporated by reference in its entirety.

In other embodiments, the promoter comprises hormone-responsive elements (HREs), metal-responsive elements (MREs), heat shock-responsive elements (HSREs), cytokine responsive elements or interferon-responsive elements (IREs) operably linked to a promoter, e.g. miniCMV. Expressions of genes operably linked to such promoters are induced in the presence of hormone, heavy metal, increases in temperature or interferon respectively. For example, a glucocorticoid-responsive element (GRE) is recognized and bound by the glucocorticoid/receptor complex and gene expression is induced. In some embodiments, the responsive elements comprise two or more responsive elements (see U.S. Pat. No. 5,877,018). Regulation of gene expression by hormone, heavy metal, temperature or interferon is well known in the art. One skilled in the art can incorporate the responsive element of choice into the construct of a lentiviral vector described herein. For example, the GRE consensus sequence is 5'-GATCTGGTACAGGATGTTCTAGCTACG-3' (SEQ. ID. No: 13) or MRE consensus sequence is 5'-GATCT-TGCGCCCGGCCCG-3' (SEQ. ID. No: 14). can be Other examples of inducible promoter are described in U.S. Patent Application 20050227285 and U.S. Pat. No. 5,877,018, and these references are hereby incorporated by reference in their entirety.

In one embodiment, the promoter for the described stem cell cassette is constitutive. In one embodiment, the promoter is EF-1alpha. In another embodiment, the promoter is beta-actin.

One of ordinary skill in the art can construct the stem cell cassette in a lentiviral vector. Conventional polymerase chain reaction (PCR) cloning techniques can be used to generate the isolated DNA sequence encoding three or four transcription factors, e.g. Oct4, Klf4, Sox2, and c-Myc. Ideally each PCR primer should have at least 15 nucleotides overlapping with its corresponding templates at the region to be amplified. The polymerase used in the PCR amplification should have high fidelity such as Strategene's PfuUltra™ polymerase for reducing sequence mistakes during the PCR amplification process. For ease of ligating the PCR amplified coding sequence to the leniviral vector, the PCR primers should also have distinct and unique restriction digestion sites on their flanking ends that do not anneal to the DNA template during PCR amplification. The choice of the restriction digestion sites for each pair of specific primers should be such that the coding nucleic acids are is in-frame and will encode the proteins OCT4, KLF4, SOX2, and c-MYC respectively from beginning to end with no stop codons. At the same time the chosen restriction digestion sites should not be found within the SEQ. ID. Nos.: 3-7, and SEQ. ID. Nos.:47-48.

In one embodiment, the primers Oct4 5' Nod 5' CACCG-GCGGCCGCCATGGATCCTCGAACCTG-GCTAAGCTTCCAAG-3' SEQ. ID. No. 15 and Oct4-F2A 3' 5'CTTGAGAAGGTCAAAATTCAAAGTCT-GTTTCACGCCACTTCCGTTTG AATGCATGG-GAGAGCCCAGAGCAG-3' SEQ. ID. No. 16 are used to PCR clone the cDNA of OCT4 from template SEQ. ID. No. 6 or SEQ. ID. No. 7. The primer Oct4 5' NotI has the restriction NotI site incorporated at its 5' end. The primer Oct4-F2A 3' has the coding sequence of F2A peptide at the 3' end. The PCR product has the restriction Nod site at the 5' end followed by the Oct4 and ending with the coding sequence of F2A peptide.

In one embodiment, the primers F2A-Klf4 5' 5'AAACA-GACTTTGAATTTTGACCTTCTCAAGTTG-GCGGGAGACGTGGAGTCCAACCCA GGGCCCATG-GCTAGCGACGCTCTGCTCCC-3' SEQ. ID. No. 17 and Klf4 3' BamHI 5' TTTGGATCCTTAAAAGTGCCTCT-TCATGTGTAAGGCAAG-3' SEQ. ID. No. 18 are used to PCR clone the cDNA of Klf4 from template SEQ. ID. No. 5. The primer Klf4 3' BamHI has the restriction BamHI site incorporated at its 3' end. The primer F2A-Klf4 5' has the coding sequence of F2A peptide at the 5' end. The PCR product has the coding sequence of F2A peptide at the 5' end followed by the Klf4 and ending with the restriction BamHI site at the 3' end.

In one embodiment, the fusion cistron comprising OCT4, FA2 and KLF4 arranged in tandem and oriented in the sense direction is constructed by PCR amplification of a mixture of the purified PCR products of the OCT4 PCR cloning reaction and the PCR products of the KLF4 PCR cloning reaction at a ratio of 1:1. The primers Oct4 5' NotI and Klf4 3' BamHI are used to PCR clone the chimeric DNA sequence comprising Oct4 at the 5' end followed by FA2 peptide and ending with Klf4. This PCR product is flanked by the restriction Nod site at the 5' and the restriction BamHI site at the 3' end. In one embodiment, this PCR product is digested with Nod and BamHI, and ligated into a previously NotI/BamHI digested lentiviral vector, e.g. pHAGE2, wherein the ligation is upstream of the IRES of the lentiviral vector.

In one embodiment, the primers Sox2 5' NdeI 5' GGTTTCTTACATATGATGTATAACAT-GATGGAGACGGAGCTGAAG-3' SEQ. ID. No. 19 and Sox2-E2A 3'TTTCAACATCGCCAGCGAGTTTCAA-CAAAGCGTAGTTAGTACATTGCCCACTACCCATG TGCGACAGGGGCAGTGTGCCGTTAATGGCCG-3' SEQ. ID. No. 20 are used to PCR clone the cDNA of Sox2 from template SEQ. ID. No. 3. The primer Sox2 5' NdeI has the restriction NdeI site incorporated at its 5' end. The primer Sox2-E2A 3' has the coding sequence of E2A peptide at the 3' end. The PCR product has the restriction NdeI site at the 5' end followed by the Sox2 and ending with the coding sequence of E2A peptide.

In one embodiment, the primers E2A-cMyc 5' 5'-CTTTGTTGAAACTCGCTGGCGATGT-TGAAAGTAACCCCGGTCCTATGCCCCTCAACGTG AACTTCACCAACAGGAACTATG-3' SEQ. ID. No. 21 and cMyc 3' ClaI 5GGTTTATCGATTTATGCACCA-GAGTTTCGAAGCTGTTC-3' SEQ. ID. No. 22 are used to PCR clone the cDNA of c-Myc from template SEQ. ID. No. 4. The primer E2A-cMyc 5' has the coding sequence of E2A peptide incorporated at its 5' end. The primer cMyc 3' ClaI has the restriction ClaI site at the 3' end. The PCR product has the coding sequence of E2A peptide at the 5' end followed by the c-Myc and ending with the restriction ClaI site.

In one embodiment, the fusion cistron comprising Sox2, EA2 and c-Myc that are arranged in tandem and oriented in the sense direction is constructed by PCR amplification of a mixture of the purified PCR products of the Sox2 PCR cloning reaction and the PCR products of the c-Myc PCR cloning reaction at a ratio of 1:1. The primers Sox2 5' NdeI and cMyc 3' ClaI are used to PCR clone the chimeric DNA sequence comprising Sox2 at the 5' end followed by EA2 peptide and ending with c-Myc. This PCR product is flanked by the restriction NdeI site at the 5' and the restriction ClaI site at the 3' end. In one embodiment, this PCR product is digested with NdeI and ClaI, and ligated into a previously NdeI/ClaI digested lentiviral vector, e.g. pHAGE2, wherein the ligation is downstream of IRES of the lentiviral vector.

In one embodiment, the primers E2A-mCherry 5' (5'-CTTTGTTGAAACTCGCTGGCGATGT-TGAAAGTAACCCCGGTCCTATGGTGAGCAAGGG CGAGGAGGATAACATGGCC-3' SEQ. ID. No. 41) and mCherry 3' ClaI (5'-ATCGATTTACTTGTACAGCTCGTC-CATGCCGCCGGTG-3' SEQ. ID. No. 42) are used to PCR clone the cDNA of the mCherry gene from the template GENBANK Accession No. AY678264 (SEQ. ID. No. 49) which codes for a monomeric red fluorescent protein gene. This gene is an engineered variant of monomeric red fluorescent protein mRFP1 in GENBANK Accession No. AF506027 (Shaner, N. C., et al., 2004, Nat. Biotechnol. 22:1567-1572). The primer E2A-mCherry 5' has the coding sequence of E2A peptide incorporated at its 5' end. The primer mCherry 3' ClaI has the restriction ClaI site at the 3' end. The PCR product has the coding sequence of E2A peptide at the 5' end followed by the mCHerry and ending with the restriction ClaI site.

In one embodiment, the nucleic acid sequence of the lentiviral gene transfer plasmid is pHAGE-Tet-STEMCCA (SEQ. ID. No. 23). This lentiviral gene transfer plasmid is also knows as pHAGE2-TetOminiCV-Oct4F2aK1f4-IRES-Sox2E2AcMyc-W.

In one embodiment, the nucleic acid sequence of the lentiviral gene transfer plasmid is pHAGE-EF1α-STEMCCA vector (SEQ. ID. No. 24). This lentiviral gene transfer plasmid is also knows as pHAGE2-EF1αFull-Oct4F2aK1f4-IRES-Sox2E2AcMyc-W.

In one embodiment, the nucleic acid sequence of the lentiviral gene transfer plasmid is pHAGE-EF1α-STEMCCA-LoxP-RedLight (SEQ. ID. No. 50). This lentiviral gene transfer plasmid is also knows as pHAGE-EF1α-STEMCCA-LoxP-RedLight or pHAGE2-EF1αFull-Oct4F2aK1f4-IRES-Sox2E2AmCherry-W-LoxP. This vector has the LoxP flanking the STEMCCA and the fourth gene in the cassette, c-Myc, has been replaced with a marker gene, mCherry, which codes for a red fluorescent protein.

Lentiviral vectors are a type of retrovirus that can infect both dividing and nondividing cells because their preintegration complex (virus "shell") can get through the intact membrane of the nucleus of the target cell. Lentiviruses can be used to provide highly effective gene therapy as lentiviruses can change the expression of their target cell's gene for up to six months. They can be used for nondividing or terminally differentiated cells such as neurons, macrophages, hematopoietic stem cells, retinal photoreceptors, and muscle and liver cells, cell types for which previous gene therapy methods could not be used. Examples of lentiviruses are human immunodeficiency virus (HIV) (strain 1 and strain 2), simian immunodeficiency virus (SIV), feline immunodeficiency virus (FIV), BLV, EIAV, CEV and visna virus. Of these, HIV and SIV are presently best understood. HIV is a very effective lentiviral vector. A vector containing such a lentivirus core (e.g. gag gene) can transduce both dividing and non dividing cells.

Recently, attention has focused on lentiviral vectors such as those based upon the primate lentiviruses, e.g., human immunodeficiency viruses (HIV) and simian immunodeficiency virus (SIV). HIV vectors can infect quiescent cells in addition to dividing cells. Moreover, by using a pseudotyped vector (i.e., one where an envelope protein from a different species is used), problems encountered with infecting a wide range of cell types can be overcome by selecting a particular envelope protein based upon the cell you want to infect. Moreover, in view of the complex gene splicing patterns seen in a lentiviruses such as HIV, multivalent vectors (i.e., those expressing multiple genes) having a lentiviral core, such as an HIV core, are expected to be more efficient. Despite the advantages that HIV based vectors offer, there is still a concern with the use of HIV vectors in view of the severity of HIV infection. Thus, means for providing additional attenuated forms that are less likely to revert to a wild type virus are desirable.

Variations can be made where multiple modifications are made, such as deleting nef, rev, vif and vpr genes. One can also have the 3' and 5' U3 deleted LTRs.

Lentiviruses are the only type of virus that is diploid; they have two strands of RNA. For example, HIV contains a diploid single stranded positive sense RNA-genome that is approximately 10 kb long. The ends are flanked with long terminal repeats (LTRs). A Psi-sequence is found near the 5' end of the RNA-genome which is necessary for packaging viral RNA into virus capsids to continue the infection of HIV in its host. However, the HIV's genetic information is integrated into the DNA of the host cell, so its RNA must be converted into DNA inside of the host for viral replication to be successful. This is done by reverse transcription of the RNA into DNA, and some of the proteins that are essential for this process. Reverse transcriptase synthesizes the first strand of DNA from the RNA template, and the host DNA polymerase synthesizes the second strand to produce dsDNA. Thus, quiescent cells do not have the ability to perform this second step in the reverse transcription process, so the RNA is not turned into DNA in cells in the G0 state. This is the reason for the limitation on gene therapy with HIV vectors. The DNA copy just made, which contains the genes gag, env, and pol, is inserted by integrase into the host genome. LTRs are also necessary for integration of the dsDNA into the host chromosome. LTRs also serve as part of the promoter for transcription of the viral genes. Thus, the virus is protected from attack by the immune system. It is this ability of the HIV to integrate its genetic material into a host cell which scientists would like to harness to put towards gene therapy. It has been shown that the HIV vector has an even higher rate of expression in its hosts cells than other retroviruses. HIV gene therapy vectors also do not trigger immune reactions, making them very attractive delivery systems.

The preintegration complex of the human immunodeficient virus (HIV), which allows the vector assess inside human cells, dividing or non-diving, is composed of the enzyme integrase, the product of the vpr gene (an accessory gene), and a protein encoded by the gag gene (an essential structural gene) called matrix. This matrix protein contains a localization sequence which is recognized by the import machinery of the nucleus of a cell. The virus is surrounded by a lipid bilayer with protruding membrane proteins. One of these proteins, gp120, is recognized by the host helper T cell CD4 receptor protein. Then HIV binds to a secondary receptor (CCR5 or CXCR4) and triggers a membrane fusion-mechanism with the gp41 transmembrane protein. This allows the virus asses to the cell interior and the virus content is released into the cytoplasm of the cell. Once inside of the cell in the cytoplasm, the matrix protein of the HIV contains a localization sequence that is recognized by the nuclear import machinery, which docks the complex at a nuclear membrane pore. This enables the preintegration complex of the HIV lentiviral vector to pass into the nucleus.

The lentiviral virion (particle) is expressed by a vector system encoding the necessary viral proteins to produce a virion (viral particle). Preferably, there is at least one vector containing a nucleic acid sequence encoding the lentiviral Pol proteins necessary for reverse transcription and integration, operably linked to a promoter. Preferably, the Pol proteins are expressed by multiple vectors. There is also a vector containing a nucleic acid sequence encoding the lentiviral Gag proteins necessary for forming a viral capsid operably linked to a promoter. In one embodiment, the gag-pol genes are on the same vector. Preferably, the gag nucleic acid sequence is on a separate vector than at least some of the pol nucleic acid sequence, still more preferably it is on a separate vector from all the pol nucleic acid sequences that encode Pol proteins.

In one embodiment, the gag sequence does not express a functional MA protein, i.e. the vector can still transduce cells in the absence of the entire MA or a portion thereof, if a myristylation anchor is provided. This can be accomplished by inactivating the "gene" encoding the MA by additions, substitutions or deletions of the MA coding region. Preferably, this is done by deletion. Preferably, at least 25% of the MA coding region is deleted, more preferably, at least 50% is deleted, still more preferably, at least 60%, even more preferably at least 75%, still more preferably, at least 90%, yet more preferably at least 95% and most preferably the entire coding region is deleted. However, in that embodiment, a myristylation anchor (sequence) is still required. Preferably, the myristylation sequence is a heterologous (i.e., non-lentiviral) sequence.

In another embodiment the lentiviral vector is another form of self-inactivating (SIN) vector as a result of a deletion in the 3' long terminal repeat region (LTR). Preferably, the vector contains a deletion within the viral promoter. The LTR of lentiviruses such as the HIV LTR contains a viral promoter. Although this promoter is relatively inefficient, when transactivated by e.g. tat, the promoter is efficient because tat-mediated transactivation increases the rate of transcription about 100 fold. However, the presence of the viral promoter can interfere with heterologous promoters operably linked to a transgene. To minimize such interference and better regulate the expression of transgenes, the lentiviral promoter is preferably deleted.

Preferably, the vector contains a deletion within the viral promoter. The viral promoter is in the U3 region of the 3' LTR. A preferred deletion is one that is 120 base pairs between Scal and Pvul sites, e.g. corresponding to nucleotides 9398-9518 of HIV-1 proviral clone HXB2, encompassing the essential core elements of the HIV-1 LTR promoter (TATA box, SP1 and NF-PB binding sites). After reverse transcription, the deletion is transferred to the 5' LTR, yielding a vector/provirus that is incapable of synthesizing vector transcripts from the 5' LTR in the next round of replication. Thus, the vector of the present invention contains no mechanism by which the virus can replicate as it cannot express the viral proteins.

In another embodiment the vector is a tat deleted vector. This can be accomplished by inactivating at least the first exon of tat by known techniques such as deleting it. Alternatively, one can extend the U3 LTR deletion into the R region to remove the TAR element.

Variations can be made where the lentiviral vector has multiple modifications as compared to a wildtype lentivirus. For example, with HIV being nef-, rev-, vpu-, vif- and vpr-. In addition one can have MA-gag, 3' and 5' U3 deleted LTR and variations thereof.

The vector(s) do not contain nucleotides from the lentiviral genome that package lentiviral RNA, referred to as the lentiviral packaging sequence. In HIV this region corresponds to the region between the 5' major splice donor and the gag gene initiation codon (nucleotides 301-319).

The env, gag and pol vector(s) forming the particle preferably do not contain a nucleic acid sequence from the lentiviral genome that expresses an envelope protein. Preferably, a separate vector contains a nucleic acid sequence encoding an envelope protein operably linked to a promoter is used. This env vector also does not contain a lentiviral packaging sequence. In one embodiment the env nucleic acid sequence encodes a lentiviral envelope protein.

In another embodiment the envelope protein is not from the lentivirus, but from a different virus. The resultant particle is referred to as a pseudotyped particle. By appropriate selection of envelopes one can "infect" virtually any cell. Thus, the vector can readily be targeted to a specific cell. For example, one can use an env gene that encodes an envelope protein that targets an endocytic compartment such as that of the influenza virus, VSV-G, alpha viruses (Semliki forest virus, Sindbis virus), arenaviruses (lymphocytic choriomeningitis virus), flaviviruses (tick-borne encephalitis virus, Dengue virus), rhabdoviruses (vesicular stomatitis virus, rabies virus), and orthomyxoviruses (influenza virus).

The preferred lentivirus is a primate lentivirus (U.S. Pat. No. 5,665,577) or a feline immunodeficiency virus (FIV) (Poeschla, E. M., et al., 1998, Nat. Medicine 4:354-357). The pol/gag nucleic acid segment(s) and the env nucleic acid segment will when expressed produce an empty lentiviral particle. By making the above-described modifications such as deleting the tat coding region, the MA coding region, or the U3 region of the LTR, the possibility of a reversion to a wild type virus has been reduced.

A desired family of heterologous nucleic acid segments (sometimes referred to as the target molecule) can be inserted into the empty lentiviral particles by use of a plurality of vectors each containing a nucleic acid segment of interest and a lentiviral packaging sequence necessary to package lentiviral RNA into the lentiviral particles (the packaging vector). Preferably, the packaging vector contains a 5' and 3' lentiviral LTR with the desired nucleic acid segment inserted between them. The nucleic acid segment can be antisense molecules or more preferably, encodes a protein such as an antibody. The packaging vector preferably contains a selectable marker gene. These are well known in the art and include genes that change the sensitivity of a cell to a stimulus such as a nutrient, an antibiotic, etc. Genes include those for neo (neomycin), puro (puromyicn), tk (thymidine kinase), multiple drug resistance (MDR), etc. Other genes express proteins that can readily be screened for such as green fluorescent protein (GFP), blue fluorescent protein (BFP), luciferase, LacZ, nerve growth factor receptor (NGFR), etc.

When an inducible promoter is used with the target molecule, minimal selection pressure is exerted on the transformed cells for those cells where the target molecule is "silenced". Thus, identification of cells displaying the marker also identifies cells that can express the target molecule. If an inducible promoter is not used, it is preferable to use a "forced-expression" system where the target molecule is linked to the selectable marker by use of an internal ribosome entry site (IRES) (see Marasco et al., PCT/US96/16531).

IRES sequences are known in the art and include those from encephalomycarditis virus (EMCV) (Ghattas, I. R. et al., 1991, Mol. Cell. Biol., 11: 5848-5849); BiP protein (Macejak and Sarnow, 1991, Nature, 353:91); the Antennapedia gene of *Drosophila* (exons d and e) (Oh et al., 1992, Genes & Dev., 6: 1643-1653); those in polio virus (Pelletier and Sonenberg, 1988, Nature 334:320325; see also Mountford and Smith, 1985, TIG, 11:179-184). Preferably, the target molecule is operably linked to an inducible promoter. Such systems allow the careful regulation of gene expression. See Miller, N. and Whelan, J., 1997, Human Gene Therapy, 8: 803-815). Such systems include those using the lac repressor from *E. coli* as a transcription modulator to regulate transcription from lac operator-bearing mammalian cell promoters (Brown, M. et al., 1987, Cell, 49:603-612) and those using the tetracycline repressor (tetR) (Gossen, M., and Bujard, H., Proc. Natl. Acad. Sci. USA, 1992, 89:5547-5551; Yao, F. et al., 1998, Human Gene Therapy, 9:1939-1950; Shockelt, P., et al., 1995, Proc. Natl. Acad. Sci. USA, 92:6522-6526). Other systems include FK506 dimer, VP16 or p65 using estradiol, RU486, diphenol murislerone or rapamycin [see Miller and Whelan, supra at FIG. 2]. Inducible systems are available from INVITROGEN, CLONTECH and ARIAD. Systems using a repressor with the operon are preferred. Regulation of transgene expression in target cells represents a critical aspect of gene therapy. For example, a lac repressor combined the tetracycline repressor (tetR) with the transcription activator (VP16) can be used to create a tetR-mammalian cell transcription activator fusion protein, tTa (tetR-VP16), with the tetO-bearing minimal promoter derived from the human cytomegalovirus (hCMV) major immediate-early promoter to create a tetR-tet operator system to control gene expression in mammalian cells. Recently Yao and colleagues (F. Yao et al., Human Gene Therapy, supra] demonstrated that the tetracycline repressor (tetR) alone, rather than the tetR-mammalian cell transcription factor fusion derivatives can function as potent trans-modulator to regulate gene expression in mammalian cells when the tetracycline operator is properly positioned downstream for the TATA element of the CMVIE promoter. One particular advantage of this tetracycline inducible switch is that it does not require the use of a tetracycline repressor-mammalian cells transactivator or repressor fusion protein, which in some instances can be toxic to cells (M. Gossen et al., 1992, Proc. Natl. Acad. Sci. USA, 89: 5547-5551; P. Shockett et al., 1995, Proc. Natl. Acad. Sci. USA, 92:6522-6526), to achieve its regulatable effects. Preferably, the repressor is linked to the target molecule by an IRES sequence. Preferably, the inducible system is a tetR system. More preferably the system has the tetracycline operator downstream of a promoter's TATA element such as with the CMVIE promoter.

The effectiveness of some inducible promoters increases over time. In such cases one can enhance the effectiveness of such systems by inserting multiple repressors in tandem, e.g. TetR linked to a TetR by an IRES. Alternatively, one can wait at least 3 days before screening for the desired function. While some silencing may occur, given the large number of cells being used, preferably at least $1\times10^4$, more preferably at least $1\times10^5$, still more preferably at least $1\times10^6$, and even more preferably at least $1\times10^7$, the effect of silencing is minimal. One can enhance expression of desired proteins by known means to enhance the effectiveness of the system. For example, using the Woodchuck Hepatitis Virus Port-transcriptional Regulatory Element (WPRC). See, Loeb, J. E., et al., 1999, Human Gene Therapy, 10:2295-2305; Zufferey, R., et al., 1999, J. of Virol., 73:2886-2892; Donello, J. E., et al., 1998, J. of Virol., 72:5085-5092).

In one embodiment, the stem cell cassette of the lentiviral gene transfer plasmid as described herein is flanked by LTRs and the Psi-sequence of HIV. The LTRs are necessary to integrate the therapeutic gene into the genome of the target cell, just as the LTRs in HIV integrate the dsDNA copy of the virus into its host chromosome. The Psi-sequence acts as a signal sequence and is necessary for packaging RNA with the reporter or therapeutic gene in virions. Viral proteins which make virus shells are provided in the packaging cell line, but are not in context of the LTRs and Psi-sequences and so are not packaged into virions. Thus, virus particles are produced that are replication deficient, so are designed to be unable to continue to infect their host after they deliver the coding sequences.

In one embodiment, the lentiviral vector described herein is flanked by loxP/Cre. Cre-lox allows site-specific recombination of DNA. There are other site-specific recombination sequences that can be used in an analgous manner. This is a tool that researchers use to site specifically knockout or overexpress specific genes in mice. CRE is a 38 kDa recombinase protein from bacteriophage P1 that mediates intra-molecular and inter-molecular site-specific recombination between loxP sites. A loxP site consists of two 13 bp inverted repeats separated by a 8 bp asymmetric spacer region. The detailed structure is given below.

```
                                              (SEQ. ID. No. 25)
       13 bp           8 bp        13 bp
      ATAACTTCGTATA-GCATACAT-TATACGAAGTTAT
```

One molecule of CRE binds per inverted repeat or two CRE molecules line up at one loxP site. The recombination occurs in the asymmetric spacer region. Those 8 bases are also responsible for the directionality of the site. Two loxP sequences in opposite orientation to each other invert the intervening piece of DNA; two sites in direct orientation dictate excision of the intervening DNA between the sites leaving one loxP site behind. This precise removal of DNA can be used to eliminate an endogenous gene or transgene (conditional gene deletion). The Cre/loxP system is a tool for tissue-specific (and, in connection with the tet system also time-specific) knockout or such genes that cannot be investigated in differentiated tissues because of their early embryonic lethality in mice with conventional knockouts. The Cre/loxP system can also be used to activate a transgene. The Cre's DNA excising capability can also be used to turn on a foreign gene by cutting out an intervening stop sequence between the promoter and the coding region of the transgene. The Cre/loxP system is well known in the art, such as in Zhongsen Li et al., Plant Molecular Biology, Vol. 65, No. 3, U.S. Pat. Nos. 5,919,676, 6,379,943, and 4,959,317 and these references are hereby incorporated by reference in their entirety. One of ordinary skill would be able to construct a lentiviral vector with Cre/loxP.

Lentiviral vectors are usually created in a transient transfection system in which a cell line is transfected with at least three separate plasmid expression systems. These include the transfer vector plasmid (portions of the HIV provirus), the packaging plasmid or construct, and a plasmid with the heterologous envelop gene (ENV) of a different virus. The three plasmid components of the vector are put into a packaging cell which is then inserted into the HIV shell. The virus portions of the vector contain insert sequences so that the virus cannot replicate inside the cell system.

The transfer vector plasmid contains cis-acting genetic sequences necessary for the vector to infect the target cell and for transfer of the genes (e.g. Oct4, Klf4, Sox2 and c-Myc) and contains restriction sites for insertion of desired genes. The 3' and 5' LTRs, the original envelop proteins, and gag sequence promoter have been removed.

In some embodiments, the transfer gene plasmid is pHAGE-Tet-STEMCCA vector (SEQ. ID. No. 23) pHAGE-EF1α-STEMCCA vector (SEQ. ID. No. 24) and pHAGE-EF1α-STEMCCA-LoxP-RedLight (SEQ. ID. No. 50). In SEQ. ID. No. 50, the LoxP flanks the STEMCCA and the fourth gene in the cassette, c-Myc, has been replaced with a marker gene, mCherry, which codes for a red fluorescent protein.

In some embodiments, commercially available lentiviral transfer gene plasmid are used, e.g. pLenti4/V5-DEST™, pLenti6/V5-DEST™ or pLenti vectors together with VIRAPOWER™ Lentiviral Expression systems from Invitrogen. Further examples include but limited to tetracycline-regulated replication-incompetent herpes simplex virus vectors described in F. Schmeisser, et al. (Human Gene Therapy, 2002, 13: 2113-2124) and the LTRCMVR2, LTRAutoR2, TRECMVR2 and TREAutoR2 lentiviral vectors described in D. Markusic et. al. (Nucleic Acids Research 2005 33(6):e63). The stem cell cassette can be constructed into these plasmids.

In other embodiments, the transfer vector plasmids are plasmids described in U.S. Pat. Nos. 6,521,457 and 6,277, 633. The stem cell cassette can be constructed into these plasmids.

The packaging plasmid is the backbone of the virus system. In this plasmid are found the elements required for vector packaging such as structural proteins, HIV genes (except the gene env which codes for infection of T cells, or the vector would only be able to infect these cells), and the enzymes that generate vector particles. Also contained is the human cytomegalovirus (hCMV) which is responsible for the expression of the virus proteins during translation. The packaging signals and their adjacent signals are removed so the parts responsible for packaging the viral DNA have been separated from the parts that activate them. Thus, the packaging sequences will not be incorporated into the viral genome and the virus will not reproduce after it has infected the host cell. Previous HIV vectors used two plasmids as the packaging plasmid contained the viral envelop gene. However, in the newer, better vectors the packaging plasmid lacks a viral envelop gene because this has been shown to be more desirable in terms of titer (minimum volume needed to cause a particular result in titration), stability, and broad range of target cells.

The third plasmid's envelope gene of a different virus specifies what type of cell to target and infect instead of the T cells. Normally HIV can infect only helper T-cells because they use their gp120 protein to bind to the CD4 receptor. However, it is possible to genetically exchange the CD4 receptor-binding protein for another protein that codes for the different cell type on which gene transfer will be performed. This gives the HIV lentiviral vector a broad range of possible target cells. There are two types of heterologous envelope proteins. The amphoteric envelop of MLV, another type of vector, is transcribed first followed by the transcription of the G glycoproteins of the vesicular stomatitis virus, known as VSV-G. Both of these help to provide stability to the vector by bringing together the particles that were made by the packaging plasmid.

The lentiviral virion (particle) is expressed by a vector system encoding the necessary viral proteins to produce a virion (viral particle). Preferably, there is at least one vector containing a nucleic acid sequence encoding the lentiviral pol proteins necessary for reverse transcription and integration, operably linked to a promoter. Preferably, the pol proteins are expressed by multiple vectors. There is also a vector containing a nucleic acid sequence encoding the lentiviral gag proteins necessary for forming a viral capsid operably linked to a promoter. Preferably, this gag nucleic acid sequence is on a separate vector than at least some of the pol nucleic acid sequence, still more preferably it is on a separate vector from all the pol nucleic acid sequences that encode pol proteins.

Numerous modifications can be made to the vectors, which are used to create the particles to further minimize the chance of obtaining wild type revertants. These include deletions of the U3 region of the LTR (for self inactivation), tat deletions and matrix (MA) deletions. Such modifications are well known in the art. One of ordinary skill in the art would be able to make these and similar modifications.

The gag, pol and env vector(s) do not contain nucleotides from the lentiviral genome that package lentiviral RNA, referred to as the lentiviral packaging sequence. In HIV this region corresponds to the region between the 5' major splice donor and the gag gene initiation codon (nucleotides 301-319).

In some aspects, the vector(s) forming the particle preferably do not contain a nucleic acid sequence from the lentiviral genome that expresses an envelope protein. Preferably, a separate vector that contains a nucleic acid sequence encoding an envelope protein operably linked to a promoter is used. This env vector also does not contain a lentiviral packaging sequence. In one embodiment the env nucleic acid sequence encodes a lentiviral envelope protein.

In another embodiment the envelope protein is not from the lentivirus, but from a different virus. The resultant particle is referred to as a pseudotyped particle. By appropriate selection of envelopes one can "infect" virtually any cell. For example, one can use an env gene that encodes an envelope protein that targets an endocytic compartment such as that of the influenza virus, VSV-G, alpha viruses (Semliki forest virus, Sindbis virus), arenaviruses (lymphocytic choriomeningitis virus), flaviviruses (tick-borne encephalitis virus, Dengue virus), rhabdoviruses (vesicular stomatitis virus, rabies virus), and orthomyxoviruses (influenza virus). Other envelopes that can preferably be used include those from Moloney Leukemia Virus such as MLV-E, MLV-A and GALV. These latter envelopes are particularly preferred where the host cell is a primary cell. Other envelope proteins can be selected depending upon the desired host cell. For example, targeting specific receptors such as dopamine receptor for brain delivery. Another target can be vascular endothelium. These cells can be targeted using a filovirus envelope. For example, the GP of Ebola, which by post-transcriptional modification become the GP1 and GP2 glycoproteins. In another embodiment, one can use different lentiviral capsids with a pseudotyped envelope. For example, FIV or SHIV (U.S. Pat. No. 5,654,195). A SHIV pseudotyped vector can readily be used in animal models such as monkeys.

The preferred lentivirus is a primate lentivirus (U.S. Pat. No. 5,665,577) or a feline immunodeficiency virus (FIV) (Poeschla, E. M., et al., 1998, Nat. Medicine 4:354-357). The pol/gag nucleic acid segment(s) and the env nucleic acid segment will when expressed produce an empty lentiviral particle. By making the above-described modifications such as deleting the tat coding region, the MA coding region, or the U3 region of the LTR, the possibility of a reversion to a wild type virus has been reduced to virtually nil.

In one embodiment, the lentiviral vector particle described herein is prepared according by a five-plasmid transfection procedure as described in following protocol: Trans-IT 293 transfection for lentivirus production for cationic liposomal transfection.

Reagents:
293-T cells 90% confluent—pass the day before
Trans-IT 293 from Mirus cat#Mir2700
DMEM high glucose
Complete media (e.g. for 293T cells use 10% FBS in high glucose DMEM with 1%
pen/strep and 1×L-glutamine (5 cc from a 200 mM stock)
DNA plasmids (backbone/insert, tat, rev, gag/pol, vsv-g)

| DNA proportions | | | | | |
| --- | --- | --- | --- | --- | --- |
| transfer vector | | | | | |
| 20 | 1 | 1 | 1 | 2 | |
| backbone | tat | rev | gag/pol | vsv-g | |
| 30 ug | 1.5 ug | 1.5 ug | 1.5 ug | 3 ug | = 37.5 ug total DNA |

Prepare trans-IT/DNA/media mix: 2 ml DMEM per 15 cm plate and 3 (ul) volumes of trans-IT per 1 ug of DNA (e.g for 1×15 cm2 plate that will receive 37.5 ug of DNA you need 3×37.5=112.5 ul of trans-IT in 2 ml of DMEM and 37.5 ug of DNA.

Protocol:
1. prepare 293T cells the day before in 15 cm plates
2. Prepare DNA in an eppendorf tube by mixing together the 5 plasmids in the proportions above
3. Put amount of trans-IT needed into plain DMEM (2 ml DMEM per 15 cm plate). Put the trans-IT directly into the media! Don't touch the walls of the container. Plastic de-activates the reagent. Drop wise while vortexing and let stand at RT for 10 min.
4. Add 37.5 ug DNA plasmid mix to the 2 ml of trans-IT/DMEM, drop wise while vortexing and let stand 15 min at RT.
5. Meanwhile take plate of 293T cells, aspirate off old media and pour 13 cc of complete media (e.g 10% FCS DMEM, etc) into each 15 cm plate.
6. Add the 2 ml of trans-IT/DNA/DMEM mix to each plate drop-wise
7. Mix gently by back and forth motion in two directions and incubate at 37° C.
8. Start collecting supernatants 48 hr after transfection (this is already the first collection, there is no need for washing), replace with 15 ml complete media and collect every 12 hours (4-5 collections). Use 0.45 um filter.
9. Concentrate by spinning for 1.5 hours at 16.5 k at 4° C. Discard all the supernatant and let sit on ice for 2 hr. Resuspend the virus in the liquid that came off the walls of the tube (approx. 180 ul per tube).
10. Aliquot and store at −80° C.

In some embodiments, the lentiviral vector particle described herein is prepared according to any methods known in the art, for example, U.S. Pat. Nos. 6,428,953, 6,566,513, 6,613,569, 6,790,657, 7,226,780, and 7,250,299. These references are hereby incorporated by reference in their entirety.

In some embodiments that commercially available lentiviral vectors are used, e.g. pLenti4/V5-DEST™, pLenti6/V5-DEST™ or pLenti vectors, the lentiviral vector particles are produced using the recommended lentiviral expression systems for that commercial lentiviral vector, e.g. with ViraPower™ Lentiviral Expression systems from Invitrogen.

Unless otherwise explained, all technical and scientific terms used herein have the same meaning as commonly understood by one of ordinary skill in the art to which this disclosure belongs. Definitions of common terms in molecular biology can be found in The Merck Manual of Diagnosis and Therapy, 18th Edition, published by Merck Research Laboratories, 2006 (ISBN 0-911910-18-2); Robert S. Porter et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8); The ELISA guidebook (Methods in molecular biology 149) by Crowther J. R. (2000); Fundamentals of RIA and Other Ligand Assays by Jeffrey Travis, 1979, Scientific Newsletters; Immunology by Werner Luttmann, published by Elsevier, 2006. Definitions of common terms in molecular biology can also be found in Benjamin Lewin, Genes IX, published by Jones & Bartlett Publishing, 2007 (ISBN-13: 9780763740634); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

Unless otherwise stated, the present invention was performed using standard procedures, as described, for example in Maniatis et al., Molecular Cloning: A Laboratory Manual, Cold Spring Harbor Laboratory Press, Cold Spring Harbor, N.Y., USA (1982); Sambrook et al., Molecular Cloning: A Laboratory Manual (2 ed.), Cold Spring Harbor Laboratory Press, Cold Spring Harbor, N.Y., USA (1989); Davis et al., Basic Methods in Molecular Biology, Elsevier Science Publishing, Inc., New York, USA (1986); or Methods in Enzymology: Guide to Molecular Cloning Techniques Vol. 152, S. L. Berger and A. R. Kimmerl Eds., Academic Press Inc., San Diego, USA (1987)), Current Protocols in Molecular Biology (CPMB) (Fred M. Ausubel, et al. ed., John Wiley and Sons, Inc.), Current Protocols in Protein Science (CPPS) (John E. Coligan, et. al., ed., John Wiley and Sons, Inc.) and Current Protocols in Immunology (CPI) (John E. Coligan, et. al., ed. John Wiley and Sons, Inc.), Current Protocols in Cell Biology (CPCB) (Juan S. Bonifacino et. al. ed., John Wiley and Sons, Inc.), Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998) which are all incorporated by reference herein in their entireties.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used in connection with percentages may mean+1%.

The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Application

In one embodiment, the present also provides a method of reprogramming a somatic cell; the method comprising contacting a somatic cell with a lentiviral vector described herein.

In one embodiment, the somatic cell is a mammalian cell. In one embodiment, the somatic cell is a mammalian cell derived from internal organs-heart, kidney, liver, lungs, bladder, intestines; skin, bones, blood, cartilage and connective tissues. One skilled in the art would be able to isolate somatic cells from an individual, culture expand the cells and infect these cells with a lentiviral vector particle described herein in vitro. The infected cells can then be analyzed for expression of embryonic stem (ES) cell markers, e.g. SSEAs, the transgene transcription factors such as OCT4, KLF4, SOX2, and c-MYC, or marker genes such as mCherry used herein etc, and for teratoma formation as described herein for confirmation of reprogramming of the somatic cell into a stem-cell-like cell.

In one embodiment, the method of programming somatic cells further comprises excising the integrated lentiviral vector after the infected cells demonstrate expression of embryonic stem (ES) cell markers, e.g. SSEAs, the transgene transcription factors such as OCT4, KLF4, SOX2, and c-MYC, or marker genes such as mCherry used herein. In one embodiment, the infected cells that have expressed embryonic stem (ES) cell markers, e.g. SSEAs, the transgene transcription factors such as OCT4, KLF4, SOX2, and c-MYC, or marker genes such as mCherry used herein are further infected with a defective Adenoviral vector carrying the Cre recombinase gene (Adeno-Cre). The excision is performed with a Cre recombinase. In one embodiment, the Cre is an inducible Cre, e.g. Cre-ERT2 which is induced by tamoxifen.

The present invention can be defined by any of the following alphabetized paragraphs:

[A] A lentiviral vector particle comprising a nucleic acid sequence comprising a sequence encoding: (a) a first gene; (b) a second gene; (c) a third gene; (d) an optional fourth gene, wherein the first, second, third and optional fourth genes are selected from the group consisting of Oct4, Klf4, Sox2, cMyc, Lin28, and Nanog, and wherein the first, second, third and optional fourth genes are not identical; (e) a first 'self-cleaving' 2A peptide; (f) a second 'self-cleaving' 2A peptide; and (g) an internal ribosome entry site (IRES); wherein the nucleic acid sequence is operably linked to a promoter, wherein the sequences encoding the first, second, third and optional fourth genes, first and second 'self-cleaving' 2A peptides, and the IRES are transcribed from the promoter as a multi-cistronic RNA.

[B] The lentiviral vector particle of paragraph [A], wherein a marker gene can be included, wherein the marker gene encodes an optically visible protein or an enzyme.

[C] The lentiviral vector particle of paragraph [A] or [B], wherein the sequences encoding the first, second, third and optional fourth genes are arranged in tandem, wherein the genes are oriented in the sense direction, and wherein the genes are arranged in any order.

[D] The lentiviral vector particle of any of paragraphs [A]-[C], wherein the sequence encoding internal ribosome entry site (IRES) is between the second and third genes in the tandem arrangement of the first, second, third and optional fourth genes.

[E] The lentiviral vector particle of any of paragraphs [A]-[D], wherein the sequence encoding the first 'self-cleaving' 2A peptide is between the first and second genes in the tandem arrangement of the first, second, third and optional fourth genes.

[F] The lentiviral vector particle of any of paragraphs [A]-[E], wherein the sequence encoding the second 'self-cleaving' 2A peptide is between the third and optional fourth genes in the tandem arrangement of the first, second, third and optional fourth genes.

[G] The lentiviral vector particle of paragraph [E], wherein the first 'self-cleaving' 2A peptide is selected from the group consisting of F2A, E2A, T2A and P2A.

[H] The lentiviral vector particle of paragraph [F] wherein the second 'self-cleaving' 2A peptide is selected from the group consisting of F2A, E2A, T2A and P2A.

[I] The lentiviral vector particle of any of paragraphs [A]-[H], wherein the second 'self-cleaving' 2A peptide is different from the first 'self-cleaving' 2A peptide.

[J] The lentiviral vector particle of any of paragraphs [A]-[I], wherein the promoter is inducible.

[K] The lentiviral vector particle of any of paragraphs [A]-[J], wherein the promoter is constitutive.

[L] The lentiviral vector particle of paragraph [J], wherein the promoter is tetracycline regulated.

[M] The lentiviral vector particle of paragraph [K], wherein the promoter is EF-1alpha.

[N] A lentiviral vector particle comprising a nucleic acid sequence comprising a sequence encoding: (a) a Oct4 gene; (b) a Klf4 gene; (c) a Sox2 gene; (d) a c-Myc gene; (e) a first 'self-cleaving' 2A peptide; (f) a second 'self-cleaving' 2A peptide; and (g) an internal ribosome entry site (IRES); wherein the nucleic acid sequence is operably linked to a promoter, wherein the sequences encoding Oct4, Klf4, Sox2, c-Myc, first and second 'self-cleaving' 2A peptides, and the IRES are transcribed from the promoter as a multi-cistronic RNA.

[O] The lentiviral vector particle of paragraph [N], wherein the sequences encoding the four genes: Oct4, Klf4, Sox2, and c-Myc, are arranged in tandem, wherein the genes are oriented in the sense direction, and wherein the genes are arranged in any order.

[P] The lentiviral vector particle of paragraph [N] or [0], wherein the sequence encoding internal ribosome entry site (IRES) is between the second and third genes in the tandem arrangement of the four genes: Oct4, Klf4, Sox2, and c-Myc.

[Q] The lentiviral vector particle of any of paragraphs [N]-[P] wherein the sequence encoding the first 'self-cleaving' 2A peptide is between the first and second genes in the tandem arrangement of the four genes: Oct4, Klf4, Sox2, and c-Myc.

[R] The lentiviral vector particle of any of paragraphs [N]-[Q], wherein the sequence encoding the second 'self-cleaving' 2A peptide is between the third and forth genes in the tandem arrangement of the four genes: Oct4, Klf4, Sox2, and c-Myc.

[S] The lentiviral vector particle of paragraph [Q], wherein the first 'self-cleaving' 2A peptide is selected from the group consisting of F2A, E2A, T2A and P2A.

[T] The lentiviral vector particle of paragraph [R] wherein the second 'self-cleaving' 2A peptide is selected from the group consisting of F2A, E2A, T2A and P2A.

[U] The lentiviral vector particle of any of paragraphs [N]-[T], wherein the second 'self-cleaving' 2A peptide is different from the first 'self-cleaving' 2A peptide.

[V] The lentiviral vector particle of any of paragraphs [N]-[U], wherein the promoter is inducible.

[W] The lentiviral vector particle of any of paragraphs [N]-[U], wherein the promoter is constitutive.

[Y] The lentiviral vector particle of paragraph [V], wherein the promoter is tetracycline regulated.

[Y] The lentiviral vector particle of paragraph [W], wherein the promoter is EF-1alpha.

[Z] A lentiviral vector particle capable for reprogramming a somatic cell to a stem-cell-like cell, the vector particle comprising a nucleic acid sequence comprising a sequence encoding: (a) a Oct4 gene; (b) a Klf4 gene; (c) a Sox2 gene; (d) a marker gene; (e) a first 'self-cleaving' 2A peptide; (f) a second 'self-cleaving' 2A peptide; and (g) an internal ribosome entry site (IRES), wherein the nucleic acid sequence is operably linked to a promoter, and wherein the sequences encoding Oct4, Klf4, Sox2, the marker gene, first and second 'self-cleaving' 2A peptides, and the IRES are transcribed from the promoter as a multi-cistronic RNA.

[AA] The lentiviral vector particle of paragraph [Z], wherein the marker gene encodes an optically visible protein or an enzyme.

[BB] The lentiviral vector particle of paragraph [Z] or [AA], wherein the sequences encoding the four genes: Oct4, Klf4, Sox2, and the marker gene, are arranged in tandem, wherein the genes are oriented in the sense direction, and wherein the genes are arranged in any order.

[CC] The lentiviral vector particle of any of paragraphs [Z]-[BB], wherein the sequence encoding internal ribosome entry site (IRES) is between the second and third genes in the tandem arrangement of the four genes: Oct4, Klf4, Sox2, and the marker gene.

[DD] The lentiviral vector particle of any of paragraphs [Z]-[CC], wherein the sequence encoding the first 'self-cleaving' 2A peptide is between the first and second genes in the tandem arrangement of the four genes: Oct4, Klf4, Sox2, and the marker gene.

[EE] The lentiviral vector particle of any of paragraphs [Z]-[DD], wherein the sequence encoding the second 'self-cleaving' 2A peptide is between the third and forth genes in the tandem arrangement of the four genes: Oct4, Klf4, Sox2, and the marker gene.

[FF] The lentiviral vector particle of any of paragraphs [A]-[EE] further comprises a Cre-LoxP excision sequence.

[GG] A vector system comprising: (a) a first vector containing a lentiviral gag gene encoding a lentiviral Gag protein, wherein the lentiviral gag gene is operably linked to a promoter and a polyadenylation sequence; (b) a second vector containing an env gene encoding a functional Env protein, wherein the env gene is operably linked to a promoter and a polyadenylation sequence; (c) a lentiviral pol gene encoding a lentiviral Pol protein, wherein the pol protein is at least an integrase, and the pol gene is on the first or second vectors or on at least a third vector, wherein the lentiviral pol gene is operably linked to a promoter and a polyadenylation sequence, wherein the at least first, second and third vectors do not contain sufficient nucleotides to encode the lentiviral Gag and Pol and the Env protein on a single vector, wherein the vectors do not contain nucleotides of the lentiviral genome referred to as a packaging segment to effectively package lentiviral RNA, and wherein the lentiviral proteins and the Env protein when expressed in combination form a lentivirus virion containing an Env protein around a lentiviral capsid; and (d) a packaging gene transfer plasmid comprising a stem cell cassette nucleic acid sequence encoding: a first gene; a second gene; a third gene; an optional fourth gene; a first 'self-cleaving' 2A peptide; a second 'self-cleaving' 2A peptide; and an internal ribosome entry site (IRES); wherein the first, second, third and optional fourth genes are selected from the group consisting of Oct4, Klf4, Sox2, c-Myc, Lin28, and Nanog; wherein the first, second, third and optional fourth genes are not identical; wherein if the optional fourth gene is not selected from the group consisting of Oct4, Klf4, Sox2, c-Myc, Lin28, and Nanog, a marker gene is included in its place, wherein the marker gene encodes an optically visible protein or an enzyme; wherein the nucleic acid sequence is operably linked to a promoter, and wherein the sequences encoding the first gene; the second gene; the third gene; the optional fourth gene, first and second 'self-cleaving' 2A peptides, and the IRES are transcribed from the promoter as a multi-cistronic RNA.

[HH] The vector system of paragraph [GG], wherein the integrase has been modified so that it is not capable of integration.

[II] The vector system of paragraph [GG] or [HH], wherein the lentivirus is selected from the group consisting of HIV, HIV-2, FIV, and SIV.

[JJ] The vector system of paragraph [GG], [HH] or [II], wherein the env gene encodes an envelope from a different virus, and is of a different source from the gag and pol genes.

[KK] The vector system of any of paragraphs [GG]-[JJ], wherein the sequences encoding the first, second, third and optional fourth genes are arranged in tandem, wherein the genes are oriented in the sense direction, and wherein the genes are arranged in any order.

[LL] The vector system of any of paragraphs [GG]-[KK], wherein the sequence encoding internal ribosome entry site (IRES) is between the second and third genes in the tandem arrangement of the first, second, third and optional fourth genes.

[MM] The vector system of any of paragraphs [GG]-[LL], wherein the sequence encoding the first 'self-cleaving' 2A peptide is between the first and second genes in the tandem arrangement of the first, second, third and optional fourth genes.

[NN] The vector system of any of paragraphs [GG]-[MM], wherein the sequence encoding the second 'self-cleaving' 2A peptide is between the third and forth genes in the tandem arrangement of the first, second, third and optional fourth genes.

[OO] The vector system of paragraph [MM], wherein the first 'self-cleaving' 2A peptide is selected from the group consisting of F2A, E2A, T2A and P2A.

[PP] The vector system of paragraph [NN], wherein the second 'self-cleaving' 2A peptide is selected from the group consisting of F2A, E2A, T2A and P2A.

[QQ] The vector system of any of paragraphs [GG]-[PP], wherein the second 'self-cleaving' 2A peptide is different from the first 'self-cleaving' 2A peptide.

[RR] The vector system of any of paragraphs [GG]-[QQ], wherein the promoter is inducible.

[SS] The vector system of any of paragraphs [GG]-[QQ], wherein the promoter is constitutive.

[TT] The vector system of paragraph [RR], wherein the promoter is tetracycline regulated.

[UU] The vector system of paragraph [SS], wherein the promoter is EF-1alpha.

[VV] A vector system comprising: (a) a first vector containing a lentiviral gag gene encoding a lentiviral Gag protein, wherein the lentiviral gag gene is operably linked to a promoter and a polyadenylation sequence, (b) a second vector containing an env gene encoding a functional envelope protein, wherein the env gene is operably linked to a promoter and a polyadenylation sequence; (c) a lentiviral pol gene encoding a lentiviral Pol protein, wherein the pol protein is at least an integrase, and the pol gene is on the first or second vectors or on at least a third vector, wherein the lentiviral pol gene is operably linked to a promoter and a polyadenylation sequence; wherein the at least first, second and third vectors do not contain sufficient nucleotides to encode the lentiviral Gag and Pol and the envelope protein on a single vector; and wherein the vectors do not contain nucleotides of the lentiviral genome referred to as a packaging segment to effectively package lentiviral RNA; and wherein the lentiviral proteins and the envelope protein when expressed in combination form a lentivirus virion containing an envelope protein around a lentiviral capsid; and (d) a packaging gene transfer plasmid comprising a stem cell cassette nucleic acid sequence encoding: a Oct4 gene; a Klf4 gene; a Sox2 gene; a c-Myc gene; a first 'self-cleaving' 2A peptide; a second 'self-cleaving' 2A peptide; an internal ribosome entry site (IRES), wherein the nucleic acid sequence is operably linked to a promoter, wherein the sequences encoding Oct4, Klf4, Sox2, c-Myc, first and second 'self-cleaving' 2A peptides, and the IRES are transcribed from the promoter as a multi-cistronic RNA.

[WW] The vector system of paragraph [VV], wherein the integrase has been modified so that it is not capable of integration.

[XX] The vector system of paragraph [VV] or [WW], wherein the lentivirus is selected from the group consisting of HIV, HIV-2, FIV, and SIV.

[YY] The vector system of paragraph [VV], [WW] or [XX], wherein the env gene encodes an envelope from a different virus, and is of a different source from the gag and pol genes.

[ZZ] The vector system of any of paragraphs [VV]-[YY], wherein the sequences encoding the four genes: Oct4, Klf4, Sox2, and c-Myc, are arranged in tandem, wherein the genes are oriented in the sense direction, and wherein the genes are arranged in any order.

[AAA] The vector system of any of paragraphs [VV]-[ZZ], wherein the sequence encoding internal ribosome entry site (IRES) is between the second and third genes in the tandem arrangement of the four genes: Oct4, Klf4, Sox2, and c-Myc.

[BBB] The vector system of any of paragraphs [VV]-[AAA], wherein the sequence encoding the first 'self-cleaving' 2A peptide is between the first and second genes in the tandem arrangement the four genes: Oct4, Klf4, Sox2, and c-Myc.

[CCC] The vector system of any of paragraphs [VV]-[BBB], wherein the sequence encoding the second 'self-cleaving' 2A peptide is between the third and forth genes in the tandem arrangement the four genes: Oct4, Klf4, Sox2, and c-Myc.

[DDD] The vector system of any of paragraphs [GG]-[CCC], wherein the sequence encoding cMyc is replaced by a marker gene, wherein the marker gene encodes an optically visible protein or an enzyme.

[EEE] The vector system of any of paragraphs [GG]-[DDD] further comprises a Cre-LoxP excision sequence.

[FFF] A method of reprogramming a somatic cell; the method comprising contacting a somatic cell with a lentiviral vector of any of paragraphs [A]-[EEE].

[GGG] An induced pluripotent stem cell derived by transduction of any lentiviral vector of any paragraphs [A]-[GGG].

This invention is further illustrated by the following example which should not be construed as limiting. The contents of all references cited throughout this application, as well as the figures and table are incorporated herein by reference.

EXAMPLES

Experimental Procedures

Construction of Lentiviral Vectors

A multiple expression system was designed based on the pHAGE lentiviral vector. pHAGE is a $3^{rd}$ generation lentiviral vector previously described (Mostoslaysky, G., et. al. 2006, Proc. Natl. Acad. Sci. USA 103:16406-16411). The pHAGE was re-engineered for multicistronic gene expression to accomplish the production of the proteins Oct4, Klf4, Sox2 and c-Myc from a single transcript. The templates used are Oct4: Genbank Accession No. NM_013633; Sox2: Genbank Accession No. NM_011443; Klf4: Genbank Accession No. NM_010637; cMyc: Genbank Accession No. NM_010849. First, two DNA fragments were generated by overlapping PCR using Pfu TURBO® DNA polymerase (STRATAGENE®); one fragment consisting of the complementary DNAs (cDNAs) of murine Oct4 and Klf4 separated by an intervening sequence encoding the F2A peptide, the second fragment containing the cDNAs of murine Sox2 and c-Myc, separated by an intervening sequence encoding the E2A peptide. To obtain the Oct4-F2A-Klf4 fragment, two PCR reactions were carried out using the primer pairs Oct4 5' NotI/Oct4-F2A 3' and F2A-Klf4 5'/Klf4 3' BglII (see Table 1) under the following conditions: initial denaturation at 94° C. for 2 min followed by 35 cycles of 45 s at 94° C., 45 s at 60° C. and 2 min at 72° C. Aliquots of the two purified amplicons were then mixed in a 1:1 ratio and used in a second PCR round with the primers Oct4 5' NotI and Klf4 3' BamHI under the following conditions: initial denaturation at 94° C. for 2 min, 5 cycles of 45 s at 94° C., 45 s at 58° C. and 2 min at 72° C., and 30 cycles of 45 s at 94° C., 45 s at 62° C. and 2 min at 72° C. The resulting fragment (Oct4-F2A-Klf4) was gel-purified and inserted by directional cloning into the Not I- and BamH I-digested pHAGE2 lentiviral vector backbone upstream of an IRES element. Similarly, a DNA fragment corresponding to Sox2-E2A-cMyc was obtained by PCR using the conditions described above and the primer pairs Sox2 5' NdeI/Sox2-E2A 3' and E2A-cMyc 5'/cMyc 3' ClaI (first round of amplification) and Sox2 5' NdeI/c-Myc 3' ClaI (second round of amplification). This fragment (Sox2-E2A-cMyc) was then inserted between the NdeI and ClaI sites, downstream of the IRES element of the pHAGE2-Oct4-F2A-Klf4 vector. Finally, the human EF1α promoter or the TetO/miniCMV promoter was cloned into SpeI and NotI sites of the recombinant vector to generate pHAGE-EF1α-STEMCCA and pHAGE-Tet-STEMCCA vectors, respectively. Sequence identity was confirmed by sequencing.

TABLE 1

| Primers used for vector construction. |  |
|---|---|
| Oct4 5' NotI | CACCGGCGGCCGCCATGGATCCTCGAACCTGGCT<br>AAGCTTCCAAG<br>(SEQ. ID. No. 15) |
| Oct4-F2A 3' | CTTGAGAAGGTCAAAATTCAAAGTCTGTTTCACG<br>CCACTTCCGTTTGAATGCATGGGAGAGCCCAGAG<br>CAG<br>(SEQ. ID. No. 16) |

TABLE 1-continued

Primers used for vector construction.

| | | |
|---|---|---|
| F2A-KIf4 5' | AAACAGACTTTGAATTTTGACCTTCTCAAGTTGG CGGGAGACGTGGAGTCCAACCCAGGGCCCATGGC TAGCGACGCTCTGCTCCC (SEQ. ID. No. 17) | |
| KIf4 3' Bam HI | TTTGGATCCTTAAAAGTGCCTCTTCATGTGTAAG GCAAG (SEQ. ID. No. 18) | |
| Sox2 5' NdeI | GGTTTCTTACATATGATGTATAACATGATGGAGA CGGAGCTGAAG (SEQ. ID. No. 19) | |
| Sox2-E2A 3' | TTTCAACATCGCCAGCGAGTTTCAACAAAGCGTA GTTAGTACATTGCCCACTACCCATGTGCGACAGG GGCAGTGTGCCGTTAATGGCCG (SEQ. ID. No. 20) | |
| E2A-cMyc 5' | CTTTGTTGAAACTCGCTGGCGATGTTGAAAGTAA CCCCGGTCCTATGCCCCTCAACGTGAACTTCACC AACAGGAACTATG (SEQ. ID. No. 21) | |
| cMyc 3' ClaI | GGTTTATCGATTTATGCACCAGAGTTTCGAAGCT GTTC (SEQ. ID. No. 22) | |

In order to obtain a foxed version of STEMCCA after viral integration, that would enable Cre-mediated excision of the vector following reprogramming, a 34-bp loxP site was inserted in the 3' dU3 LTR region of EF 1-STEMCCA. During reverse transcription, the loxP sequence is copied to the 5' LTR resulting in a vector flanked by two loxP sites.

Two versions of the constitutive EF1-STEMCCA vector described above were engineered, expressing either 4 reprogramming transcription factors (STEMCCA-loxP) or 3 reprogramming transcription factors plus mCherry (STEM-CCA-loxP-RedLight). A loxP site was introduced within the U3 region of the 3' LTR. Upon formation of the provirus a foxed version of each STEMCCA vector is produced. Following exposure to Cre, the entire cassette is excised. LTR: long terminal repeat; PSI: packaging signal; RRE: rev responsive element; cpPu: central polypuryne tract; WPRE: Woodchuck hepatitis virus post-transcriptional regulatory element; dU3: deleted U3.

Cell Culture

Tail-tip fibroblasts (TTFs) were derived from Sox2-GFP/R26-M2rtTA double knock-in mice (Stadtfeld, M., et. al., Cell Stem Cell 2:230-240) These cells carry an M2rtTA gene encoding a reverse tetracycline transactivator targeted to the constitutively active ROSA26 locus as well as a reporter cDNA targeted to the Sox2 locus. Tail snips from 3-4 day old mice were cultured according to standard methods to expand TTFs in fibroblast growth media (DMEM 10% FBS, L-Glutamine, penicillin/streptomycin). TTFs were infected at passage 3 for generation of iPS cells.

Lentivirus Production and Infection

Lentiviruses were produced using a five plasmid transfection system in 293T packaging cells as previously described (Mostoslaysky, G., et. al. 2006, Proc. Natl. Acad. Sci. USA 103:16406-16411). Generation of lentiviral vectors was accomplished by a five-plasmid transfection procedure. 293T cells were transfected using TransIT 293 (Minis, Madison, Wis.) according to the manufacturer instructions with the backbone pHAGE vector together with four expression vectors encoding the packaging proteins gagpol, rev, tat and the G-protein of the vesicular stomatitis virus (VSV). The gagpol helper plasmid has been codon-optimized for efficient mammalian expression and modified to severely reduce the homology with the gag sequences present in the vector packaging signal. In addition, it makes the gagpol expression rev-independent. All of the expression helper plasmids contain only the coding sequences, with minimal 5' or 3' untranslated sequences and no introns. In addition, the backbone contains the Woodchuck Hepatitis virus post-transcriptional regulatory element (WPRE), and the central polypurine tract (cppt) to enhance levels of transcription and gene expression. Viral supernatants were collected starting 24 hr after transfection, for four consecutive times every twelve hours, pooled and filtered through a 0.45 mm filter. Viral supernatants were then concentrated ~100 fold by ultracentrifugation in a Beckman centrifuge, for 1.5 hr at 16500 rpm and stored at −80° C.

Supernatants were collected every 12 hours during two consecutive days starting 48 hours after transfection and viral particles were concentrated by centrifugation at 16,500 rpm for 1.5 hours at 4° C. Approximately 100,000 fibroblasts were seeded on plastic in 35-mm culture plates and infected with 15-20 ml of concentrated virus in the presence of polybrene (5 μg/ml). The media was replaced after 16 hours with mouse ES cell media (DMEM supplemented with 15% FBS, L-glutamine, penicillin/streptomycin, nonessential amino acids, β-mercaptoethanol and 1000 U/ml LIF) and changed every 2-3 days. Doxycycline (Sigma-Aldrich) was added at a final concentration of 1 μg/ml, where indicated, and removed at day 10 post-infection. iPS colonies were picked 20 to 25 days post-infection based on morphology and GFP expression and expanded by plating on Mitomycin C treated MEFs in ES cell media.

iPS colonies were mechanically isolated 15 to 20 days post-infection with STEMCCA-loxP or 25-30 days post-infection with STEMCCA-loxP-RedLight based on morphology and expanded by plating on Mitomycin C treated MEFs in ES cell media.

Infection of iPS Cells with Adeno-Cre

Excision of STEMCCA was performed by infecting iPS cells with a defective adenoviral vector expressing Cre-recombinase (Adeno-Cre), a kind gift of Jeng-Shin Lee and Richard C. Mulligan from the Harvard Gene Therapy Initiative. The recombinant adenovirus was propagated in 293 cells, purified by CsCl gradient centrifugation and desalted on a Sephadex G-50 column (GE Healthcare UK Limited, Little Chalfont, Buckinghamshire, U.K.) in PBS/3% glycerol. For Adeno-Cre infection, iPS cells were tripsinized and washed once with PBS. Approximately 100,000 cells in 100 μl of ESC media were mixed with 3 μl of Adeno-Cre in a microfuge tube and incubated for 6 hours at 37° C. in a 5% $CO_2$ incubator. Cells were then washed with PBS, seeded on Mitomycin C treated MEFs and cultured in ESC media until colonies appeared. For each iPS clone infected with Adeno-Cre, several subclones were isolated and expanded as described above. Finally, the efficiency of Cre-recombinase activity was assessed by PCR and Southern Blot or by mCherry red fluorescence, as indicated in the text.

Antibodies

Immunofluorescence and western blot assays were performed using routine methods. The following primary antibodies were used: rabbit anti-Oct4 (Abcam), goat anti-Klf4 (R&D Systems), mouse anti-Sox2 (R&D Systems), mouse anti-cMyc (NeoMarkers), mouse anti-GAPDH (Millipore) and mouse anti-SSEA-1 (Santa Cruz Biotechnology). The following fluorochrome-conjugated secondary antibodies were applied: Alexa Fluor 488 donkey anti-goat, Texas Red goat anti-rabbit and Cy3 goat anti-mouse (Molecular Probes). Alkaline phosphatase staining was performed with the Vector Red Substrate Kit (Vector Laboratories) according to the manufacturer's instructions. Flow cytometry was performed using standard procedures. All flow cytometric data were acquired using equipment maintained by the Boston University Medical Campus Flow Cytometry Core Facility.

RT-PCR of Marker Genes

Total RNA was purified with TriPure Isolation Reagent (ROCHE®). One microgram of RNA was reverse-transcribed using ImProm-II Reverse Transcriptase (PROMEGA®) according to the manufacturer's instructions. Primers for ES cell marker genes are described elsewhere (Takahashi and Yamanaka, 2006, Cell 126, 663-676). The primers for ES cell marker genes, and names of the marker genes are listed below:

```
Oct3/4 (Pou5f1):
TCT TTC CAC CAG GCC CCC GGC TC); TGC GGG CGG ACA
TGG GGA GAT CC
(SEQ ID NOS 26 and 53, respectively, in order of
appearance)

Fgf4:
CGT GGT GAG CAT CTT CGG AGT GG; CCT TCT TGG TCC
GCC CGT TCT TA
(SEQ ID NOS 27 and 54, respectively, in order of
appearance)

Nanog:
CAG GTG TTT GAG GGT AGC TC; CGG TTC ATC ATG GTA
CAG TC
(SEQ ID NOS 28 and 55, respectively, in order of
appearance)

Rex1 (Zfp42):
ACG AGT GGC AGT TTC TTC TTG GGA; TAT GAC TCA CTT
CCA GGG GGC ACT
(SEQ ID NOS 29 and 56, respectively, in order of
appearance)

Esg1 (Dppa5):
GAA GTC TGG TTC CTT GGC AGG ATG; ACT CGA TAC ACT
GGC CTA GC
(SEQ ID NOS 30 and 57, respectively, in order of
appearance)

Gdf3:
GTT CCA ACC TGT GCC TCG CGT CTT; AGC GAG GCA TGG
AGA GAG CGG AGC AG
(SEQ ID NOS 31 and 58, respectively, in order of
appearance)

Ecat1:
TGT GGG GCC CTG AAA GGC GAG CTG AGA T; ATG GGC
CGC CAT ACG ACG ACG CTC AAC T
(SEQ ID NOS 32 and 59, respectively, in order of
appearance)

Dax1:
TGC TGC GGT CCA GGC CAT CAA GAG; GGG CAC TGT TCA
GTT CAG CGG ATC
(SEQ ID NOS 33 and 60, respectively, in order of
appearance)

Zfp296:
CCA TTA GGG GCC ATC ATC GCT TTC; CAC TGC TCA
CTG GAG GGG GCT TGC
(SEQ ID NOS 34 and 61, respectively, in order of
appearance)

Cripto:
ATG GAC GCA ACT GTG AAC ATG ATG TTC GCA; CTT
TGA GGT CCT GGT CCA TCA CGT GAC CAT
(SEQ ID NOS 35 and 62, respectively, in order of
appearance)

Nat1:
ATT CTT CGT TGT CAA GCC GCC AAA GTG GAG; AGT TGT
TTG CTG CGG AGT TGT CAT CTC GTC
(SEQ ID NOS 36 and 63, respectively, in order of
appearance)
```

Detection of the proviral DNA by PCR was carried out using 50 ng of genomic DNA and the primers endo-MycS (5'-ACGAGCACAAGCTCACCTCT-3' (SEQ. ID. No. 37)) and A-WPRE (5'-TCAGCAAACACAGTGCACACC-3' (SEQ. ID. No. 38)). PCR reactions consisted of 30 cycles of 95° C. for 30 seconds, 65° C. for 45 seconds and 72° C. for 45 seconds.

To create a LoxP site, complementary 5'-phosphorilated oligonucleotides containing a loxP sequence flanked by overhang sites for AscI (5'-/5Phos/CGCGCAGGTACCATAACT-TCGTATAATGTATGCTATACGAAGTTATGG-3' (SEQ. ID. No. 39)) and 5'-/5Phos/CGCGCCATAACTTCGTATAG-CATACATTATACGAAGTTATGGTACCTG-3' (SEQ. ID. No. 40)) were annealed and ligated to the vector previously digested with the same enzyme to create STEMCCA-loxP. The STEMCCA-loxP-RedLight vector was constructed as follows. A PCR product consisting of the murine Sox2 gene and the mCherry gene separated by an intervening sequence encoding the E2A peptide was generated by overlapping PCR using Pfu TURBO® DNA polymerase (STRATAGENE®). In brief, two PCR reactions were carried out with primer pairs Sox2 5'NdeI/Sox2-E2A 3' and E2A-mCherry 5'/mCherry 3'ClaI under the following conditions: initial denaturation at 95° C. for 2 min followed by 35 cycles of 45 s at 95° C., 45 s at 60° C. and 2 min at 72° C. Aliquots of the two purified amplicons were then mixed in a 1:1 ratio and used in a second PCR round with the primers Sox2 5 ' NdeI and mCherry 3' ClaI under the following conditions: initial denaturation at 95° C. for 2 min, 5 cycles of 45 s at 95° C., 45 s at 58° C. and 2 min at 72° C., and 30 cycles of 45 s at 95° C., 45 s at 62° C. and 2 min at 72° C. The resulting fragment Sox2-E2A-mCherry was gel-purified and inserted by directional cloning into the Nde I- and Cla I-digested STEMCCA-loxP vector. Sequence identity was confirmed by sequencing. Primer sequences were as follows: Sox2 5' NdeI (5'-GGTTTCTTA-CATATGATGTATAACATGATGGAGACG-GAGCTGAAG-3' (SEQ. ID. No. 19)), Sox2-E2A 3' (5'-TTTCAACATCGCCAGCGAGTTTCAACAAAGCGTA-GTTAGTACATTGCCCACTACCCATG TGCGA-CAGGGGCAGTGTGCCGTTAATGGCCG-3' SEQ. ID. No. 20), E2A-mCherry 5' (5'-CTTTGTTGAAACTCGCTGGC-GATGTTGAAAGTAACCCCGGTCCTATG-GTGAGCAAGGG CGAGGAGGATAACATGGCC-3' SEQ. ID. No. 41), mCherry 3'ClaI (5'-ATCGATTTACTTGTA-CAGCTCGTCCATGCCGCCGGTG-3' SEQ. ID. No. 42).

Quantitative RT-PCR qRT-PCR for STEMCCA transcript was carried out in a StepOnePlus real-time PCR system (APPLIED BIOSYS-TEMS®) using Taqman custom primers and probe specific to the genes of interest as described by the manufacturer. Amplification of the viral transcript was performed with a Taqman assay designed to amplify a cMyc to WPRE fragment present in the STEMCCA vector. Reactions were performed in triplicate using 1/20 of the cDNA obtained as described above. Gene expression levels were normalized to-actin and relative quantification of expression was estimated using the comparative Ct method. For qRT-PCR analyses of changes in gene expression in response to activin A stimulation, total RNA was purified with RNeasy Mini kit (QIAGEN®) and treated with RNase-Free DNase I (QIAGEN®). One microgram of RNA was reverse-transcribed using TaqMan Reverse Transcription Reagents kit (APPLIED BIOSYSTEMS®) according to the manufacturer's instructions. qPCR analyses of cDNAs was performed in an APPLIED BIOSYSTEMS® Sequence Detection System 7300 using the following Taqman inventoried primers and probes (APPLIED BIOSYSTEMS®): Nanog (Mm02384862_g1), Rex1 (Mm01194089_g1), Brachyury (Mm00436877_ml), FoxA2 (Mm00839704_mH), Sox17 (Mm004883 63_m1), Gata4 (Mm00484689_m1), and Gata6 (Mm0080263 6_m1). Reactions were performed in duplicate using 1/20 diluted cDNA obtained as described above. Gene expression levels were normalized to 18S rRNA (4319413E) and relative expression of each gene compared to undifferentiated ESC was quantified using the $2^{-[delta][delta]Ct}$ method.

Bisulfite Sequencing

Bisulfite modification of genomic DNA (2 g) was carried out using the EpiTect Bisulfite Kit (QIAGEN®) following the protocol recommended by the manufacturer. A region of the Nanog promoter was amplified by hot-start PCR as previously described in Takahashi K, and Yamanaka S., Cell. 2006; 126:663-676. The Oct4 promoter was amplified by nested—PCR. Initial PCR was done with the primers 5'-GTAAGTAA-GAATTGAGGAGTGG-3' (SEQ. ID. No. 43) and 5'-TC-CAAACCCACCTAAAAACC-3' (SEQ. ID. No. 44) under the following conditions: 95° C. for 3 min, 30 cycles of 95° C. for 1 min, 56° C. for 1 min and 72° C. for 1 min, and a final extension cycle at 72° C. for 10 min. PCR products were purified with the QIAquick PCR Purification Kit (QIAGEN®) and 51 were used as a template for the second PCR using the primers 5'-GATGGTTGAGTGGGTTG-TAAGG-3' (SEQ. ID. No. 45) and 5'-CCAACCCTACTAAC-CCATCACC-3'(SEQ. ID. No. 46) and the conditions described above. Finally, purified PCR products were cloned into pGEM-T vector (PROMEGA®) and sequenced with the T7 promoter primer.

Alkaline Phosphatase Staining and Immunofluorescence

Alkaline phosphatase staining was performed with the Vector Red Substrate Kit (Vector Laboratories, Burlingame, Calif.) according to the manufacturer's protocol. For immunofluorescence, cells were fixed in 4% paraformaldehyde for 5 min, washed twice with PBS and incubated with mouse anti-SSEA-1 (Santa Cruz Biotechnology, Santa Cruz, Calif.) in PBS/5% goat serum for 30 min at 4° C. Secondary antibody staining was performed similarly using ALEXA® Fluor 568 goat anti-mouse IgM (INVITROGEN™, Inc.).

ES and iPS Cell Differentiation

Prior to differentiation all ESC and iPS cells were adapted to serum-free maintenance media (Gouon-Evans V, et al., Nat. Biotechnol. 2006; 24:1402-1411) by culture expansion on mitomycin C-inactivated mouse embryonic fibroblasts (MEFs). Maintenance media consisted of 50% Neurobasal medium (INVITROGEN™, Inc.) and 50% Dulbecco's Modified Eagle Medium/F12 medium (INVITROGEN™, Inc.); with N2 and B27 supplements (INVITROGEN™, Inc.), 1% penicillin/streptomycin, 0.05% bovine serum albumin, LIF (1000 U/ml; ESGRO; Chemicon; MILLIPORE®, Bedford, Mass.), 10 ng/ml human BMP-4 (R&D Systems), and 1.5 10-4 M monothioglycerol (MTG) (SIGMA-ALDRICH®). Mouse ESC (129/Ola; containing GFP targeted to the brachyury locus and hCD4 targeted to the Foxa2 locus) were the generous gift of Dr. Gordon Keller, Mount Sinai Medical Center, New York, N.Y. (Gouon-Evans V, et al., Nat. Biotechnol. 2006; 24:1402-1411; Gadue P, et al., Exp. Hematol. 2005; 33:955-964). Differentiation into primitive streakand endoderm-like phenotypes was performed in serum free media, as previously described by Keller and colleagues (Gouon-Evans V., et al. and Gadue P, et al. supra). Briefly, embryoid bodies were formed in suspension culture by plating ESC or iPS cells in non-adherent culture plates for 2 days in the absence of LIF. On day 2 embryoid bodies were dispersed by trypsinization followed by replating for 3 more days in serum-free media with activin A (50 ng/ml; R&D systems, 338-AC). On day 5 embryoid bodies were dissociated with trypsin/EDTA (2 min, 37° C.) and harvested for RNA extraction.

Teratoma Formation

One million iPS cells were injected subcutaneously into each flank of recipient NOD/SCID mice (Jackson Labs). The procedure was approved by Paraffin sections of formalin-fixed teratoma specimens were prepared 3-5 weeks after injection, and analysis of H and E stained tissue sections was performed for each specimen. All animal experiments were performed in accordance with Boston University Institutional Animal Care and Use Committee (IACUC).

Southern Blot

Southern blot analysis using standard methods was performed on DNA digested with BglII (New England Biolabs, MA) that cuts once in each of the two viral LTRs, in order to estimate the proviral copy number per genome. In the Tet-STEMCCA vector a 8.3 kb band is expected. Because the EF1α promoter contains a BglII site, a smaller band of 6.7 Kb is expected. Woodchuck Hepatitis virus post-transcriptional regulatory element (WPRE), a genomic fragment that enhances RNA export from the nucleus to the cytoplasm and therefore enhances viral titers during production. A WPRE fragment that recognizes all our constructs was used as a probe.

Generation of Chimeric Animals

Superovulation of C57BL/6J-Tyrc-2J donor females (The Jackson Laboratory) was induced by injection of 5 IU PMS followed by 5 IU HCG 48 hours later. Female donors were immediately mated to stud males and checked for vaginal plug formation the following day. Zygotes were collected from the oviduct and cultured in KSOM media. Blastocysts were identified and injected with iPS cells before being surgically transferred to uteri of pseudopregnant females. Pregnant mice were sacrificed at day E11.5 and whole embryos were photographed with an inverted fluorescence microscope. Chimeric experiments were performed by the Transgenic Center Core of Boston University School of Medicine.

Karyotyping and SKY Analysis

Metaphase spreads were prepared according to standard protocols (Franco S, Mol. Cell. 2006; 21:201-214). Spectral karyotyping was performed with a mouse SKY paint kit (Applied Spectral Imaging Inc., Vista, Calif.) according to the manufacturer's instructions. Images were acquired with BX61 Microscope (Olympus, Tokyo) equipped with a motorized automatic stage, a cooled CCD camera and an interferometer (Applied Spectral Imaging). 63× objective was used. Analysis was performed with the HiSKY and ScanView softwares (Applied Spectral Imaging).

Example 1

A Single Lentiviral Vector for the Expression of a Stem Cell Cassette

Previous studies have developed multicistronic lentiviral vectors based on a combination of an IRES element and 2A peptide sequences (Szymczak et al., 2004, Nat Biotechnol 22, 589-594) to express multiple genes simultaneously from a single lentiviral vector (Chinnasamy et al., 2006, Virol. J. 3:14). Using a similar approach a single lentiviral transfer gene plasmid was designed expressing a "STEM-Cell Cassette", (hereafter pHAGE-STEMCCA). This cassette is comprised of a single multicistronic mRNA containing an IRES element separating two fusion cistrons. The two cistrons consist of Oct4 and Sox2 coding sequences fused to Klf4 and c-Myc, respectively, through the use of intervening sequences encoding 'self-cleaving' 2A peptides (FIG. 1A). Two forms of pHAGE-STEMCCA were generated, wherein the multicistronic transcript is driven by either a constitutive EF1α promoter or a doxycycline (dox)-inducible TetO-miniCMV promoter. Both vectors resulted in the expression of all four individual proteins (OCT4, KLF4, SOX2, and c-MYC) as detected by western blot analysis and immunohistochemistry (FIG. 1B. and data not shown). The immunofluorescence microscopy of MEFs infected 4 days earlier with pHAGE-EF1α-STEMCCA shows expression of all four transcription factors. Uninfected MEFs or secondary antibody only staining control showed no detectable staining.

The schematic plasmid map for pHAGE-EF1α-STEMCCA for constitutive expression of the four Oct4, Klf4, Sox2, and c-Myc transgenes is shown in FIG. 7 and the DNA sequence of the plasmid is SEQ. ID. No. 24.

The schematic plasmid map for pHAGE-Tet-STEMCCA for tet inducible expression of the four Oct4, Klf4, Sox2, and c-Myc transgenes is shown in FIG. 6 and the DNA sequence of the plasmid is SEQ. ID. No. 23.

Generation of iPS Cells with a Single Lentiviral Vector

Next, the capacity of pHAGE-STEMCCA to derive iPS clones from mouse embryonic or post-natal fibroblasts was assessed. As expected from the large size of the proviral genome of these plasmids (>9 Kb), pHAGE-STEMCCA viral titers ($2-3\times10^8$/ml) were lower than those obtained using monocistronic pHAGE plasmids ($5\times10^9$/ml). Nevertheless, mouse embryonic fibroblasts (MEFs) and tail-tip fibroblasts (TTFs) transduced with the constitutive EF1α STEMCCA construct showed a dramatic change in morphology already evident 6 days post-infection and formed colonies that were clonally expanded and displayed the typical morphology of ES cell colonies (FIG. 2A).

For the generation of iPS cells with the dox-inducible construct, the TTFs that was transduced was from a Sox2-GFP Rosa26-M2rtTA double knock-in mouse in which the rtTA is constitutively expressed but the Sox2-GFP allele is largely repressed. TTFs transduced with the inducible pHAGE-STEMCCA were exposed to doxycycline and changes in cell morphology were evident 6-8 days post induction with colonies appearing at day 12-14 (FIG. 2B). iPS colonies derived using either the constitutive (EF1α) or inducible (Tet) pHAGE-STEMCCA vector showed comparable alkaline phosphatase (AP) and SSEA1 staining as well as consistent and strong GFP expression from the Sox2 locus, indicating reactivation of a crucial ES cell marker (FIGS. 2A and 2B). In addition, iPS clones generated with either vector expressed a variety of other classic ES cell marker genes (FIG. 2C) while these genes were not expressed in fibroblasts prior to reprogramming. Furthermore, each iPS clone showed the correct transmission of the full lentiviral vector genome as analyzed by Southern blot and contained only 1-3 integrated viral copies (FIG. 2D). Expression of the STEMCCA mRNA transcript was determined in vitro in iPS cells in the absence of doxycycline. As expected, transcript expression was found to be higher in iPS clones generated with the constitutively expressing vector compared to those generated with the dox-inducible vector (FIG. 5).

Figure 3:
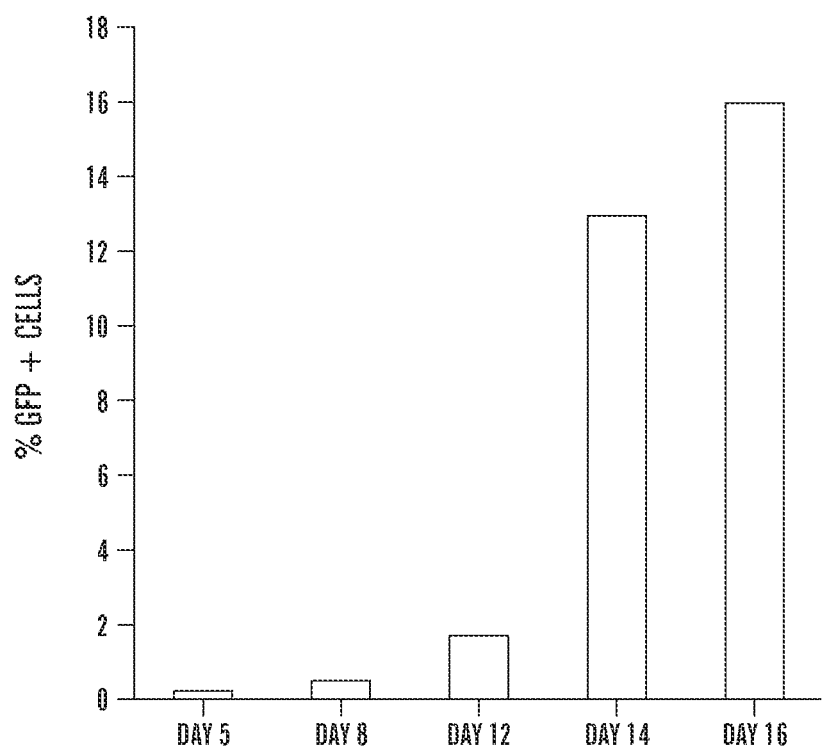
FIG. 3 shows the dynamics of reprogramming using a single lentiviral stem-cell cassette. Analysis of GFP expression over time in TTFs purified from Sox2-GFP M2rtTA double knock-in mice infected with pHAGE-Tet-STEMCCA vector. Transduced cells from independent wells were collected at each time point following doxycycline exposure. GFP expression was analyzed using a FACScan machine. The Day 5 result was indistinguishable from background GFP expression.

It was found that the pHAGE-STEMCCA lentiviral particle reprograms fibroblasts with similar kinetics but higher efficiency compared to prior systems employing multiple vectors (Okita et al., 2007, Nature 448, 313-317; Wernig et al., 2007, Nature 448, 318-324). Robust expression of GFP from the Sox2 locus in TTFs following dox-induction of reprogramming factors was detectable (by FACS and microscopy) at days 8-9 of induction, similar to previous observations (Stadtfeld et al., 2008, Cell Stem Cell 2, 230-240). By day 16, approximately 15% of total cells were GFP+ (FIG. 3). Approximately 50±8 (average +/−SD) GFP positive colonies was obtained out of 100,000 TTFs exposed to pHAGE-STEMCCA lentiviruses. Taking into consideration the low viral transduction efficiency in our experiments (10-15%), which is likely due to the low viral titers used, the effective reprogramming efficiency is approximately 0.5%, 10-fold higher than that observed in prior reports (0.03-0.05%) (Okita et al., 2007, supra; Wernig et al., 2007 supra).

iPS Cells Generated with pHAGE-STEMCCA are Pluripotent

Figure 4C:
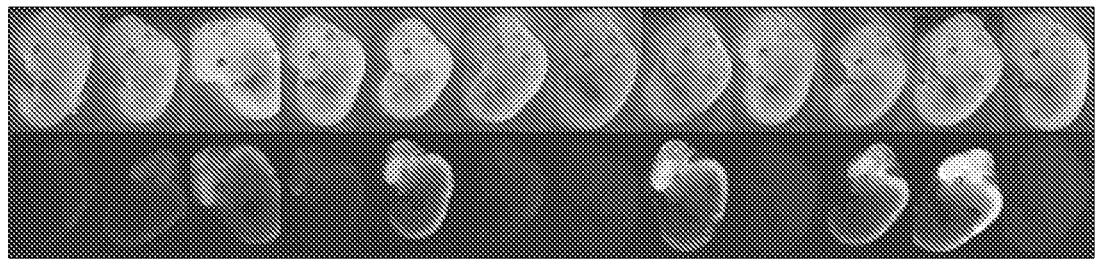
FIG. 4C shows the iPS cells generated with pHAGE-Tet-STEMCCA vector from TTFs of a Sox2-GFP Rosa26-

The capacity of iPS clones derived with constitutive and inducible STEMCCA vectors to differentiate into the three germ layers in teratomas was assess. When injected into NOD/SCID mice, iPS cells derived from both vectors were capable of inducing teratoma formation with the generation of derivatives from all three germ layers (FIGS. 4A and 4B). Next, blastocyst injections were performed in order to further confirm the pluripotency of iPS cells generated using pHAGE-STEMCCA. iPS cells derived from the TTFs of Sox2-GFP Rosa26-M2rtTA mice using the inducible pHAGE-STEMCCA contributed to embryo development when injected into blastocysts (FIG. 4C), as evidenced by Sox2-GFP expression in neural crest-derived tissues. Out of 14 implanted blastocysts, 12 developed into mid-term embryos and 9 showed easily detectable GFP+ iPS-derived cells contributing to the chimeric embryos (FIG. 4C). These results indicate that iPS cells generated with a single viral vector are pluripotent.

The use of a single lentiviral vector for the derivation of iPS cells will help reduce the variability in efficiency that has been observed between different laboratories, thus enabling more consistent genetic and biochemical characterizations of iPS cells and the reprogramming process. From the safety perspective, we have shown that iPS cells can be produced with minimal numbers of viral integrations, significantly reducing the risks of insertional mutagenesis and viral reactivation.

Example 2

Reprogramming of somatic cells to a pluripotent state has been achieved by the introduction of four transcription factors, OCT4, KLF4, SOX2 and c-MYC using four independent retroviral vectors (Takahashi K. and Yamanaka S., Cell. 2006, 126:663-676). Following the reproduction and extension of these studies in both murine and human cells (Okita K, et al., Nature. 2007, 448:313-317; Maherali N, et al., Cell Stem Cell. 2007, 1:55-70; Wernig M, et al., Nature. 2007, 448:318-324; Takahashi K, et al., Cell. 2007, 131:861-872; Yu J, et al., Science. 2007; 318:1917-1920), it is now widely accepted that iPS cells share many of the characteristics of embryonic stem cells (ESC), including gene expression profiles, epigenetic signatures and pluripotency (Wernig M, et al., Nature. 2007, 448:318-324; Brambrink T, et al., Cell Stem Cell. 2008; 2:151-159; Meissner A, et al., Nature, 2008, 454:

766-70; Mikkelsen T S, et al., Nature, 2007, 448:553-560; Stadtfeld M, et al., Cell Stem Cell. 2008, 2:230-240).

Since iPS cells can be generated from mature somatic cells, such as skin fibroblasts (Aasen T, et al., Nat. Biotechnol. 2008, 26:1276-1284; Park I H, et al., Cell. 2008, 134(5):877-86; Dimos J T, et al., Science. 2008, 321:1218-1221), enabling the derivation of patient-specific cells and autologous tissues, it is often predicted that iPS cells will become a powerful tool for biological research as well as a potent source for regenerative medicine. In order for this technology to become clinically relevant, however, methods need to be developed that improve the safety profile of the technology while increasing the overall efficiency of the production of the cells. Several studies have demonstrated that reactivation or sustained expression of reprogramming transgenes can result in deleterious outcomes such as tumor formation (Maherali N, et al., Cell Stem Cell 2007, 1:55-70) or the disruption of pluripotency (Kopp J L, et al., Stem Cells. 2008, 26:903-911; Niwa H, et al., Nat. Genet. 2000, 24:372-376). Moreover, the study of the biology of reprogramming and the ability to evaluate how closely iPS cells and ESC functionally resemble each other will greatly benefit from the use of homogeneous populations devoid of any residual transgene expression.

Recently, a series of studies have demonstrated proof of principle in the generation of murine iPS cells without viral integrations (Okita K, et al., Science. 2008, 322:949-53; Stadtfeld M, et al., Science 2008, 322:945-9). It should be noted, however, that the efficiency of reprogramming in these studies was low and their application for deriving iPS cells from diverse, easily-accessible target somatic cells appears to be limited.

Similarly, transposon-mediated reprogramming, albeit at low efficiency, was able to generate murine iPS cells free of exogenous factors (Woltjen K, et al., Nature. 2009, 458:766-70). The potential toxicity associated with the use of the transposon/transposase system in iPS cells, however, remains to be studied (Geurts A M, et al., PLoS Genet. 200, 2:e56; Wang W, et al., Proc. Natl. Acad. Sci. U.S.A. 2008, 105:9290-9295). Most recently, Jaenisch and colleagues demonstrated Cre-mediated excision of multiple integrated reprogramming lentiviral vectors in human iPS cells following the completion of reprogramming (Soldner F, et al., Cell. 2009, 136:964-977). This important advance demonstrated that prior to excision the transcriptome of iPS cells differs slightly from control ESC. To date it remains unclear whether these subtle differences in global gene expression between iPS cells and ESC are accompanied by significant functional differences. Moreover, if indeed removal of transgenes is necessary for proper functioning of iPS cells, methods that are simple, efficient, and involve minimal screening strategies for deriving 'transgene-free' iPS cells represent important advances for the clinical translation of this technology.

As described herein in Example 1 is the use of a single lentiviral 'stem cell cassette' (STEMCCA) for the efficient generation of iPS cells from post-natal fibroblasts (Sommer C A, et al., Stem Cells. 2009; 27:543-549). Importantly, the use of a single polycistronic vector, expressing Oct4, Klf4, Sox2, and c-Myc, allowed the inventors to obtain iPS cell clones with a single integration. Here the STEMCCA vector was adapt to derive iPS cells free of exogenous reprogramming transgenes. Using a single integrated copy of this polycistronic vector, encoding either 3 or 4 reprogramming factors flanked by loxP sites, efficient reprogramming of post-natal fibroblasts was accomplish, followed by highly efficient Cre-mediated excision of the vector. A direct comparison of iPS cell clones before and after excision reveals that removal of the reprogramming vector markedly improves the developmental potential and differentiation capacity of iPS cells.

Cre-Mediated Excision of a loxP-Containing Polycistronic Reprogramming Vector Allows the Derivation of 'Transgene Free' iPS Cells In order to develop a simplified method for the derivation of transgene-free iPS cells, a vector system that would result in efficient reprogramming with a single reagent, without the need for concurrent additional vectors, transgenes, or chemical exposures was developed and utilized. Hence, in contrast to other studies in which an inducible system was used (Stadtfeld M, et al., Cell Stem Cell. 2008; 2:230-240; Soldner F, et al., Cell. 2009; 136:964-977; Wernig M, et al., Nat. Biotechnol. 2008; 26:916-924) constitutively expressed versions of the lentiviral STEMCCA vector under regulatory control of a human EF 1promoter was selected for this example. This single reagent accomplishes efficient and reliable reprogramming of post-natal cells by expressing four factors (OCT4, KLF4, SOX2, and c-MYC) and obviates the need for additional genetic modification since the transactivator (i.e. rtTA) is not required to induce expression of the reprogramming cassette. Because previous studies have shown that iPS cells can be derived without the presence of exogenous cMyc (Nakagawa M, et al., Nat. Biotechnol. 2008; 26:101-106), a modified 3 factor STEMCCA vector by substituting cMyc with the coding sequence of the red fluorochrome mCherry was also developed. This modified vector, hereafter named STEMCCA-RedLight, constitutively expresses mCherry as well as the 3 reprogramming factors, Oct4, Klf4 and Sox2 from a single polycistronic mRNA, thus allowing monitoring of STEMCCA gene expression in living cells.

In order to allow for excision of the 3 factor or 4 factor STEMCCA vectors, we first introduced a loxP site in the deleted U3 (dU3) region of each lentiviral vector's 3' LTR (Sommer C A, et al., Stem Cells. 2009; 27:543-549) (FIG. 8A). During the normal reverse transcription cycle of the virus before integration, the U3 region is copied to the 5' LTR of the proviral genome, creating a loxP-flanked or 'foxed' version of the STEMCCA vector that integrates into the host chromosome. These floxed STEMCCA vectors (hereafter STEMCCA-loxP and STEMCCA-loxP-RedLight) were used to generate iPS cells from tail tip fibroblasts (TTFs) of Sox2-GFP knock in mice as previously described herein and in Sommer C A, et al., supra. The introduction of loxP sites did not affect viral titers (data not shown), and the STEMCCA-loxP vector was able to generate iPS cell colonies with the same kinetics and the same reprogramming efficiency (~0.5%) as demonstrated previously using STEMCCA herein and in Sommer C A, et al., supra. Initial selection of iPS colonies generated with this vector was based solely on morphological criteria and 20 out of 24 (83%) picked colonies selected on this basis resulted in Sox2-GFP expressing cell lines after expansion. As expected 3 factor reprogramming using STEMCCA-loxP-RedLight was slower and less efficient than 4 factor reprogramming. Sox2-GFP+ colonies appeared only 25-30 days after transduction with STEMCCA-loxP-RedLight (compared to 15-20 days when using the four factors vector), and overall reprogramming efficiency was 0.01%, or 50 fold lower than that observed with STEMCCA-loxP. Importantly, persistent expression of the polycistronic STEMCCA-loxP-RedLight vector, driven by the constitutively active EF1 promoter could be readily visualized by red fluorescence microscopy during reprogramming and was maintained in picked Sox2– GFP+ iPS clones after the completion of reprogramming (data not shown).

Next, Sox2-GFP expressing clones were screened by Southern blot to determine the number of viral integrations, as a first step to pursue vector excision. gDNA was digested with BamHI to expose each individual viral integration. Both, SEFL1 and SEFL2 clones displayed a single integration that is not detected after exposure to Cre (SEFL1-Cre and SEFL2-Cre). Three of 9 screened clones generated with STEMCCA-loxP and 3 of 7 clones generated with STEMCCA-loxP-RedLight showed single copy integration (FIG. 12). In order to excise the single integrated copy of each floxed vector, the clones were exposed to an adenoviral vector (Adeno-Cre) to achieve transient expression of Cre recombinase. Adeno-Cre mediated recombination was employed rather than electroporation of Cre expressing plasmids based on screening studies revealing superior transfection efficiencies of ESC or iPS cells using adenoviral vectors vs. plasmid electroporation (90-100% transfection efficiency vs. 0.5-1%, respectively, data not shown). Adeno-Cre infection of all single integrant iPS cell lines (n=3) resulted in successful Cre-mediated excision of STEMCCA-loxP in 5 out of 5 subclones of each cell line, as evidenced by PCR of gDNA (FIG. 13). In addition, Southern blot analysis confirmed the absence of integrated vector using probes against the WPRE sequence of the STEMCCA vector (FIG. 8C) as well as against the individual reprogramming genes (FIG. 8C and data not shown). PCR screening using oligos specific to Cre was used to confirm that, as expected, no integration of the Adeno-Cre vector had occurred (data not shown). As expected, following excision of the reprogramming cassette and culture expansion of excised iPS cell subclones, the STEMCCA transcript was undetectable as evidenced by RT-PCR (FIG. 8D) and qRT-PCR (FIG. 14), in contrast to the pre-excision parental clones. In iPS cells generated with STEMCCA-loxP-RedLight, disappearance of the mCherry reporter was used to precisely monitor and quantify STEMCCA excision efficiency by fluorescence microscopy (data not shown) and FACS (FIG. 8B). These iPS cells co-expressed mCherry and Sox2-GFP, however, after Adeno—Cre infection, 96 out of 100 colonies expressed only GFP but not mCherry, suggesting an excision efficiency of almost 100%.

Similar results were obtained when probing for Klf4 (FIG. 8C). In this case, the endogenous gene was evident in all clones (closed arrowhead) while the STEMCCA encoded Klf4 is not present following Cre excision (open arrowhead). Gemonic DNA was digested with BglII to obtain a band of 6.7 Kb that confirms appropriate viral transmission. For a control, STEMCCA-loxP plasmid DNA representing 2.5 copies of the insert was digested with BglII. A single band corresponding to an integration of the correct size was observed in SEFL1 and SEFL2 clones and was not present following Cre treatment.

iPS Cells Display Stable Growth Characteristics and Stem Cell Marker Gene Expression After Excision of Reprogramming Transgenes For further study of iPS cells following excision of the reprogramming transgenes, two subclones generated after excision of STEMCCA-loxP were selected and named SEFL1-Cre and SEFL2-Cre, based on their origin from the parental SEFL1 and SEFL2 clones, respectively (FIG. 8C). As shown in FIGS. 9A and 9B, after STEMCCA excision iPS cells maintained expression of alkaline phosphatase (AP), SSEA1, Sox2-GFP and a variety of stem cell markers as evidenced by RT-PCR. In addition, the methylation status of the Oct4 and Nanog proximal promoter regions was analyzed by bisulphite sequencing (FIG. 9C). Both before and after STEMCCA-loxP excision, established iPS cell clones exhibited unmethylated CpG islands at these key loci, in contrast to parental fibroblasts. Importantly, iPS cell expansion appeared to be stable following excision of the STEMCCA-loxP as evidenced by the ability of the cells to be maintained in the undifferentiated state in culture for at least 20 passages.

Excision of Reprogramming Transgenes Facilitates the Developmental Capacity of iPS Cells As previously reported, the iPS cells generated with the constitutive STEMCCA vector were able to differentiate into all three germ layers in teratoma assays, despite the residual expression of exogenous reprogramming genes (in Example 1 and Sommer C A, et al., Stem Cells. 2009; 27:543-549). Indeed, these results were confirmed using the SEFL1 or SEFL2 clones regardless of whether these clones were tested before or after excision of the STEMCCA-loxP, SEFL1 and SEFL2 iPS cell lines readily gave rise to differentiated cells of all three primary germ layers in teratoma assays (FIG. 10A).

Constitutive expression of STEMCCA, however, did appear to adversely affect the in vivo developmental potential of iPS cells after transplantation into mouse blastocysts. As shown in FIG. 10B, iPS cells generated with the constitutive STEMCCA vector were injected into 15 blastocysts followed by midgestation (E11.5) harvest. These injections yielded only 5 embryos of which 3 were chimeric. All 3 chimeric embryos, however, displayed severe morphological abnormalities. In addition, following four independent attempts we were unable to obtain live chimeras when using three different iPS cell clones containing the constitutive STEMCCA or STEMCCA-loxP vector. In marked contrast, following Cre-mediated excision of STEMCCA-loxP, iPS cells injected into 14 blastocysts yielded 11 midgestation embryos of which 7 were chimeric with 5/7 displaying normal developmental morphology (FIG. 10C). Moreover, we were able to obtain live chimeric mice from blastocysts injected with iPS cells after excision of STEMCCA-loxP (FIG. 10D).

While these results indicated that sustained expression of the reprogramming genes may affect the ability of iPS cells to undergo appropriate embryonic development in chimeric embryos, it is not clear whether the morphological defects in the chimeric embryos resulted directly from failure of the injected iPS cells to differentiate. Indeed the seemingly intact ability of these same iPS clones to undergo tri-lineage differentiation in teratoma assays indicates they retain some capacity to respond to differentiation cues such as soluble growth factors. Hence, in order to more fully evaluate the effects of residual STEMCCA expression on the capacity of iPS cells to differentiate in response to normal developmental cues active in the early embryo, iPS cells in culture were stimulated with activin A (hereafter activin), a protein known to mimic embryonic nodal/TGF signaling. Activin A has been shown to induce ESC in vitro to differentiate sequentially into primitive streak-like cells followed by definitive endoderm (Gouon-Evans V, et al., Nat. Biotechnol. 2006; 24:1402-1411; Gadue P, et al., Exp. Hematol. 2005; 33:955-964; Kubo A, et al., Development. 2004; 131:1651-1662).

iPS cells before (SEFL1 and SEFL2) and after (SEFL1-Cre and SEFL2-Cre) excision of STEMCCA-loxP are compared to an ESC clone. mRNA extracted on day 0 (−) and day 5 (+) of activin stimulation was used as the template for RT-PCR. Several genes characteristic of ESC i.e. Rex1, Sox2, Esg1 and Nanog, as well as primitive streak (Brachyury: Bry) and early endoderm (FoxA2) markers are depicted. Note lack of induction of the neuroectoderm marker Pax6. Samples prepared without RT were used as the negative control (—RT).

Following Cre-mediated excision of STEMCCA-loxP, 'transgene-free' versions of each iPS cell clone were compared to their parental clones in terms of endodermal potential in vitro in response to activin A. In two independent experiments, analyzed by either conventional or quantitative RT-PCR, each constitutive, integrated STEMCCA-loxP clone showed diminished potential to upregulate endodermal markers in response to activin A in vitro (FIGS. 11A and 11B). Although all clones were able to form embryoid bodies in culture, STEMCCA-loxP containing clones showed little potential to upregulate key endodermal transcription factors, such as brachyury, FOXA2, SOX17, GATA4, and GATA6. Furthermore, these clones showed persistent expression of the pluripotent markers Rex1 and Esg1 after activin A stimulation (FIG. 11A). In contrast, excision of STEMCCA-loxP from these clones improved the capacity of each clone to upregulate endodermal transcription factors and downregulate pluripotent loci in response to activin (FIG. 11A and 11B). Taken together these results underscore the importance of obtaining iPS cells free of exogenous transgenes, not only as a means to improve the safety profile of iPS cells but also to enable their appropriate differentiation potential.

iPS Cells Before and after Excision of Reprogramming Transgenes Display Frequent Trisomy of Chromosome 8

The possibility that Cre recombination in iPS cells might cause chromosomal instability, such as translocation events, was considered. In doing so, karyotyping by light microscopy was performed as well as spectral karyotyping analyses (SKY) on several iPS cell lines before and after Cre-mediated excision of STEMCCA-loxP. Importantly, no translocation events were detected in any of the clones analyzed strongly suggesting that removal of the single integration by Cre-excision has no deleterious effects on the genome of transgene-free iPS cells. However, it was noted that the majority of iPS cells from three out of six clones displayed frequent trisomy of chromosome 8 (data not shown). This chromosomal abnormality appeared to be present prior to Cre-mediated excision of STEMCCA-loxP, but was not present in the parental fibroblast cell line prior to reprogramming (data not shown). In some cells analyzed by SKY (data not shown) an apparently normal number of 40 mouse chromosomes masked the loss of the Y chromosome in combination with trisomy of chromosome 8. These chromosomal abnormalities have been well described in murine ESC with markedly increased frequencies with increased passage number (Ensenat-Waser, et al., In Vitro Cell Dev. Biol. Anim. 2006, 42:1 15-123; Liu X, et al., Dev. Dyn. 1997, 209:85-91). Trisomy 8 is the most common chromosomal abnormality found in murine ESC and is known to increase growth kinetics and preclude germ line transmission (Liu X, et al., 1997, supra). The high frequency of trisomy 8 abnormalities observed in our iPS cell clones was already present by passage 8 and likely favored their outgrowth during culture, as has been described in ESC.

The present disclosure demonstrate one approach for deriving 'transgene-free' iPS cells using a floxed single copy of a polycistronic reprogramming vector. This method allows head-to-head comparisons of the functional capacity of iPS cells before and after excision of reprogramming transgenes. The findings herein emphasize the importance of vector excision prior to directed differentiation of iPS cells in culture, if the goal is to adapt differentiation culture conditions originally developed in ESC culture systems.

This is the first evaluation of the in vitro endodermal potential of iPS cells in serum-free defined culture conditions. In order to generate differentiated precursor cells for modeling or treating human diseases, it is crucial to first show that iPS cells can be directed in culture to recapitulate the sequence of developmental milestones involved in germ layer formation and differentiation. The results indicate that transgene free iPS cells upregulate an endodermal differentiation program in response to the same serum-free culture conditions previously employed to derive definitive endoderm from ESC (Gouon-Evans V, et al., Nat. Biotechnol. 2006). Although persistent expression of reprogramming factors diminished the response of iPS cells to activin in vitro, the precise mechanism for this effect is not clear. During differentiation stem cells exhibit downregulation of loci encoding pluripotent regulators accompanied by activation of master transcriptional regulators of differentiation. The results herein indicate that persistent expression of reprogramming factors interferes with appropriate downregulation of pluripotent loci, such as Rex1 and Esg1 (FIG. 11). Whether persistence of a general pluripotent gene program, or any particular specific reprogramming factor directly resulted in failure to upregulate the endodermal transcriptional regulators FOXA2, SOX17, and GATA4/6 will require further investigation. Recent work suggests that c-MYC over-expression during reprogramming leads to downregulation of somatic differentiation gene programs, whereas OCT4, KLF4, and SOX2 over-expression triggers activation of pluripotency (Sridharan R, Cell. 2009, 136:364-377). It is conceivable that similar mechanisms account for the present findings when reprogrammed cells are then stimulated to differentiate.

The development of methods to derive iPS cells free of exogenous genetic material is particularly important if iPS cells are to be employed for regenerative therapies in human trials. By excising all reprogramming transgenes the disclosed approach herein eliminates the risk of oncogenic transgene reactivation following transplantation of iPS-derived cells. In addition, by excision of only a single vector copy, the disclosed approach herein minimizes the risk of chromosomal translocations, an advance over prior methods for Cre-mediated excision of multiple copies of individual reprogramming lentiviral vectors (Soldner F, et al., Cell. 2009, 136:964-977).

It should be noted that a number of technical hurdles complicate the use of Cre-mediated excision of DNA sequences from stem cells, potentially limiting the application of these methods to easily generate iPS cells free of floxed transgenes. First, delivery of Cre to ESC or iPS cells has been previously noted to be inefficient; second, screening methods to detect successful Cre-recombination may be cumbersome; and third, clumping of cells after delivery of Cre. The mCherry-containing STEMCCA-loxP-RedLight vector described herein can be particularly helpful in surmounting these hurdles, since this single reagent accomplishes effective '3 factor reprogramming', and the results demonstrate that Cre-recombination efficiency and excision of reprogramming transgenes from the resulting iPS cells can be readily visualized and monitored in individual living cells and colonies in culture. Indeed, it was found that adenoviral delivery of Cre as well as Cre recombination to be highly efficient in iPS cells using monitoring of mCherry disappearance to optimize our transgene excision methodology. Furthermore, FACS sorting based on mCherry expression may be easily employed by those investigators wishing to rapidly separate excised from unexcised iPS cells.

It was also found that trisomy of chromosome 8 was frequent in these iPS cell lines independent of Cre-mediated excision of reprogramming transgenes. This trisomy is common in ESC but has not been reported previously in iPS cells. While this observation further emphasizes the similarity between iPS cells and ESC, it is not yet known whether the overexpression of reprogramming factors facilitates this chromosomal abnormality. In ESC, frequency of this trisomy increases with passage number, and it is possible that the several passages required to generate stable iPS cells during the gradual reprogramming process allow for more prevalent trisomies in iPS cells than has been previously appreciated.

The additional passages required to screen for iPS cell clones with single vector copies, perform vector excision, re-screen for excision, and characterize the transgene-free clones may be particularly problematic in terms of chromosomal instability. For this reason, methods to reprogram cells, maintain chromosomal stability, and excise residual transgenes with the highest efficiency and the lowest possible passage number will be important if iPS cells are to be translated for human therapies. Therefore proposed herein is the use of the STEM-CCA-loxP-RedLight vector as a useful tool for accomplishing this goal, since excision of the mCherry 'RedLight' serves as a simple indicator, requiring minimal screening, for the generation of transgene-free iPS cells.

The contents of all references cited throughout this application, as well as the figures and table are incorporated herein by reference.

SEQUENCE LISTING

```
<160> NUMBER OF SEQ ID NOS: 63

<210> SEQ ID NO 1
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (4)..(4)
<223> OTHER INFORMATION: Any amino acid

<400> SEQUENCE: 1

Asp Val Glu Xaa Asn Pro Gly Pro
1               5

<210> SEQ ID NO 2
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (4)..(4)
<223> OTHER INFORMATION: Any amino acid

<400> SEQUENCE: 2

Asp Ile Glu Xaa Asn Pro Gly Pro
1               5

<210> SEQ ID NO 3
<211> LENGTH: 2518
<212> TYPE: DNA
<213> ORGANISM: Homo sapiens

<400> SEQUENCE: 3
ctattaactt gttcaaaaaa gtatcaggag ttgtcaaggc agagaagaga gtgtttgcaa      60
aagggggaaa gtagtttgct gcctctttaa gactaggact gagagaaaga agaggagaga     120
gaaagaaagg gagagaagtt tgagcccag gcttaagcct ttccaaaaaa taataataac      180
aatcatcggc ggcggcagga tcggccagag gaggagggaa gcgcttttt tgatcctgat     240 tccagtttgc ctctctcttt ttttccccca aattattctt cgcctgattt tcctcgcgga     300
gccctgcgct cccgacaccc ccgcccgcct cccctcctcc tctcccccg cccgcgggcc     360 ccccaaagtc ccggccgggc cgagggtcgg cggccgccgg cgggccgggc ccgcgcacag     420
cgcccgcatg tacaacatga tggagacgga gctgaagccg ccgggcccgc agcaaacttc     480 gggggcggc ggcggcaact ccaccgcggc ggcgccggg ggcaaccaga aaacagccc       540 ggaccgcgtc aagcggccca tgaatgcctt catggtgtgg tcccgcgggc agcggcgcaa    600
```

```
gatggcccag gagaacccca agatgcacaa ctcggagatc agcaagcgcc tgggcgccga    660
gtggaaactt tgtcggaga cggagaagcg gccgttcatc gacgaggcta agcggctgcg    720
agcgctgcac atgaaggagc acccggatta taaataccgg ccccggcgga aaccaagac    780 gctcatgaag aaggataagt acacgctgcc cggcgggctg ctggccccg gcggcaatag    840 catggcgagc ggggtcgggg tgggcgccgg cctgggcgcg ggcgtgaacc agcgcatgga    900
cagttacgcg cacatgaacg gctggagcaa cggcagctac agcatgatgc aggaccagct    960
gggctacccg cagcacccgg gcctcaatgc gcacggcgca gcgcagatgc agcccatgca   1020
ccgctacgac gtgagcgccc tgcagtacaa ctccatgacc agctcgcaga cctacatgaa   1080
cggctcgccc acctacagca tgtcctactc gcagcagggc acccctggca tggctcttgg   1140
ctccatgggt tcggtggtca agtccgaggc cagctccagc cccccgtgtgg ttacctcttc   1200 ctcccactcc agggcgccct gccaggccgg ggacctccgg gacatgatca gcatgtatct   1260
ccccggcgcc gaggtgccgg aacccgccgc ccccagcaga cttcacatgt cccagcacta   1320
ccagagcggc ccggtgcccg gcacggccat taacggcaca ctgccctct cacacatgtg   1380 agggccggac agcgaactgg agggggggaga aattttcaaa gaaaaacgag ggaaatggga   1440
ggggtgcaaa agaggagagt aagaaacagc atggagaaaa cccggtacgc tcaaaaagaa   1500
aaaggaaaaa aaaaaatccc atcacccaca gcaaatgaca gctgcaaaag agaacaccaa   1560
tcccatccac actcacgcaa aaaccgcgat gccgacaaga aaactttat gagagagatc   1620 ctggacttct ttttggggga ctattttgt acagagaaaa cctggggagg gtggggaggg   1680
cgggggaatg gaccttgtat agatctggag gaaagaaagc tacgaaaaac ttttttaaaag   1740 ttctagtggt acgtaggag ctttgcagga agtttgcaaa agtctttacc aataatatt   1800 agagctagtc tccaagcgac gaaaaaaatg ttttaatatt tgcaagcaac ttttgtacag   1860
tatttatcga gataaacatg gcaatcaaaa tgtccattgt ttataagctg agaatttgcc   1920
aatatttttc aaggagaggc ttcttgctga attttgattc tgcagctgaa atttaggaca   1980
gttgcaaacg tgaaagaag aaaattattc aaatttggac attttaattg tttaaaaatt   2040
gtacaaaagg aaaaaaattag aataagtact ggcgaaccat ctctgtggtc ttgttttaaaa   2100 agggcaaaag ttttagactg tactaaattt tataacttac tgttaaaagc aaaaatggcc   2160
atgcaggttg acaccgttgg taatttataa tagcttttgt tcgatcccaa ctttccattt   2220
tgttcagata aaaaaaacca tgaaattact gtgtttgaaa tattttctta tggtttgtaa   2280
tatttctgta aatttattgt gatatttaa ggttttcccc cctttatttt ccgtagttgt   2340
attttaaaag attcggctct gtattatttg aatcagtctg ccgagaatcc atgtatatat   2400
ttgaactaat atcatcctta taacaggtac attttcaact taagttttta ctccattatg   2460
cacagtttga gataaataaa ttttttgaaat atggacactg aaaaaaaaaa aaaaaaa     2518

```

<210> SEQ ID NO 4
<211> LENGTH: 2377
<212> TYPE: DNA
<213> ORGANISM: Homo sapiens

<400> SEQUENCE: 4

```
accccccgagc tgtgctgctc gcggccgcca ccgccgggcc ccggccgtcc ctggctcccc     60
tcctgcctcg agaagggcag ggcttctcag aggcttggcg ggaaaaagaa cggagggagg    120
gatcgcgctg agtataaaag ccggttttcg gggcttatc taactcgctg tagtaattcc    180
agcgagaggc agagggagcg agcgggcggc cggctagggt ggaagagccg ggcgagcaga    240
```

```
gctgcgctgc gggcgtcctg ggaagggaga tccggagcga ataggggget tcgcctctgg    300 cccagccctc ccgctgatcc cccagccagc ggtccgcaac ccttgccgca tccacgaaac    360
tttgcccata gcagcgggcg ggcactttgc actggaactt acaacacccg agcaaggacg    420
cgactctccc gacgcgggga ggctattctg cccatttggg gacacttccc cgccgctgcc    480
aggacccgct tctctgaaag gctctccttg cagctgctta gacgctggat tttttcggg     540 tagtggaaaa ccagcagcct cccgcgacga tgccctcaa cgttagcttc accaacagga     600
actatgacct cgactacgac tcggtgcagc cgtattcta ctgcgacgag gaggagaact     660
tctaccagca gcagcagcag agcgagctgc agccccggc gccagcgag gatatctgga     720 agaaattcga gctgctgccc accccgcccc tgtccctag ccgccgctcc gggctctgct     780
cgccctccta cgttgcggtc acccttcct ccttcgggg agacaacgac ggcggtggcg     840
ggagcttctc cacggccgac cagctggaga tggtgaccga gctgctggga ggagacatgg    900
tgaaccagag tttcatctgc gacccggacg acgagacctt catcaaaaac atcatcatcc    960
aggactgtat gtggagcggc ttctcggccg ccgccaagct cgtctcagag aagctggcct   1020
cctaccaggc tgcgcgcaaa gacagcggca gcccgaaccc cgcccgcggc cacagcgtct   1080
gctccacctc cagcttgtac ctgcaggatc tgagcgccgc cgcctcagag tgcatcgacc   1140
cctcggtggt cttccctac cctctcaacg acagcagctc gcccaagtcc tgcgcctcgc    1200
aagactccag cgccttctct ccgtcctcgg attctctgct ctcctcgacg gagtcctccc   1260
cgcagggcag ccccgagccc ctggtgctcc atgaggagac accgccacc accagcagcg   1320 actctgagga ggaacaagaa gatgaggaag aaatcgatgt tgtttctgtg gaaaagaggc   1380 aggtcctgg caaaaggtca gagtctggat caccttctgc tggaggccac agcaaacctc    1440
ctcacagccc actggtcctc aagaggtgcc acgtctccac acatcagcac aactacgcag   1500
cgcctccctc cactcggaag gactatcctg ctgccaagag ggtcaagttg acagtgtca     1560 gagtcctgag acagatcagc aacaaccgaa aatgcaccag cccaggtcc tcggacacgg     1620 aggagaatgt caagaggcga acacacaacg tcttggagcg ccagaggagg aacgagctaa    1680
aacggagctt ttttgccctg cgtgaccaga tcccggagt tggaaacaat gaaaaggccc    1740
ccaaggtagt tatccttaaa aaagccacag catacatcct gtccgtccaa gcagaggagc    1800
aaaagctcat ttctgaagag gacttgttgc ggaaacgacg agaacagttg aaacacaaac    1860
ttgaacagct acggaactct tgtgcgtaag gaaagtaag gaaacgatt ccttctaaca     1920 gaaatgtcct gagcaatcac ctatgaactt gtttcaaatg catgatcaaa tgcaacctca    1980
caaccttggc tgagtcttga gactgaaaga tttagccata atgtaaactg cctcaaattg    2040
gactttgggg ataaaagaac tttttttatgc ttaccatctt ttttttttct ttaacagatt   2100
tgtatttaag aattgttttt aaaaaatttt aagatttaca caatgtttct ctgtaaatat    2160
tgccattaaa tgtaaataac tttaataaaa cgtttatagc agttacacag aatttcaatc    2220
ctagtatata gtacctagta ttataggtac tataaacct aatttttttt atttaagtac     2280
attttgcttt ttaagttga tttttttcta ttgtttttag aaaaaataaa ataactggca    2340
aatatatcat tgagccaaaa aaaaaaaaaa aaaaaaa                             2377
```

<210> SEQ ID NO 5
<211> LENGTH: 2949
<212> TYPE: DNA
<213> ORGANISM: Homo sapiens

```
<400> SEQUENCE: 5
agtttcccga ccagagagaa cgaacgtgtc tgcgggcgcg cggggagcag aggcggtggc      60
gggcggcggc ggcaccggga gccgccgagt gaccctcccc cgcccctctg gccccccacc     120
ctcccacccg cccgtggccc gcgcccatgg ccgcgcgcgc tccacacaac tcaccggagt     180
ccgcgccttg cgccgccgac cagttcgcag ctccgcgcca cggcagccag tctcacctgg     240
cggcaccgcc cgcccaccgc cccggccaca gccctgcgc ccacggcagc actcgaggcg      300
accgcgacag tggtggggga cgctgctgag tggaagagag cgcagcccgg ccaccggacc     360
tacttactcg ccttgctgat tgtctatttt tgcgtttaca acttttctaa gaacttttgt     420
atacaaagga acttttttaaa aaagacgctt ccaagttata tttaatccaa agaagaagga    480
tctcggccaa tttggggttt tgggttttgg cttcgtttct tctcttcgtt gactttgggg    540
ttcaggtgcc ccagctgctt cgggctgccg aggaccttct gggcccccac attaatgagg    600
cagccacctg gcgagtctga catggctgtc agcgacgcgc tgctcccatc tttctccacg    660
ttcgcgtctg gcccggcggg aagggagaag acactgcgtc aagcaggtgc cccgaataac    720
cgctggcggg aggagctctc ccacatgaag cgacttcccc cagtgcttcc ggccgcccc    780 tatgacctgg cggcggcgac cgtggccaca gacctggaga gcggcggagc cggtgcggct   840
tgcggcggta gcaacctggc gcccctacct cggagagaga ccgaggagtt caacgatctc    900
ctggacctgg actttattct ctccaattcg ctgacccatc ctccggagtc agtggccgcc    960
accgtgtcct cgtcagcgtc agcctcctct tcgtcgtcgc cgtcgagcag cggccctgcc   1020
agcgcgccct ccacctgcag cttcacctat ccgatccggg ccgggaacga cccgggcgtg   1080
gcgccgggcg gcacgggcgg aggcctcctc tatggcaggg agtccgctcc cctccgacg    1140 gctcccttca acctggcgga catcaacgac gtgagcccct cgggcggctt cgtggccgag   1200
ctcctgcggc cagaattgga cccggtgtac attccgccgc agcagccgca gccgccaggt   1260
ggcgggctga tgggcaagtt cgtgctgaag gcgtcgctga gcgcccctgg cagcgagtac   1320
ggcagcccgt cggtcatcag cgtcagcaaa ggcagccctg acggcagcca cccggtggtg   1380
gtggcgccct acaacggcgg gccgccgcgc acgtgcccca agatcaagca ggaggcggtc   1440
tcttcgtgca cccacttggg cgctggaccc cctctcagca atggccaccg gccggctgca   1500
cacgacttcc ccctggggcg gcagctcccc agcaggacta ccccgaccct gggtcttgag   1560
gaagtgctga gcagcaggga ctgtcaccct gccctgccgc ttcctcccgg cttccatccc   1620 caccggggc ccaattaccc atccttcctg cccgatcaga tgcagccgca agtcccgccg     1680
ctccattacc aagagctcat gccacccggt tcctgcatgc cagaggagcc caagccaaag    1740 agggaagac gatcgtggcc ccggaaaagg accgccaccc acacttgtga ttacgcgggc    1800
tgcggcaaaa cctacacaaa gagttcccat ctcaaggcac acctgcgaac ccacacaggt   1860
gagaaacctt accactgtga ctgggacggc tgtggatgga aattcgcccg ctcagatgaa    1920
ctgaccaggc actaccgtaa acacacgggg caccgcccgt tccagtgcca aaaatgcgac    1980
cgagcatttt ccaggtcgga ccacctcgcc ttacacatga gaggcattt ttaaatccca     2040 gacagtggat atgaccccac ctgccagaag agaattcagt attttttact tttcacactg   2100
tcttcccgat gagggaagga gcccagccag aaagcactac aatcatggtc aagttcccaa   2160
ctgagtcatc ttgtgagtgg ataatcagga aaaatgagga atccaaaaga caaaaatcaa   2220
agaacagatg gggtctgtga ctggatcttc tatcattcca attctaaatc cgacttgaat   2280
attcctggac ttacaaaatg ccaagggggt gactggaagt tgtggatatc agggtataaa   2340
```

```
ttatatccgt gagttggggg agggaagacc agaattccct tgaattgtgt attgatgcaa    2400
tataagcata aaagatcacc ttgtattctc tttaccttct aaaagccatt attatgatgt    2460
tagaagaaga ggaagaaatt caggtacaga aaacatgttt aaatagccta atgatggtg     2520 cttggtgagt cttggttcta aaggtaccaa acaaggaagc caaagttttc aaactgctgc    2580
atactttgac aaggaaaatc tatatttgtc ttccgatcaa catttatgac ctaagtcagg    2640
taatatacct ggtttacttc tttagcattt ttatgcagac agtctgttat gcactgtggt    2700
ttcagatgtg caataatttg tacaatggtt tattcccaag tatgccttaa gcagaacaaa    2760 tgtgttttc tatatagttc cttgccttaa taaatatgta atataaattt aagcaaacgt     2820
ctattttgta tatttgtaaa ctacaaagta aaatgaacat tttgtggagt ttgtattttg    2880
catactcaag gtgagaatta agttttaaat aaacctataa tattttatct gaaaaaaaaa    2940
aaaaaaaaa                                                            2949

<210> SEQ ID NO 6
<211> LENGTH: 1411
<212> TYPE: DNA
<213> ORGANISM: Homo sapiens

<400> SEQUENCE: 6
ccttcgcaag ccctcatttc accaggcccc cggcttgggg cgccttcctt ccccatggcg      60
ggacacctgg cttcggattt cgccttctcg cccctccag gtggtggagg tgatgggcca     120 gggggggccgg agccgggctg ggttgatcct cggacctggc taagcttcca aggccctcct    180
ggagggccag gaatcgggcc gggggttggg ccaggctctg aggtgtgggg gattccccca    240 tgcccccgc cgtatgagtt ctgtgggggg atggcgtact gtgggcccca ggttggagtg     300
gggctagtgc cccaaggcgg cttggagacc tctcagcctg agggcgaagc aggagtcggg    360
gtggagagca actccgatgg ggcctccccg gagccctgca ccgtcacccc tggtgccgtg    420
aagctggaga aggagaagct ggagcaaaac ccggaggagt cccaggacat caaagctctg    480
cagaaagaac tcgagcaatt tgccaagctc ctgaagcaga gaggatcac cctgggatat     540 acacaggccg atgtggggct caccctgggg gttctatttg gaaggtatt cagccaaacg     600 accatctgcc gctttgaggc tctgcagctt agcttcaaga acatgtgtaa gctgcggccc    660
ttgctgcaga gtgggtgga ggaagctgac aacaatgaaa atcttcagga gatatgcaaa     720
gcagaaaccc tcgtgcaggc ccgaaagaga aagcgaacca gtatcgagaa ccgagtgaga    780
ggcaacctgg agaatttgtt cctgcagtgc ccgaaaccca cactgcagca gatcagccac    840
atcgcccagc agcttgggct cgagaaggat gtggtccgag tgtggttctg taaccggcgc    900
cagaagggca agcgatcaag cagcgactat gcacaacgag aggattttga ggctgctggg    960
tctcctttct caggggggacc agtgtccttt cctctggccc cagggcccca ttttggtacc    1020
ccaggctatg ggagccctca cttcactgca ctgtactcct cggtcccttt ccctgagggg    1080
gaagcctttc cccctgtctc cgtcaccact ctgggctctc ccatgcattc aaactgaggt    1140
gcctgccctt ctaggaatgg gggacagggg gaggggagga gctagggaaa gaaaacctgg    1200
agtttgtgcc agggttttg ggattaagtt cttcattcac taaggaagga attgggaaca     1260
caaagggtgg gggcagggga gtttggggca actggttgga gggaaggtga agttcaatga    1320
tgctcttgat tttaatccca catcatgtat cactttttc ttaaataaag aagcctggga    1380
cacagtagat agacacactt aaaaaaaaa a                                     1411
```

<210> SEQ ID NO 7
<211> LENGTH: 1155
<212> TYPE: DNA
<213> ORGANISM: Homo sapiens

<400> SEQUENCE: 7

| | | | | | |
|---|---|---|---|---|---|
| catgagtcag | tgaacaggga | atgggtgaat | gacatttgtg | ggtaggttat | ttctagaagt | 60 |
| taggtgggca | gcttggaagg | cagatgcact | tctacagact | attccttggg | gccacacgta | 120 |
| ggttcttgaa | tcccgaatgg | aaaggggaga | ttgataactg | gtgtgtttat | gttcttacaa | 180 |
| gtcttctgcc | ttttaaaatc | cagtcccagg | acatcaaagc | tctgcagaaa | gaactcgagc | 240 |
| aatttgccaa | gctcctgaag | cagaagagga | tcaccctggg | atatacacag | gccgatgtgg | 300 |
| ggctcaccct | gggggttcta | tttgggaagg | tattcagcca | aacgaccatc | tgccgctttg | 360 |
| aggctctgca | gcttagcttc | aagaacatgt | gtaagctgcg | gcccttgctg | cagaagtggg | 420 |
| tggaggaagc | tgacaacaat | gaaaatcttc | aggagatatg | caaagcagaa | accctcgtgc | 480 |
| aggcccgaaa | gagaaagcga | accagtatcg | agaaccgagt | gagaggcaac | ctggagaatt | 540 |
| tgttcctgca | gtgcccgaaa | cccacactgc | agcagatcag | ccacatcgcc | agcagcttg | 600 |
| ggctcgagaa | ggatgtggtc | cgagtgtggt | tctgtaaccg | cgccagaag | ggcaagcgat | 660 |
| caagcagcga | ctatgcacaa | cgagaggatt | ttgaggctgc | tgggtctcct | ttctcagggg | 720 |
| gaccagtgtc | ctttcctctg | gccccagggc | cccattttgg | tacccaggc | tatgggagcc | 780 |
| ctcacttcac | tgcactgtac | tcctcggtcc | ctttccctga | ggggaagcc | tttcccctg | 840 |
| tctccgtcac | cactctgggc | tctcccatgc | attcaaactg | aggtgcctgc | ccttctagga | 900 |
| atgggggaca | gggggagggg | aggagctagg | gaaagaaaac | ctggagtttg | tgccagggtt | 960 |
| tttgggatta | agttcttcat | tcactaagga | aggaattggg | aacacaaagg | gtgggggcag | 1020 |
| gggagtttgg | ggcaactggt | tggagggaag | gtgaagttca | atgatgctct | tgattttaat | 1080 |
| cccacatcat | gtatcacttt | tttcttaaat | aaagaagcct | gggacacagt | agatagacac | 1140 |
| acttaaaaaa | aaaaa | | | | | 1155 |

<210> SEQ ID NO 8
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Val Lys Gln Thr Leu Asn Asn Phe Asp Leu Leu Lys Leu Ala Gly Asp
1               5                   10                  15

Val Glu Ser Asn Pro Gly Pro
            20

<210> SEQ ID NO 9
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Gln Cys Thr Asn Tyr Ala Leu Leu Lys Leu Ala Gly Asp Val Glu Ser

```
Asn Pro Gly Pro
            20

<210> SEQ ID NO 10
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Glu Gly Arg Ser Leu Leu Thr Cys Gly Asp Val Glu Glu Asn Pro Gly
1               5                   10                  15
Pro

<210> SEQ ID NO 11
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Ala Thr Asn Phe Ser Leu Leu Lys Gln Ala Gly Asp Val Glu Glu Asn
1               5                   10                  15
Pro Gly Pro

<210> SEQ ID NO 12
<211> LENGTH: 63
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 12
tgggccagga ttctcctcga cgtcaccgca tgttagcaga cttcctctgc cctctccact    60
gcc                                                                  63

<210> SEQ ID NO 13
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 13
gatctggtac aggatgttct agctacg                                        27

<210> SEQ ID NO 14
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 14
gatcttgcgc ccggcccg                                                    18

<210> SEQ ID NO 15
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 15
caccggcggc cgccatggat cctcgaacct ggctaagctt ccaag                      45

<210> SEQ ID NO 16
<211> LENGTH: 71
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 16
cttgagaagg tcaaaattca aagtctgttt cacgccactt ccgtttgaat gcatgggaga      60
gcccagagca g                                                           71

<210> SEQ ID NO 17
<211> LENGTH: 86
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 17
aaacagactt tgaattttga ccttctcaag ttggcgggag acgtggagtc caacccaggg      60
cccatggcta gcgacgctct gctccc                                           86

<210> SEQ ID NO 18
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 18
tttggatcct taaaagtgcc tcttcatgtg taaggcaag                             39

<210> SEQ ID NO 19
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 19
ggtttcttac atatgatgta taacatgatg gagacggagc tgaag                      45

```
<210> SEQ ID NO 20
<211> LENGTH: 90
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 20
tttcaacatc gccagcgagt tcaacaaag cgtagttagt acattgccca ctacccatgt     60
gcgacagggg cagtgtgccg ttaatggccg                                     90

<210> SEQ ID NO 21
<211> LENGTH: 81
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 21
ctttgttgaa actcgctggc gatgttgaaa gtaaccccgg tcctatgccc ctcaacgtga     60
acttcaccaa caggaactat g                                              81

<210> SEQ ID NO 22
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 22
ggtttatcga tttatgcacc agagtttcga agctgttc                            38

<210> SEQ ID NO 23
<211> LENGTH: 11745
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 23
tggaagggct aattcactcc caagaagac aagatatcct tgatctgtgg atctaccaca     60
cacaaggcta cttccctgat tagcagaact acacaccagg gccagggtc agatatccac    120 tgacctttgg atggtgctac aagctagtac cagttgagcc agataaggta gaagaggcca   180
ataaaggaga gaacaccagc ttgttacacc ctgtgagcct gcatgggatg gatgacccgg   240
agagagaagt gttagagtgg aggtttgaca gccgcctagc atttcatcac gtggcccgag   300
agctgcatcc ggagtacttc aagaactgct gatatcgagc ttgctacaag ggactttccg   360
ctggggactt tccagggagg cgtggcctgg gcgggactgg ggagtggcga gccctcagat   420
cctgcatata agcagctgct ttttgcctgt actgggtctc tctggttaga ccagatctga   480
gcctgggagc tctctggcta actagggaac ccactgctta agcctcaata aagcttgcct   540
tgagtgcttc aagtagtgtg tgcccgtctg ttgtgtgact ctggtaacta gagatccctc   600
agaccctttt agtcagtgtg gaaaatctct agcagtggcg cccgaacagg gacttgaaag   660
```

```
cgaaagggaa accagaggag ctctctcgac gcaggactcg gcttgctgaa gcgcgcacgg    720
caagaggcga gggcggcga ctggtgagta cgccaaaaat tttgactagc ggaggctaga    780
aggagagaga tgggtgcgag agcgtcagta ttaagcgggg gagaattaga tcgcgatggg    840
aaaaaattcg gttaaggcca gggggaaaga aaaatataa attaaaacat atagtatggg    900
caagcaggga gctagaacga ttcgcagtta atcctggcct gttagaaaca tcagaaggct    960
gtagacaaat actgggacag ctacaaccat cccttcagac aggatcagaa gaacttagat   1020
cattatataa tacagtagca accctctatt gtgtgcatca aaggatagag ataaaagaca   1080
ccaaggaagc tttagacaag atagaggaag agcaaaacaa aagtaagacc accgcacagc   1140
aagcggccgg ccgctgatct tcagacctgg aggaggagat atgagggaca attggagaag   1200
tgaattatat aaatataaag tagtaaaaat tgaaccatta ggagtagcac ccaccaaggc   1260
aaagagaaga gtggtgcaga gagaaaaaag agcagtggga ataggagctt tgttccttgg   1320
gttcttggga gcagcaggaa gcactatggg cgcagcgtca atgacgctga cggtacaggc   1380
cagacaatta ttgtctggta tagtgcagca gcagaacaat ttgctgaggg ctattgaggc   1440
gcaacagcat ctgttgcaac tcacagtctg gggcatcaag cagctccagg caagaatcct   1500
ggctgtggaa agatacctaa aggatcaaca gctcctgggg atttggggtt gctctggaaa   1560
actcatttgc accactgctg tgccttggaa tgctagttgg agtaataaat ctctggaaca   1620
gatttggaat cacacgacct ggatggagtg ggacagagaa attaacaatt acacaagctt   1680
aatacactcc ttaattgaag aatcgcaaaa ccagcaagaa aagaatgaac aagaattatt   1740
ggaattagat aaatgggcaa gtttgtggaa ttggtttaac ataacaaatt ggctgtggta   1800
tataaaatta ttcataatga tagtaggagg cttggtaggt ttaagaatag ttttttgctgt   1860 actttctata gtgaatagag ttaggcaggg atattcacca ttatcgtttc agacccacct   1920
cccaaccccg aggggacccg acaggcccga aggaatagaa gaagaaggtg gagagagaga   1980
cagagacaga tccattcgat tagtgaacgg atctcgacgg tatcgccgaa ttcacaaatg   2040
gcagtattca tccacaattt taaaagaaaa ggggggattg ggggggtacag tgcaggggaa   2100 agaatagtag acataatagc aacagacata caaactaaag aattacaaaa acaaattaca   2160
aaaattcaaa attttcgggt ttattacagg gacagcagag atccagtttg gactagtcca   2220
caccctaact gacacactcg agtttaccac tccctatcag tgatagagaa aagtgaaagt   2280
cgagtttacc actccctatc agtgatagag aaaagtgaaa gtcgagttta ccactcccta   2340
tcagtgatag agaaaagtga agtcgagtt taccactccc tatcagtgat agagaaaagt   2400
gaaagtcgag tttaccactc cctatcagtg atagagaaaa gtgaaagtcg agtttaccac   2460
tccctatcag tgatagagaa aagtgaaagt cgagtttacc actccctatc agtgatagag   2520
aaaagtgaaa gtcgagctcg gtacccgggt cgaggtaggc gtgtacggtg gaggcctat   2580 ataagcagag ctcgtttagt gaaccgtcag atcgcctgga gacgccatcc acgctgtttt   2640
gacctccata aagacaccg ggaccgatcc agcctgcggc cgccatggct ggacacctgg   2700
cttcagactt cgccttctca cccccaccag gtgggggtga tgggtcagca gggctggagc   2760
cgggctgggt ggatcctcga acctggctaa gcttccaagg gcctccaggt gggcctggaa   2820
tcggaccagg ctcagaggta ttggggatct ccccatgtcc gcccgcatac gagttctgcg   2880
gagggatggc atactgtgga cctcaggttg gactgggcct agtcccccaa gttggcgtgg   2940
agactttgca gcctgagggc caggcaggag cacgagtgga aagcaactca gagggaacct   3000
cctctgagcc ctgtgccgac cgccccaatg ccgtgaagtt ggagaaggtg gaaccaactc   3060
```

```
ccgaggagtc ccaggacatg aaagccctgc agaaggagct agaacagttt gccaagctgc   3120
tgaagcagaa gaggatcacc ttggggtaca cccaggccga cgtggggctc accctgggcg   3180
ttctctttgg aaaggtgttc agccagacca ccatctgtcg cttcgaggcc ttgcagctca   3240
gccttaagaa catgtgtaag ctgcggcccc tgctggagaa gtgggtggag gaagccgaca   3300
acaatgagaa ccttcaggag atatgcaaat cggagaccct ggtgcaggcc cggaagagaa   3360
agcgaactag cattgagaac cgtgtgaggt ggagtctgga gaccatgttt ctgaagtgcc   3420
cgaagccctc cctacagcag atcactcaca tcgccaatca gcttgggcta gagaaggatg   3480
tggttcgagt atggttctgt aaccggcgcc agaagggcaa aagatcaagt attgagtatt   3540
cccaacgaga agagtatgag gctacaggga ccctttccc agggggggct gtatccttc    3600 ctctgcccc aggtccccac tttggcaccc caggctatgg aagcccccac ttcaccacac    3660
tctactcagt cccttttcct gagggcgagg cctttccctc tgttcccgtc actgctctgg   3720
gctctcccat gcattcaaac ggaagtggcg tgaaacagac tttgaatttt gaccttctca   3780
agttggcggg agacgtggag tccaacccag ggcccatggc tgtcagcgac gctctgctcc   3840
cgtccttctc cacgttcgcg tccggcccgg cgggaaggga gaagacactg cgtccagcag   3900
gtgccccgac taaccgttgg cgtgaggaac tctctcacat gaagcgactt cccccacttc   3960
ccggccgccc ctacgacctg gcggcgacgg tggccacaga cctggagagt ggcggagctg   4020
gtgcagcttg cagcagtaac aacccggccc tcctagcccg gagggagacc gaggagttca   4080
acgacctcct ggacctagac tttatccttt ccaactcgct aacccaccag gaatcggtgg   4140
ccgccaccgt gaccacctcg gcgtcagctt catcctcgtc ttccccagcg agcagcggcc   4200
ctgccagcgc gccctccacc tgcagcttca gctatccgat ccgggccggg ggtgacccgg   4260
gcgtggctgc cagcaacaca ggtggagggc tcctctacag ccgagaatct gcgccacctc   4320
ccacggcccc cttcaacctg gcggacatca atgacgtgag ccctcgggc ggcttcgtgg    4380 ctgagctcct gcggccggag ttggacccag tatacattcc gccacagcag cctcagccgc   4440
caggtggcgg gctgatgggc aagtttgtgc tgaaggcgtc tctgaccacc cctggcagcg   4500
agtacagcag cccttcggtc atcagtgtta gcaaaggaag cccagacggc agccacccg    4560 tggtagtggc ccctacagc ggtgcccgc cgcgcatgtg ccccaagatt aagcaagagg     4620
cggtcccgtc ctgcacggtc agccggtccc tagaggccca tttgagcgct ggaccccagc   4680
tcagcaacgg ccaccggccc aacacacacg acttccccct ggggcggcag ctccccacca   4740
ggactacccc tacactgagt cccgaggaac tgctgaacag cagggactgt cacccctggcc   4800 tgcctcttcc cccaggattc catccccatc cggggcccaa ctaccctcct ttcctgccag   4860
accagatgca gtcacaagtc ccctctctcc attatcaaga gctcatgcca ccgggttcct   4920
gcctgccaga ggagcccaag ccaaagaggg gaagaaggtc gtggccccgg aaaagaacag   4980
ccacccacac ttgtgactat gcaggctgtg gcaaaaccta taccaagagt ctcatctca    5040 aggcacacct gcgaactcac acaggcgaga aaccttacca ctgtgactgg gacggctgtg   5100
ggtggaaatt cgcccgctcc gatgaactga ccaggcacta ccgcaaacac acagggcacc   5160 ggcccttca gtgccagaag tgtgacaggg cctttccag tcggaccac cttgccttac      5220 acatgaagag gcactttaa agatccctcc ccccccta acgttactgg ccgaagccgc       5280
ttggaataag gccggtgtgc gtttgtctat atgttatttt ccaccatatt gccgtctttt    5340
ggcaatgtga gggcccggaa acctggccct gtcttcttga cgagcattcc tagggggtctt  5400
```

```
tcccctctcg ccaaaggaat gcaaggtctg ttgaatgtcg tgaaggaagc agttcctctg    5460
gaagcttctt gaagacaaac aacgtctgta gcgacccttt gcaggcagcg aaccccccca    5520
cctggcgaca ggtgcctctg cggccaaaag ccacgtgtat aagatacacc tgcaaaggcg    5580
gcacaacccc agtgccacgt tgtgagttgg atagttgtgg aaagagtcaa atggctctcc    5640
tcaagcgtat tcaacaaggg gctgaaggat gcccagaagg taccccattg tatgggatct    5700
gatctggggc ctcggtgcac atgctttaca tgtgtttagt cgaggttaaa aaaacgtcta    5760
ggccccccga accacgggga cgtggttttc ctttgaaaaa cacgatgata atatggccac    5820
acatatgatg tataacatga tggagacgga gctgaagccg ccgggcccgc agcaagcttc    5880 gggggggcggc ggcggaggag gcaacgccac ggcggcggcg accggcggca accagaagaa    5940
cagcccggac cgcgtcaaga ggcccatgaa cgccttcatg gtatggtccc ggggcagcg     6000 gcgtaagatg gcccaggaga accccaagat gcacaactcg gagatcagca gcgcctggg     6060 cgcggagtgg aaacttttgt ccgagaccga gaagcggccg ttcatcgacg aggccaagcg    6120
gctgcgcgct ctgcacatga aggagcaccc ggattataaa taccggccgc ggcggaaaac    6180
caagacgctc atgaagaagg ataagtacac gcttcccgga ggcttgctgg ccccccggcgg    6240 gaacagcatg gcgagcgggg ttggggtggg cgccggcctg ggtgcgggcg tgaaccagcg    6300
catggacagc tacgcgcaca tgaacggctg gagcaacggc agctacagca tgatgcagga    6360
gcagctgggc tacccgcagc acccgggcct caacgctcac ggcgcggcac agatgcaacc    6420
gatgcaccgc tacgacgtca gcgccctgca gtacaactcc atgaccagct cgcagaccta    6480
catgaacggc tcgcccacct acagcatgtc ctactcgcag cagggcaccc ccggtatggc    6540
gctgggctcc atgggctctg tggtcaagtc cgaggccagc tccagccccc cgtggttac     6600 ctcttcctcc cactccaggg cgccctgcca ggccggggac ctcgggaca tgatcagcat     6660 gtacctcccc ggcgccgagg tgccggagcc cgctgcgccc agtagactgc acatggccca    6720
gcactaccag agcggcccgg tgcccggcac ggccattaac ggcacactgc ccctgtcgca    6780
catgggtagt gggcaatgta ctaactacgc tttgttgaaa ctcgctggcg atgttgaaag    6840
taaccccggt cctatgcccc tcaacgtgaa cttcaccaac aggaactatg acctcgacta    6900
cgactccgta cagccctatt tcatctgcga cgaggaagag aatttctatc accagcaaca    6960
gcagagcgag ctgcagccgc ccgcgcccag tgaggatatc tggaagaaat tcgagctgct    7020
tcccaccccg cccctgtccc cgagccgccg ctccgggctc tgctctccat cctatgttgc    7080
ggtcgctacg tccttctccc caagggaaga cgatgacggc ggcggtggca acttctccac    7140
cgccgatcag ctgagagtga tgaccgagtt acttggagga gacatggtga accagagctt    7200
catctgcgat cctgacgacg agaccttcat caagaacatc atcatccagg actgtatgtg    7260
gagcggtttc tcagccgctg ccaagctggt ctcggagaag ctggcctcct accaggctgc    7320
gcgcaaagac agcaccagcc tgagccccgc ccgcgggcac agcgtctgct ccacctccag    7380
cctgtacctg caggacctca ccgccgccgc gtccgagtgc attgacccct cagtggtctt    7440
tccctacccg ctcaacgaca gcagctcgcc caaatcctgt acctcgtccg attccacggc    7500
cttctctcct tcctcggact cgctgctgtc ctccagtcc tccccacggg ccagccctga     7560 gccccctagtg ctgcatgagg agacaccgcc caccaccagc agcgactctg aagaagagca    7620
agaagatgag gaagaaattg atgtggtgtc tgtggagaag aggcaaaccc ctgccaagag    7680
gtcggagtcg ggctcatctc catcccgagg ccacagcaaa cctccgcaca gcccactggt    7740
cctcaagagg tgccacgtct ccactcacca gcacaactac gccgcacccc cctccacaag    7800
```

```
gaaggactat ccagctgcca agagggccaa gttggacagt ggcagggtcc tgaagcagat   7860
cagcaacaac cgcaagtgct ccagccccag gtcctcagac acggaggaaa acgacaagag   7920
gcggacacac aacgtcttgg aacgtcagag gaggaacgag ctgaagcgca gcttttttgc   7980
cctgcgtgac cagatccctg aattggaaaa caacgaaaag gcccccaagg tagtgatcct   8040
caaaaaagcc accgcctaca tcctgtccat tcaagcagac gagcacaagc tcacctctga   8100
aaaggactta ttgaggaaac gacgagaaca gttgaaacac aaactcgaac agcttcgaaa   8160
ctctggtgca taaatcgata gatcctaatc aacctctgga ttacaaaatt tgtgaaagat   8220
tgactggtat tcttaactat gttgctcctt ttacgctatg tggatacgct gctttaatgc   8280
ctttgtatca tgctattgct tcccgtatgg cttcatttt ctcctccttg tataaatcct   8340
ggttgctgtc tctttatgag gagttgtggc ccgttgtcag gcaacgtggc gtggtgtgca   8400
ctgtgtttgc tgacgcaacc cccactggtt ggggcattgc caccacctgt cagctccttt   8460
ccggactttt cgctttcccc ctccctattg ccacggcgga actcatcgcc gcctgccttg   8520
cccgctgctg gacaggggct cggctgttgg gcactgacaa ttccgtggtg ttgtcgggga   8580
aatcatcgtc ctttccttgg ctgctcgcct gtgttgccac ctggattctg cgcgggacgt   8640
ccttctgcta cgtcccttcg gccctcaatc cagcggacct tccttcccgc ggcctgctgc   8700
cggctctgcg gcctcttccg cgtcttcgcc ttcgccctca gacgagtcgg atctcccttt   8760
gggccgcctc cccgcctggt acctttaaga ccaatgactt acaaggcagc tgtagatctt   8820 agccacttt taaagaaaa gggggactg aagggctaa ttcactccca acgaagacaa   8880
gatcacctgc aggacaggcg cgccctgctt tttgcttgta ctgggtctct ctggttagac   8940
cagatctgag cctgggagct ctctggctaa ctagggaacc cactgcttaa gcctcaataa   9000
agcttgcctt gagtgcttca agtagtgtgt gcccgtctgt tgtgtgactc tggtaactag   9060
agatccctca gacccttta gtcagtgtgg aaaatctcta gcacccgggc gattaaggaa   9120
agggctagat cattcttgaa gacgaaaggg cctcgtgata cgcctatttt tataggttaa   9180
tgtcatgata ataatggttt cttagacgtc aggtggcact tttcggggaa atgtgcgcgg   9240 aaccccctatt tgtttatttt tctaaataca ttcaaatatg tatccgctca tgagacaata   9300
accctgataa atgcttcaat aatattgaaa aaggaagagt atgagtattc aacatttccg   9360
tgtcgccctt attcccttt ttgcggcatt ttgccttcct gttttgctc acccagaaac   9420 gctggtgaaa gtaaaagatg ctgaagatca gttgggtgca cgagtgggtt acatcgaact   9480
ggatctcaac agcggtaaga tccttgagag ttttcgcccc gaagaacgtt ttccaatgat   9540
gagcactttt aaagttctgc tatgtggcgc ggtattatcc cgtgttgacg ccgggcaaga   9600
gcaactcggt cgccgcatac actattctca gaatgacttg gttgagtact caccagtcac   9660
agaaaagcat cttacggatg gcatgacagt aagagaatta tgcagtgctg ccataaccat   9720
gagtgataac actgcggcca acttacttct gacaacgatc ggaggaccga aggagctaac   9780
cgcttttttg cacaacatgg ggatcatgt aactcgcctt gatcgttggg aaccggagct   9840
gaatgaagcc ataccaaacg acgagcgtga ccaccacgatg cctgtagcaa tggcaacaac   9900
gttgcgcaaa ctattaactg gcgaactact tactctagct tcccggcaac aattaataga   9960
ctggatggag gcggataaag ttgcaggacc acttctgcgc tcggcccttc cggctggctg  10020
gtttattgct gataaatctg gagccggtga gcgtgggtct cgcggtatca ttgcagcact  10080
ggggccagat ggtaagccct cccgtatcgt agttatctac acgacgggga gtcaggcaac  10140
```

| | | | | |
|---|---|---|---|---|
| tatggatgaa | cgaaatagac | agatcgctga | gataggtgcc | tcactgatta agcattggta | 10200 |
| actgtcagac | caagtttact | catatatact | ttagattgat | ttaaaacttc attttaatt | 10260 |
| taaaaggatc | taggtgaaga | tccttttga | taatctcatg | accaaaatcc cttaacgtga | 10320 |
| gttttcgttc | cactgagcgt | cagacccgt | agaaaagatc | aaaggatctt cttgagatcc | 10380 |
| ttttttctg | cgcgtaatct | gctgcttgca | acaaaaaaa | ccaccgctac cagcggtggt | 10440 |
| ttgtttgccg | gatcaagagc | taccaactct | ttttccgaag | gtaactggct tcagcagagc | 10500 |
| gcagatacca | aatactgttc | ttctagtgta | gccgtagtta | ggccaccact tcaagaactc | 10560 |
| tgtagcaccg | cctacatacc | tcgctctgct | aatcctgtta | ccagtggctg ctgccagtgg | 10620 |
| cgataagtcg | tgtcttaccg | ggttggactc | aagacgatag | ttaccggata aggcgcagcg | 10680 |
| gtcgggctga | acggggggtt | cgtgcacaca | gcccagcttg | gagcgaacga cctacaccga | 10740 |
| actgagatac | ctacagcgtg | agctatgaga | aagcgccacg | cttcccgaag ggagaaaggc | 10800 |
| ggacaggtat | ccggtaagcg | gcagggtcgg | aacaggagag | cgcacgaggg agcttccagg | 10860 |
| gggaaacgcc | tggtatcttt | atagtcctgt | cgggtttcgc | cacctctgac ttgagcgtcg | 10920 |
| atttttgtga | tgctcgtcag | gggggcggag | cctatggaaa | aacgccagca acgcggcctt | 10980 |
| tttacggttc | ctggccttt | gctggccttt | tgctcacatg | ttctttcctg cgttatcccc | 11040 |
| tgattctgtg | gataaccgta | ttaccgcctt | tgagtgagct | gataccgctc gccgcagccg | 11100 |
| aacgaccgag | cgcagcgagt | cagtgagcga | ggaagcggaa | gagcgcccaa tacgcaaacc | 11160 |
| gcctctcccc | gcgcgttggc | cgattcatta | atgcagcaag | ctcatggctg actaattttt | 11220 |
| tttatttatg | cagaggccga | ggccgcctcg | gcctctgagc | tattccagaa gtagtgagga | 11280 |
| ggcttttttg | gaggcctagg | cttttgcaaa | aagctccccg | tggcacgaca ggtttcccga | 11340 |
| ctggaaagcg | ggcagtgagc | gcaacgcaat | taatgtgagt | tagctcactc attaggcacc | 11400 |
| ccaggcttta | cactttatgc | ttccggctcg | tatgttgtgt | ggaattgtga gcggataaca | 11460 |
| atttcacaca | ggaaacagct | atgacatgat | tacgaatttc | acaaataaag cattttttc | 11520 |
| actgcattct | agttgtggtt | tgtccaaact | catcaatgta | tcttatcatg tctggatcaa | 11580 |
| ctggataact | caagctaacc | aaaatcatcc | caaacttccc | accccatacc ctattaccac | 11640 |
| tgccaattac | ctgtggtttc | atttactcta | aacctgtgat | tcctctgaat tattttcatt | 11700 |
| ttaaagaaat | tgtatttgtt | aaatatgtac | tacaaactta | gtagt | 11745 |

<210> SEQ ID NO 24
<211> LENGTH: 12472
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 24

| | | | | |
|---|---|---|---|---|
| tggaagggct | aattcactcc | caagaagac | aagatatcct | tgatctgtgg atctaccaca | 60 |
| cacaaggcta | cttccctgat | tagcagaact | acacaccagg | gccaggggtc agatatccac | 120 |
| tgacctttgg | atggtgctac | aagctagtac | cagttgagcc | agataaggta gaagaggcca | 180 |
| ataaaggaga | gaacaccagc | ttgttacacc | ctgtgagcct | gcatgggatg gatgacccgg | 240 |
| agagagaagt | gttagagtgg | aggtttgaca | gccgcctagc | atttcatcac gtggcccgag | 300 |
| agctgcatcc | ggagtacttc | aagaactgct | gatatcgagc | ttgctacaag gactttccg | 360 |
| ctggggactt | tccagggagg | cgtggcctgg | gcggactgg | ggagtggcga gccctcagat | 420 |

```
cctgcatata agcagctgct ttttgcctgt actgggtctc tctggttaga ccagatctga    480
gcctgggagc tctctggcta actagggaac ccactgctta agcctcaata aagcttgcct    540
tgagtgcttc aagtagtgtg tgcccgtctg ttgtgtgact ctggtaacta gagatccctc    600 agacccttt agtcagtgtg gaaaatctct agcagtggcg cccgaacagg gacttgaaag    660
cgaaagggaa accagaggag ctctctcgac gcaggactcg gcttgctgaa gcgcgcacgg    720
caagaggcga gggcggcga ctggtgagta cgccaaaaat tttgactagc ggaggctaga    780
aggagagaga tgggtgcgag agcgtcagta ttaagcgggg gagaattaga tcgcgatggg    840
aaaaaattcg gttaaggcca gggggaaaga aaaaatataa attaaaacat atagtatggg    900
caagcaggga gctagaacga ttcgcagtta atcctggcct gttagaaaca tcagaaggct    960
gtagacaaat actgggacag ctacaaccat cccttcagac aggatcagaa gaacttagat   1020
cattatataa tacagtagca accctctatt gtgtgcatca aaggatagag ataaaagaca   1080
ccaaggaagc tttagacaag atagaggaag agcaaaacaa aagtaagacc accgcacagc   1140
aagcggccgg ccgctgatct tcagacctgg aggaggagat atgagggaca attggagaag   1200
tgaattatat aaatataaag tagtaaaaat tgaaccatta ggagtagcac ccaccaaggc   1260
aaagagaaga gtggtgcaga gagaaaaaag agcagtggga ataggagctt tgttccttgg   1320
gttcttggga gcagcaggaa gcactatggg cgcagcgtca atgacgctga cggtacaggc   1380
cagacaatta ttgtctggta tagtgcagca gcagaacaat ttgctgaggg ctattgaggc   1440
gcaacagcat ctgttgcaac tcacagtctg gggcatcaag cagctccagg caagaatcct   1500
ggctgtggaa agatacctaa aggatcaaca gctcctgggg atttggggtt gctctggaaa   1560
actcatttgc accactgctg tgccttggaa tgctagttgg agtaataaat ctctggaaca   1620
gatttggaat cacacgacct ggatggagtg ggacagagaa attaacaatt acacaagctt   1680
aatacactcc ttaattgaag aatcgcaaaa ccagcaagaa aagaatgaac aagaattatt   1740
ggaattagat aaatgggcaa gtttgtggaa ttggtttaac ataacaaatt ggctgtggta   1800
tataaaatta ttcataatga tagtaggagg cttggtaggt ttaagaatag ttttgctgt   1860 actttctata gtgaatagag ttaggcaggg atattcacca ttatcgtttc agacccacct   1920
cccaaccccg aggggacccg acaggcccga aggaatagaa gaagaaggtg gagagagaga   1980
cagagacaga tccattcgat tagtgaacgg atctcgacgg tatcgccgaa ttcacaaatg   2040
gcagtattca tccacaattt taaagaaaa ggggggattg ggggtacag tgcagggaa     2100 agaatagtag acataatagc aacagacata caaactaaag aattacaaaa acaaattaca   2160
aaaattcaaa attttcgggt ttattacagg gacagcagag atccagtttg gactagtcgt   2220
gaggctccgg tgcccgtcag tgggcagagc gcacatcgcc cacagtcccc gagaagttgg   2280 ggggagggt cggcaattga accggtgcct agagaaggtg gcgcggggta aactgggaaa   2340
gtgatgtcgt gtactggctc cgccttttc ccgagggtgg gggagaaccg tatataagtg   2400
cagtagtcgc cgtgaacgtt cttttcgca acgggtttgc cgccagaaca caggtaagtg   2460
ccgtgtgtgg ttcccgcggg cctggcctct ttacgggtta tggcccttgc gtgccttgaa   2520
ttacttccac ctggctgcag tacgtgattc ttgatcccga gcttcgggtt ggaagtgggg   2580
gggagagttc gaggccttgc gcttaaggag ccccttcgcc tcgtgcttga gttgaggcct   2640
ggcctgggcg ctggggccgc cgcgtgcgaa tctggtggca ccttcgcgcc tgtctcgctg   2700
ctttcgataa gtctctagcc atttaaaatt tttgatgacc tgctgcgacg ctttttttct   2760
```

```
ggcaagatag tcttgtaaat gcgggccaag atctgcacac tggtatttcg gttttttgggg   2820 ccgcgggcgg cgacgggggcc cgtgcgtccc agcgcacatg ttcggcgagg cggggcctgc   2880
gagcgcggcc accgagaatc ggacggggt agtctcaagc tggccggcct gctctggtgc    2940
ctggcctcgc gccgccgtgt atcgcccgc cctgggcggc aaggctggcc cggtcggcac     3000
cagttgcgtg agcggaaaga tggccgcttc ccggccctgc tgcagggagc tcaaaatgga    3060
ggacgcggcg ctcgggagag cgggcgggtg agtcacccac acaaaggaaa agggccttc    3120 cgtcctcagc cgtcgcttca tgtgactcca cggagtaccg ggcgccgtcc aggcacctcg   3180
attagttctc gagcttttgg agtacgtcgt ctttaggttg gggggagggg ttttatgcga    3240
tggagtttcc ccacactgag tgggtggaga ctgaagttag gccagcttgg cacttgatgt    3300
aattctcctt ggaatttgcc cttttttgagt ttggatcttg gttcattctc aagcctcaga   3360
cagtggttca aagttttttt cttccatttc aggtgtcgtg aagcggccgc catggctgga    3420
cacctggctt cagacttcgc cttctcaccc ccaccaggtg ggggtgatgg gtcagcaggg   3480
ctggagccgg gctgggtgga tcctcgaacc tggctaagct tccaagggcc tccaggtggg   3540
cctggaatcg gaccaggctc agaggtattg gggatctccc catgtccgcc cgcatacgag   3600
ttctgcggag ggatggcata ctgtggacct caggttggac tgggcctagt cccccaagtt    3660
ggcgtggaga cttttcagcc tgagggccag gcaggagcac gagtggaaag caactcagag   3720
ggaacctcct ctgagccctg tgccgaccgc cccaatgccg tgaagttgga aaggtggaa     3780 ccaactcccg aggagtccca ggacatgaaa gccctgcaga aggagctaga acagtttgcc    3840
aagctgctga agcagaagag gatcaccttg gggtacaccc aggccgacgt ggggctcacc    3900
ctgggcgttc tctttggaaa ggtgttcagc cagaccacca tctgtcgctt cgaggccttg   3960
cagctcagcc ttaagaacat gtgtaagctg cggcccctgc tggagaagtg ggtggaggaa    4020
gccgacaaca atgagaacct tcaggagata tgcaaatcgg agaccctggt gcaggcccgg    4080
aagagaaagc gaactagcat tgagaaccgt gtgaggtgga gtctggagac catgtttctg   4140
aagtgcccga agccctccct acagcagatc actcacatcg ccaatcagct gggctagag    4200 aaggatgtgt tcgagtatg gttctgtaac cggcgccaga agggcaaaag atcaagtatt    4260
gagtattccc aacgagaaga gtatgaggct acagggacac cttcccagg gggggctgta    4320 tcctttcctc tgcccccagg tccccacttt ggcaccccag gctatggaag ccccccacttc   4380 accacactct actcagtccc ttttcctgag ggcgaggcct ttccctctgt tcccgtcact    4440
gctctgggct ctcccatgca ttcaaacgga agtggcgtga acagactttt gaattttgac    4500
cttctcaagt tggcggggaga cgtggagtcc aacccagggc ccatggctgt cagcgacgct   4560
ctgctcccgt ccttctccac gttcgcgtcc ggccggcgg aagggagaa gacactgcgt     4620 ccagcaggtg ccccgactaa ccgttggcgt gaggaactct ctcacatgaa gcgacttccc   4680
ccacttcccg gccgcccta cgacctggcg gcgacggtgg ccacagacct ggagagtggc    4740
ggagctggtg cagcttgcag cagtaacaac ccggccctcc tagcccggag ggagaccgag   4800
gagttcaacg acctcctgga cctagacttt atccttttcca actcgctaac ccaccaggaa   4860
tcggtggccg ccaccgtgac cacctcggcg tcagcttcat cctcgtcttc cccagcgagc   4920
agcggccctg ccagcgcgcc ctccacctgc agcttcagct atccgatccg ggccgggggt   4980
gacccgggcg tggctgccag caacacaggt gagggctcc tctacagccg agaatctgcg    5040
ccacctccca cggccccctt caacctggcg gacatcaatg acgtgagccc ctcgggcggc   5100
ttcgtggctg agctcctgcg gccggagttg gacccagtat acattccgcc acagcagcct   5160
```

```
cagccgccag gtggcgggct gatgggcaag tttgtgctga aggcgtctct gaccacccct    5220
ggcagcgagt acagcagccc ttcggtcatc agtgttagca aaggaagccc agacggcagc    5280
caccccgtgg tagtggcgcc ctacagcggt ggcccgccgc gcatgtgccc caagattaag    5340
caagaggcgg tcccgtcctg cacggtcagc cggtccctag aggcccattt gagcgctgga    5400
ccccagctca gcaacggcca ccggcccaac acacacgact tcccctgggg cggcagctc     5460 cccaccagga ctaccctac actgagtccc gaggaactgc tgaacagcag ggactgtcac     5520
cctggcctgc ctcttccccc aggattccat ccccatccgg gcccaacta ccctcctttc     5580 ctgccagacc agatgcagtc acaagtcccc tctctccatt atcaagagct catgccaccg    5640
ggttcctgcc tgccagagga gcccaagcca agagggggaa gaaggtcgtg gccccggaaa    5700
agaacagcca cccacacttg tgactatgca ggctgtggca aaacctatac caagagttct    5760
catctcaagg cacacctgcg aactcacaca ggcgagaaac cttaccactg tgactgggac    5820
ggctgtgggt ggaaattcgc ccgctccgat gaactgacca ggcactaccg caaacacaca    5880
gggcaccggc cctttcagtg ccagaagtgt gacagggcct tttccaggtc ggaccacctt    5940
gccttacaca tgaagaggca ctttttaaaga tccctccccc cccctaacg ttactggccg     6000 aagccgcttg gaataaggcc ggtgtgcgtt tgtctatatg ttattttcca ccatattgcc    6060
gtcttttggc aatgtgaggg cccggaaacc tggccctgtc ttcttgacga gcattcctag    6120
gggtctttcc cctctcgcca aaggaatgca aggtctgttg aatgtcgtga aggaagcagt    6180
tcctctggaa gcttcttgaa gacaaacaac gtctgtagcg accctttgca ggcagcggaa    6240
ccccccacct ggcgacaggt gcctctgcgg ccaaaagcca cgtgtataag atacacctgc    6300
aaaggcggca aaccccagt gccacgttgt gagttggata gttgtggaaa gagtcaaatg      6360
gctctcctca agcgtattca acaagggggct gaaggatgcc cagaaggtac ccattgtat     6420 gggatctgat ctggggcctc ggtgcacatg ctttacatgt gtttagtcga ggttaaaaaa    6480
acgtctaggc ccccccgaacc acggggacgt ggttttcctt tgaaaacac gatgataata    6540 tggccacaca tatgatgtat aacatgatgg agacggagct gaagccgccg ggcccgcagc    6600
aagcttcggg gggcggcggc ggaggaggca acgccacggc ggcggcgacc ggcggcaacc    6660
agaagaacag cccggaccgc gtcaagaggc ccatgaacgc cttcatggta tggtcccggg    6720
ggcagcggcg taagatggcc caggagaacc ccaagatgca caactcggag atcagcaagc    6780
gcctgggcgc ggagtggaaa cttttgtccg agaccgagaa gcggccgttc atcgacgagg    6840
ccaagcggct gcgcgctctg cacatgaagg agcacccgga ttataaatac cggccgcggc    6900
ggaaaaccaa gacgctcatg aagaaggata agtacacgct tcccggaggc ttgctggccc    6960
ccggcgggaa cagcatggcg agcggggttg gggtgggcgc cggcctgggt gcgggcgtga    7020
accagcgcat ggacagctac gcgcacatga acggctggag caacggcagc tacagcatga    7080
tgcaggagca gctgggctac ccgcagcacc cgggcctcaa cgctcacggc gcggcacaga    7140
tgcaaccgat gcaccgctac gacgtcagcg ccctgcagta caactccatg accagctcgc    7200
agacctacat gaacggctcg cccacctaca gcatgtccta ctcgcagcag ggcacccccg    7260
gtatggcgct gggctccatg ggctctgtgg tcaagtccga ggccagctcc agccccccg     7320 tggttaccct ttcctcccac tccagggcgc cctgccaggc cggggacctc cgggacatga    7380
tcagcatgta cctccccggc gccgaggtgc cggagcccgc tgcgcccagt agactgcaca    7440
tggcccagca ctaccagagc ggcccggtgc ccggcacggc cattaacggc acactgcccc    7500
```

```
tgtcgcacat gggtagtggg caatgtacta actacgcttt gttgaaactc gctggcgatg    7560
ttgaaagtaa ccccggtcct atgcccctca acgtgaactt caccaacagg aactatgacc    7620
tcgactacga ctccgtacag ccctatttca tctgcgacga ggaagagaat ttctatcacc    7680
agcaacagca gagcgagctg cagccgcccg cgcccagtga ggatatctgg aagaaattcg    7740
agctgcttcc cacccgccc ctgtccccga gccgcgctc cgggctctgc tctccatcct    7800
atgttgcggt cgctacgtcc ttctccccaa gggaagacga tgacggcggc ggtggcaact    7860
tctccaccgc cgatcagctg gagatgatga ccgagttact tggaggagac atggtgaacc    7920
agagcttcat ctgcgatcct gacgacgaga ccttcatcaa gaacatcatc atccaggact    7980
gtatgtggag cggtttctca gccgctgcca agctggtctc ggagaagctg gcctcctacc    8040
aggctgcgcg caaagacagc accagcctga gccccgcccg cgggcacagc gtctgctcca    8100
cctccagcct gtacctgcag gacctcaccg ccgccgcgtc cgagtgcatt gacccctcag    8160 tggtcttttcc ctaccgctc aacgacagca gctcgcccaa atcctgtacc tcgtccgatt    8220
ccacggcctt ctctccttcc tcggactcgc tgctgtcctc cgagtcctcc ccacgggcca    8280
gccctgagcc cctagtgctg catgaggaga caccgcccac caccagcagc gactctgaag    8340
aagagcaaga agatgaggaa gaaattgatg tggtgtctgt ggagaagagg caaacccctg    8400
ccaagaggtc ggagtcgggc tcatctccat cccgaggcca cagcaaacct ccgcacagcc    8460
cactggtcct caagaggtgc cacgtctcca ctcaccagca caactacgcc gcaccccct    8520 ccacaaggaa ggactatcca gctgccaaga gggccaagtt ggacagtggc agggtcctga    8580
agcagatcag caacaaccgc aagtgctcca gccccaggtc ctcagacacg gaggaaaacg    8640
acaagaggcg gacacacaac gtcttggaac gtcagaggag gaacgagctg aagcgcagct    8700
tttttgccct gcgtgaccag atccctgaat tggaaaacaa cgaaaaggcc ccaaggtag    8760 tgatcctcaa aaaagccacc gcctacatcc tgtccattca agcagacgag cacaagctca    8820
cctctgaaaa ggacttattg aggaaacgac gagaacagtt gaaacacaaa ctcgaacagc    8880
ttcgaaactc tggtgcataa atcgatagat cctaatcaac ctctggatta caaaatttgt    8940
gaaagattga ctggtattct taactatgtt gctccttta cgctatgtgg atacgctgct    9000
ttaatgcctt tgtatcatgc tattgcttcc cgtatggctt tcattttctc ctccttgtat    9060
aaatcctggt tgctgtctct ttatgaggag ttgtggcccg ttgtcaggca acgtggcgtg    9120
gtgtgcactg tgtttgctga cgcaaccccc actggttggg gcattgccac cacctgtcag    9180
ctcctttccg ggactttcgc tttccccctc cctattgcca cggcggaact catcgccgcc    9240
tgccttgccc gctgctggac aggggctcgg ctgttgggca ctgacaattc cgtggtgttg    9300
tcggggaaat catcgtcctt ccttggctg ctcgcctgtg ttgccacctg gattctgcgc    9360
gggacgtcct tctgctacgt cccttcggcc ctcaatccag cggaccttcc ttcccgcggc    9420
ctgctgccgg ctctgcggcc tcttccgcgt cttcgccttc gccctcagac gagtcggatc    9480 tcccttgg ccgcctcccc gcctggtacc tttaagacca atgacttaca aggcagctgt    9540
agatcttagc cacttttta aagaaaaggg gggactggaa gggctaattc actcccaacg    9600
aagacaagat cacctgcagg acaggcgcgc cctgcttttt gcttgtactg ggtctctctg    9660
gttagaccag atctgagcct gggagctctc tggctaacta gggaacccac tgcttaagcc    9720
tcaataaagc ttgccttgag tgcttcaagt agtgtgtgcc cgtctgttgt gtgactctgg    9780
taactagaga tccctcagac ccttttagtc agtgtggaaa atctctagca cccgggcgat    9840
taaggaaagg gctagatcat tcttgaagac gaaagggcct cgtgatacgc ctattttat    9900
```

```
aggttaatgt catgataata atggtttctt agacgtcagg tggcactttt cggggaaatg    9960
tgcgcggaac ccctatttgt ttattttttct aaatacattc aaatatgtat ccgctcatga  10020
gacaataacc ctgataaatg cttcaataat attgaaaaag gaagagtatg agtattcaac  10080
atttccgtgt cgcccttatt ccctttttg cggcattttg ccttcctgtt tttgctcacc    10140
cagaaacgct ggtgaaagta aaagatgctg aagatcagtt gggtgcacga gtgggttaca  10200
tcgaactgga tctcaacagc ggtaagatcc ttgagagttt cgccccgaa gaacgttttc    10260
caatgatgag cacttttaaa gttctgctat gtggcgcggt attatcccgt gttgacgccg  10320
ggcaagagca actcggtcgc cgcatacact attctcagaa tgacttggtt gagtactcac  10380
cagtcacaga aaagcatctt acggatggca tgacagtaag agaattatgc agtgctgcca  10440
taaccatgag tgataacact gcggccaact tacttctgac aacgatcgga ggaccgaagg  10500
agctaaccgc ttttttgcac aacatggggg atcatgtaac tcgccttgat cgttgggaac  10560
cggagctgaa tgaagccata ccaaacgacg agcgtgacac cacgatgcct gtagcaatgg  10620
caacaacgtt gcgcaaacta ttaactggcg aactacttac tctagcttcc cggcaacaat  10680
taatagactg gatggaggcg gataaagttg caggaccact tctgcgctcg gcccttccgg  10740
ctggctggtt tattgctgat aaatctggag ccggtgagcg tgggtctcgc ggtatcattg  10800
cagcactggg gccagatggt aagccctccc gtatcgtagt tatctacacg acggggagtc  10860
aggcaactat ggatgaacga aatagacaga tcgctgagat aggtgcctca ctgattaagc  10920
attggtaact gtcagaccaa gtttactcat atatacttta gattgattta aaacttcatt  10980
tttaatttaa aaggatctag gtgaagatcc tttttgataa tctcatgacc aaaatccctt  11040
aacgtgagtt ttcgttccac tgagcgtcag accccgtaga aaagatcaaa ggatcttctt  11100
gagatccttt ttttctgcgc gtaatctgct gcttgcaaac aaaaaaacca ccgctaccag  11160
cggtggtttg tttgccggat caagagctac caactctttt tccgaaggta actggcttca  11220
gcagagcgca gataccaaat actgttcttc tagtgtagcc gtagttaggc caccacttca  11280
agaactctgt agcaccgcct acatacctcg ctctgctaat cctgttacca gtggctgctg  11340
ccagtggcga taagtcgtgt cttaccgggt tggactcaag acgatagtta ccggataagg  11400
cgcagcggtc gggctgaacg gggggttcgt gcacacagcc cagcttggag cgaacgacct  11460
acaccgaact gagataccta cagcgtgagc tatgagaaag cgccacgctt cccgaaggga  11520
gaaaggcgga caggtatccg gtaagcggca gggtcggaac aggagagcgc acgagggagc  11580
ttccaggggg aaacgcctgg tatctttata gtcctgtcgg gtttcgccac ctctgacttg  11640
agcgtcgatt tttgtgatgc tcgtcagggg gcggagccta tggaaaaac gccagcaacg  11700
cggccttttt acgttcctg gccttttgct ggccttttgc tcacatgttc tttcctgcgt  11760
tatcccctga ttctgtggat aaccgtatta ccgcctttga gtgagctgat accgctcgcc  11820
gcagccgaac gaccgagcgc agcgagtcag tgagcgagga agcggaagag cgcccaatac  11880
gcaaaccgcc tctccccgcg cgttggccga ttcattaatg cagcaagctc atggctgact  11940
aatttttttt attatgcag aggccgaggc cgcctcggcc tctgagctat tccagaagta  12000
gtgaggaggc tttttggag gcctaggctt ttgcaaaaag ctccccgtgg cacgacaggt  12060
ttcccgactg gaaagcgggc agtgagcgca acgcaattaa tgtgagttag ctcactcatt  12120
aggcacccca ggctttacac tttatgcttc cggctcgtat gttgtgtgga attgtgagcg  12180
gataacaatt tcacacagga aacagctatg acatgattac gaatttcaca aataaagcat  12240
```

```
tttttttcact gcattctagt tgtggtttgt ccaaactcat caatgtatct tatcatgtct    12300
ggatcaactg gataactcaa gctaaccaaa atcatcccaa acttcccacc ccatacccta    12360
ttaccactgc caattacctg tggtttcatt tactctaaac ctgtgattcc tctgaattat    12420
tttcatttta aagaaattgt atttgttaaa tatgtactac aaacttagta gt            12472
```

<210> SEQ ID NO 25
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 25

```
ataacttcgt atagcataca ttatacgaag ttat                                34
```

<210> SEQ ID NO 26
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 26

```
tctttccacc aggcccccgg ctc                                            23
```

<210> SEQ ID NO 27
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 27

```
cgtggtgagc atcttcggag tgg                                            23
```

<210> SEQ ID NO 28
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 28

```
caggtgtttg agggtagctc                                                20
```

<210> SEQ ID NO 29
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 29

```
acgagtggca gtttcttctt ggga                                           24
```

```
<210> SEQ ID NO 30
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 30
gaagtctggt tccttggcag gatg                                              24

<210> SEQ ID NO 31
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 31
gttccaacct gtgcctcgcg tctt                                              24

<210> SEQ ID NO 32
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 32
tgtggggccc tgaaaggcga gctgagat                                          28

<210> SEQ ID NO 33
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 33
tgctgcggtc caggccatca agag                                              24

<210> SEQ ID NO 34
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 34
ccattagggg ccatcatcgc tttc                                              24

<210> SEQ ID NO 35
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

```
<400> SEQUENCE: 35
atggacgcaa ctgtgaacat gatgttcgca                                          30

<210> SEQ ID NO 36
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 36
attcttcgtt gtcaagccgc caaagtggag                                          30

<210> SEQ ID NO 37
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 37
acgagcacaa gctcacctct                                                     20

<210> SEQ ID NO 38
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 38
tcagcaaaca cagtgcacac c                                                   21

<210> SEQ ID NO 39
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 39
cgcgcaggta ccataacttc gtataatgta tgctatacga agttatgg                      48

<210> SEQ ID NO 40
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 40
cgcgccataa cttcgtatag catacattat acgaagttat ggtacctg                      48

<210> SEQ ID NO 41
<211> LENGTH: 77
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic primer"

<400> SEQUENCE: 41
ctttgttgaa actcgctggc gatgttgaaa gtaaccccgg tcctatggtg agcaagggcg      60
aggaggataa catggcc                                                    77

<210> SEQ ID NO 42
<211> LENGTH: 37
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 42
atcgatttac ttgtacagct cgtccatgcc gccggtg                              37

<210> SEQ ID NO 43
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 43
gtaagtaaga attgaggagt gg                                              22

<210> SEQ ID NO 44
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 44
tccaaaccca cctaaaaacc                                                 20

<210> SEQ ID NO 45
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 45
gatggttgag tgggttgtaa gg                                              22

<210> SEQ ID NO 46
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 46
```

```
ccaaccctac taacccatca cc                                             22
```

<210> SEQ ID NO 47
<211> LENGTH: 2098
<212> TYPE: DNA
<213> ORGANISM: Homo sapiens

<400> SEQUENCE: 47

```
attataaatc tagagactcc aggattttaa cgttctgctg gactgagctg gttgcctcat     60
gttattatgc aggcaactca ctttatccca atttcttgat acttttcctt ctggaggtcc    120
tatttctcta acatcttcca gaaaagtctt aaagctgcct taaccttttt tccagtccac    180
ctcttaaatt ttttcctcct cttcctctat actaacatga gtgtggatcc agcttgtccc    240
caaagcttgc cttgctttga agcatccgac tgtaaagaat cttcacctat gcctgtgatt    300
tgtgggcctg aagaaaacta tccatccttg caaatgtctt ctgctgagat gcctcacacg    360
gagactgtct ctcctcttcc ttcctccatg gatctgctta ttcaggacag ccctgattct    420
tccaccagtc ccaaaggcaa acaacccact tctgcagaga gagtgtcgc aaaaaaggaa     480
gacaaggtcc cggtcaagaa acagaagacc agaactgtgt tctcttccac ccagctgtgt    540
gtactcaatg atagatttca gagacagaaa tacctcagcc tccagcagat gcaagaactc    600
tccaacatcc tgaacctcag ctacaaacag gtgaagacct ggttccagaa ccagagaatg    660
aaatctaaga ggtggcagaa aaacaactgg ccgaagaata gcaatggtgt gacgcagaag    720
gcctcagcac ctacctaccc cagcctttac tcttcctacc accagggatg cctggtgaac    780
ccgactggga accttccaat gtggagcaac cagacctgga caattcaac ctggagcaac     840
cagacccaga catccagtc ctggagcaac cactcctgga cactcagac tggtgcacc      900
caatcctgga caatcaggc ctggaacagt cccttctata ctgtggaga ggaatctctg      960
cagtcctgca tgcagttcca gccaaattct cctgccagtg acttggaggc tgccttggaa   1020
gctgctgggg aaggccttaa tgtaatacag cagaccacta gtatttag tactccacaa     1080
accatggatt tattcctaaa ctactccatg aacatgcaac ctgaagacgt gtgaagatga   1140
gtgaaactga tattactcaa tttcagtctg gacactggct gaatccttcc tctccctcc    1200
tcccatccct cataggattt tcttgttttg gaaaccacgt gttctggttt ccatgatgcc   1260
catccagtca atctcatgga gggtggagta tggttggagc ctaatcagcg aggtttcttt   1320
tttttttttt ttcctattgg atcttcctgg agaaaatact ttttttttt ttttttttga    1380
aacggagtct tgctctgtcg cccaggctgg agtgcagtgg cgcggtcttg gctcactgca   1440
agctccgtct cccgggttca cgccattctc ctgcctcagc ctcccgagca gctgggacta   1500
caggcgcccg ccacctcgcc cggctaatat tttgtatttt tagtagagac ggggtttcac   1560
tgtgttagcc aggatggtct cgatctcctg accttgtgat ccacccgcct cggcctccct   1620
aacagctggg atttacaggc gtgagccacc gcgcccgcc tagaaaagac attttaataa    1680
ccttggctgc cgtctctggc tatagataag tagatctaat actagtttgg atatctttag   1740
ggtttagaat ctaacctcaa gaataagaaa tacaagtaca aattggtgat gaagatgtat   1800
tcgtattgtt tgggattggg aggctttgct tatttttaa aaactattga ggtaaagggt    1860
taagctgtaa catacttaat tgatttctta ccgttttttgg ctctgttttg ctatatcccc  1920
taatttgttg gttgtgctaa tctttgtaga aagaggctc gtatttgctg catcgtaatg    1980
acatgagtac tgctttagtt ggtttaagtt caaatgaatg aaacaactat ttttccttta   2040
gttgatttta ccctgatttc accgagtgtt tcaatgagta aatatacagc ttaaacat     2098
```

<210> SEQ ID NO 48
<211> LENGTH: 4014
<212> TYPE: DNA
<213> ORGANISM: Homo sapiens

<400> SEQUENCE: 48

| | | | | | | |
|---|---|---|---|---|---|---|
| gtgcggggga | agatgtagca | gcttcttctc | cgaaccaacc | ctttgccttc | ggacttctcc | 60 |
| ggggccagca | gccgcccgac | caggggcccg | gggccacggg | ctcagccgac | gaccatgggc | 120 |
| tccgtgtcca | accagcagtt | tgcaggtggc | tgcgccaagg | cggcagaaga | ggcgcccgag | 180 |
| gaggcgccgg | aggacgcggc | ccgggcggcg | gacgagcctc | agctgctgca | cggtgcgggc | 240 |
| atctgtaagt | ggttcaacgt | gcgcatgggg | ttcggcttcc | tgtccatgac | cgcccgcgcc | 300 |
| ggggtcgcgc | tcgaccccc | agtggatgtc | tttgtgcacc | agagtaagct | gcacatggaa | 360 |
| gggttccgga | gcttgaagga | gggtgaggca | gtggagttca | cctttaagaa | gtcagccaag | 420 |
| ggtctggaat | ccatccgtgt | caccggacct | ggtggagtat | tctgtattgg | gagtgagagg | 480 |
| cggccaaaag | gaaagagcat | gcagaagcgc | agatcaaaag | gagacaggtg | ctacaactgt | 540 |
| ggaggtctag | atcatcatgc | caaggaatgc | aagctgccac | cccagcccaa | gaagtgccac | 600 |
| ttctgccaga | gcatcagcca | tatggtagcc | tcatgtccgc | tgaaggccca | gcagggccct | 660 |
| agtgcacagg | gaaagccaac | ctactttcga | gaggaagaag | aagaaatcca | cagccctacc | 720 |
| ctgctcccgg | aggcacagaa | ttgagccaca | atgggtgggg | gctattcttt | tgctatcagg | 780 |
| aagttttgag | gagcaggcag | agtggagaaa | gtgggaatag | ggtgcattgg | ggctagttgg | 840 |
| cactgccatg | tatctcaggc | ttgggttcac | accatcaccc | tttcttccct | ctaggtgggg | 900 |
| ggaaagggtg | agtcaaagga | actccaacca | tgctctgtcc | aaatgcaagt | gagggttctg | 960 |
| ggggcaacca | ggaggggga | atcaccctac | aacctgcata | ctttgagtct | ccatccccag | 1020 |
| aatttccagc | ttttgaaagt | ggcctggata | gggaagttgt | tttccttta | aagaaggata | 1080 |
| tataataatt | cccatgccag | agtgaaatga | ttaagtataa | gaccagattc | atggagccaa | 1140 |
| gccactacat | tctgtggaag | gagatctctc | aggagtaagc | attgtttttt | tttcacatct | 1200 |
| tgtatcctca | tacccacttt | tgggataggg | tgctggcagc | tgtcccaagc | aatgggtaat | 1260 |
| gatgatggca | aaaagggtgt | ttgggggaac | agctgcagac | ctgctgctct | atgctcaccc | 1320 |
| ccgcccatt | ctgggccaat | gtgattttat | ttatttgctc | ccttggatac | tgcaccttgg | 1380 |
| gtcccacttt | ctccaggatg | ccaactgcac | tagctgtgtg | cgaatgacgt | atcttgtgca | 1440 |
| ttttaacttt | ttttccttaa | tataaatatt | ctggttttgt | attttttgtat | attttaatct | 1500 |
| aaggccctca | tttcctgcac | tgtgttctca | ggtacatgag | caatctcagg | gatagccagc | 1560 |
| agcagctcca | ggtctgcgca | gcaggaatta | cttttttgttg | ttttttgccac | cgtggagagc | 1620 |
| aactatttgg | agtgcacagc | ctattgaact | acctcatttt | tgccaataag | agctggcttt | 1680 |
| tctgccatag | tgtcctcttg | aaaccccctc | tgccttgaaa | atgttttatg | ggagactagg | 1740 |
| ttttaactgg | gtggcccat | gacttgattg | ccttctactg | gaagattggg | aattagtcta | 1800 |
| aacaggaaat | ggtggtacac | agaggctagg | agaggctggg | cccggtgaaa | aggccagaga | 1860 |
| gcaagccaag | attaggtgag | ggttgtctaa | tcctatggca | caggacgtgc | tttacatctc | 1920 |
| cagatctgtt | cttcaccaga | ttaggttagg | cctaccatgt | gccacagggt | gtgtgtgtgt | 1980 |
| ttgtaaaact | agagttgcta | aggataagtt | taaagaccaa | taccctgta | cttaatcctg | 2040 |
| tgctgtcgag | ggatggatat | atgaagtaag | gtgagatcct | taacctttca | aaattttcgg | 2100 |

| | |
|---|---|
| gttccaggga gacacacaag cgagggtttt gtggtgcctg gagcctgtgt cctgccctgc | 2160 |
| tacagtagtg attaatagtg tcatggtagc taaaggagaa aaaggggtt tcgtttacac | 2220 |
| gctgtgagat caccgcaaac ctaccttact gtgttgaaac gggacaaatg caatagaacg | 2280 |
| cattgggtgg tgtgtgtctg atcctgggtt cttgtctccc ctaaatgctg cccccaagt | 2340 |
| tactgtattt gtctgggctt tgtaggactt cactacgttg attgctaggt ggcctagttt | 2400 |
| gtgtaaatat aatgtattgg tcttctccg tgttctttgg gggttttgtt tacaaacttc | 2460 |
| tttttgtatt gagagaaaaa tagccaaagc atctttgaca gaaggttctg caccaggcaa | 2520 |
| aaagatctga acattagtt tggggggccc tcttcttaaa gtgggatct tgaaccatcc | 2580 |
| tttcttttgt attccccttc ccctattacc tattagacca gatcttctgt cctaaaaact | 2640 |
| tgtcttctac cctgccctct tttcgttca cccccaaaag aaaacttaca cacccacaca | 2700 |
| catacacatt tcatgcttgg agtgtctcca caactcttaa atgatgtatg caaaaatact | 2760 |
| gaagctagga aaaccctcca tcccttgttc ccaacctcct aagtcaagac cattaccatt | 2820 |
| tctttctttc tttttttttt tttttaaaa tggagtctca ctgtgtcacc caggctggag | 2880 |
| tgcagtggca tgatcggctc actgcagcct ctgcctcttg ggttcaagtg attctcctgc | 2940 |
| ctcagcctcc tgagtagctg ggatttcagg cacccgccac actcagctaa tttttgtatt | 3000 |
| tttagtagag acggggtttc accatgttgt ccaggctggt ctggaactcc tgacctcagg | 3060 |
| tgatctgccc accttggctt cccaaagtgc tgggattaca ggcatgagcc accatgctgg | 3120 |
| gccaaccatt tcttggtgta ttcatgccaa acacttaaga cactgctgta gcccaggcgc | 3180 |
| ggtggctcac acctgtaatc ccagcacttt ggaaggctga ggcgggcgga tcacaaggtc | 3240 |
| acgagttcaa aactatcctg gccaacacag tgaaacccg tctctactaa aatacaaaaa | 3300 |
| aattagccgg gtgtggtggt gcatgccttt agtcctagct attcaggagg ctgaggcagg | 3360 |
| ggaatcgctt gaacccgaga ggcagaggtt gcagtgagct gagatcgcac cactgcactc | 3420 |
| cagcctggtt acagagcaag actctgtctc aaacaaaaca aaacaaaaca aaacacact | 3480 |
| actgtatttt ggatggatca aacctcctta attttaattt ctaatcctaa agtaaagaga | 3540 |
| tgcaattggg ggccttccat gtagaaagtg gggtcaggag gccaagaaag gaatatgaa | 3600 |
| tgtatatcca agtcactcag gaactttat gcaggtgcta gaaactttat gtcaaagtgg | 3660 |
| ccacaagatt gtttaatagg agacgaacga atgtaactcc atgtttactg ctaaaaacca | 3720 |
| aagctttgtg taaaatcttg aatttatggg gcgggagggt aggaaagcct gtacctgtct | 3780 |
| gttttttcc tgatcctttt ccctcattcc tgaactgcag gagactgagc ccctttgggc | 3840 |
| tttggtgacc ccatcactgg ggtgtgttta tttgatggtt gatttgctg tactgggtac | 3900 |
| ttcctttccc attttctaat catttttttaa cacaagctga ctcttccctt cccttctcct | 3960 |
| ttccctggga aaatacaatg aataaataaa gacttattgg tacgcaaact gtca | 4014 |

<210> SEQ ID NO 49
<211> LENGTH: 711
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 49

| | |
|---|---|
| atggtgagca agggcgagga ggataacatg gccatcatca aggagttcat gcgcttcaag | 60 |
| gtgcacatgg agggctccgt gaacggccac gagttcgaga tcgagggcga gggcgagggc | 120 |

```
cgcccctacg agggcaccca gaccgccaag ctgaaggtga ccaagggtgg cccccctgccc    180 ttcgcctggg acatcctgtc ccctcagttc atgtacggct ccaaggccta cgtgaagcac    240
cccgccgaca tccccgacta cttgaagctg tccttccccg agggcttcaa gtgggagcgc    300
gtgatgaact tcgaggacgg cggcgtggtg accgtgaccc aggactcctc cctgcaggac    360
ggcgagttca tctacaaggt gaagctgcgc ggcaccaact cccctccga cggccccgta    420 atgcagaaga agaccatggg ctgggaggcc tcctccgagc ggatgtaccc cgaggacggc    480
gccctgaagg gcgagatcaa gcagaggctg aagctgaagg acggcggcca ctacgacgct    540
gaggtcaaga ccacctacaa ggccaagaag cccgtgcagc tgcccggcgc ctacaacgtc    600
aacatcaagt tggacatcac ctcccacaac gaggactaca ccatcgtgga acagtacgaa    660
cgcgccgagg gccgccactc caccggcggc atggacgagc tgtacaagta a             711

<210> SEQ ID NO 50
<211> LENGTH: 11911
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 50
tggaagggct aattcactcc caagaagac aagatatcct tgatctgtgg atctaccaca     60
cacaaggcta cttccctgat tagcagaact acacaccagg gccagggtc agatatccac    120 tgacctttgg atggtgctac aagctagtac cagttgagcc agataaggta gaagaggcca    180
ataaaggaga gaacaccagc ttgttacacc ctgtgagcct gcatgggatg gatgacccgg    240
agagagaagt gttagagtgg aggtttgaca gccgcctagc atttcatcac gtggcccgag    300
agctgcatcc ggagtacttc aagaactgct gatatcgagc ttgctacaag gactttccg     360 ctggggactt tccagggagg cgtggcctgg gcgggactgg ggagtggcga gccctcagat    420
cctgcatata agcagctgct ttttgcctgt actgggtctc tctggttaga ccagatctga    480
gcctgggagc tctctggcta actagggaac ccactgctta agcctcaata aagcttgcct    540
tgagtgcttc aagtagtgtg tgcccgtctg ttgtgtgact ctggtaacta gagatccctc    600 agacccttt agtcagtgtg aaaatctct agcagtggcg cccgaacagg gacttgaaag    660
cgaaagggaa accagaggag ctctctcgac gcaggactcg gcttgctgaa gcgcgcacgg    720
caagaggcga gggcggcga ctggtgagta cgccaaaaat tttgactagc ggaggctaga    780
aggagagaga tgggtgcgag agcgtcagta ttaagcgggg gagaattaga tcgcgatggg    840
aaaaaattcg gttaaggcca ggggaaaga aaaatataa attaaacat atagtatggg     900 caagcaggga gctagaacga ttcgcagtta atcctggcct gttagaaaca tcagaaggct    960
gtagacaaat actgggacag ctacaaccat cccttcagac aggatcagaa gaacttagat   1020
cattatataa tacagtagca accctctatt gtgtgcatca aggatagag ataaaagaca   1080 ccaaggaagc tttagacaag atagaggaag agcaaaacaa agtaagacc accgcacagc   1140 aagcggccgg ccgctgatct tcagacctgg aggaggagat atgagggaca attggagaag   1200
tgaattatat aaatataaag tagtaaaaat tgaaccatta ggagtagcac ccaccaaggc   1260
aaagagaaga gtggtgcaga gagaaaaaag agcagtggga ataggagctt tgttccttgg   1320
gttcttggga gcagcaggaa gcactatggg cgcagcgtca atgacgctga cggtacaggc   1380
```

```
cagacaatta ttgtctggta tagtgcagca gcagaacaat ttgctgaggg ctattgaggc   1440
gcaacagcat ctgttgcaac tcacagtctg gggcatcaag cagctccagg caagaatcct   1500
ggctgtggaa agatacctaa aggatcaaca gctcctgggg atttggggtt gctctggaaa   1560
actcatttgc accactgctg tgccttggaa tgctagttgg agtaataaat ctctggaaca   1620
gatttggaat cacacgacct ggatggagtg ggacagagaa attaacaatt acacaagctt   1680
aatacactcc ttaattgaag aatcgcaaaa ccagcaagaa aagaatgaac aagaattatt   1740
ggaattagat aaatgggcaa gtttgtggaa ttggtttaac ataacaaatt ggctgtggta   1800
tataaaatta ttcataatga tagtaggagg cttggtaggt ttaagaatag ttttgctgt    1860 actttctata gtgaatagag ttaggcaggg atattcacca ttatcgtttc agacccacct   1920
cccaaccccg aggggacccg acaggcccga aggaatagaa gaagaaggtg gagagagaga   1980
cagagacaga tccattcgat tagtgaacgg atctcgacgg tatcgccgaa ttcacaaatg   2040
gcagtattca tccacaattt taaagaaaa gggggggattg gggggtacag tgcaggggaa    2100
agaatagtag acataatagc aacagacata caaactaaag aattacaaaa acaaattaca   2160
aaaattcaaa attttcgggt ttattacagg gacagcagag atccagtttg gactagtcgt   2220
gaggctccgg tgcccgtcag tgggcagagc gcacatcgcc cacagtcccc gagaagttgg   2280 ggggagggt cggcaattga accggtgcct agagaaggtg gcgcgggta aactgggaaa      2340 gtgatgtcgt gtactggctc cgccttttc ccgagggtgg gggagaaccg tatataagtg     2400
cagtagtcgc cgtgaacgtt cttttttcgca acgggtttgc cgccagaaca caggtaagtg   2460
ccgtgtgtgg ttcccgcggg cctggcctct ttacgggtta tggcccttgc gtgccttgaa   2520
ttacttccac ctggctgcag tacgtgattc ttgatcccga gcttcgggtt ggaagtgggt   2580
gggagagttc gaggccttgc gcttaaggag ccccttcgcc tcgtgcttga gttgaggcct   2640
ggcctgggcg ctggggccgc cgcgtgcgaa tctggtggca ccttcgcgcc tgtctcgctg   2700
cttccgataa gtctctagcc atttaaaatt tttgatgacc tgctgcgacg cttttttttct   2760 ggcaagatag tcttgtaaat gcgggccaag atctgcacac tggtatttcg gttttttgggg   2820 ccgcggggcgg cgacggggcc cgtgcgtccc agcgcacatg ttcggcgagg cggggcctgc    2880
gagcgcggcc accgagaatc ggacgggggt agtctcaagc tggccggcct gctctggtgc   2940
ctggcctcgc gccgccgtgt atcgcccgcc cctgggcggc aaggctggcc cggtcggcac   3000
cagttgcgtg agcggaaaga tggccgcttc ccggccctgc tgcagggagc tcaaaatgga   3060
ggacgcggcg ctcgggagag cgggcgggtg agtcacccac acaaaggaaa agggccttc    3120 cgtcctcagc cgtcgcttca tgtgactcca cggagtaccg ggcgccgtcc aggcacctcg   3180
attagttctc gagcttttgg agtacgtcgt ctttaggttg gggggagggg ttttatgcga   3240
tggagtttcc ccacactgag tgggtggaga ctgaagttag gccagcttgg cacttgatgt   3300
aattctcctt ggaatttgcc cttttttgagt ttggatcttg gttcattctc aagcctcaga   3360
cagtggttca agttttttt cttccatttc aggtgtcgtg aagcggccgc catggctgga   3420
cacctggctt cagacttcgc cttctcaccc ccaccaggtg ggggtgatgg gtcagcaggg   3480
ctggagccgg gctgggtgga tcctcgaacc tggctaagct tccaagggcc tccaggtggg   3540
cctggaatcg gaccaggctc agaggtattg ggatctccc catgtccgcc cgcatacgag    3600
ttctgcggag ggatggcata ctgtggacct caggttggac tgggcctagt cccccaagtt   3660
ggcgtggaga ctttgcagcc tgaggccag gcaggagcac gagtggaaag caactcagag    3720
ggaacctcct ctgagccctg tgccgaccgc cccaatgccg tgaagttgga gaaggtggaa   3780
```

-continued

```
ccaactcccg aggagtccca ggacatgaaa gccctgcaga aggagctaga acagtttgcc    3840
aagctgctga agcagaagag gatcaccttg gggtacaccc aggccgacgt ggggctcacc    3900
ctgggcgttc tctttggaaa ggtgttcagc cagaccacca tctgtcgctt cgaggccttg    3960
cagctcagcc ttaagaacat gtgtaagctg cggcccctgc tggagaagtg ggtggaggaa    4020
gccgacaaca atgagaacct tcaggagata tgcaaatcgg agaccctggt gcaggcccgg    4080
aagagaaagc gaactagcat tgagaaccgt gtgaggtgga gtctggagac catgtttctg    4140
aagtgcccga agccctccct acagcagatc actcacatcg ccaatcagct gggctagag    4200 aaggatgtgg ttcgagtatg gttctgtaac cggcgccaga agggcaaaag atcaagtatt    4260
gagtattccc aacgagaaga gtatgaggct acagggacac ctttcccagg ggggctgta    4320 tcctttcctc tgcccccagg tccccacttt ggcaccccag gctatggaag cccccacttc    4380
accacactct actcagtccc ttttcctgag ggcgaggcct ttccctctgt tccgtcact    4440 gctctgggct ctcccatgca ttcaaacgga agtggcgtga acagacttt gaattttgac    4500 cttctcaagt tggcgggaga cgtggagtcc aacccagggc ccatggctgt cagcgacgct    4560
ctgctcccgt ccttctccac gttcgcgtcc ggcccggcgg aagggagaa gacactgcgt    4620 ccagcaggtg ccccgactaa ccgttggcgt gaggaactct ctcacatgaa gcgacttccc    4680
ccacttcccg ccgcccccta cgacctggcg gcgacggtgg ccacagacct ggagagtggc    4740
ggagctggtg cagcttgcag cagtaacaac ccggccctcc tagcccggag ggagaccgag    4800
gagttcaacg acctcctgga cctagacttt atcctttcca actcgctaac ccaccaggaa    4860
tcggtggccg ccaccgtgac cacctcggcg tcagcttcat cctcgtcttc cccagcgagc    4920
agcggccctg ccagcgcgcc ctccacctgc agcttcagct atccgatccg ggccgggggt    4980
gacccgggcg tggctgccag caacacaggt ggagggctcc tctacagccg agaatctgcg    5040
ccacctccca cggccccctt caacctggcg gacatcaatg acgtgagccc ctcgggcggc    5100
ttcgtggctg agctcctgcg gccggagttg gacccagtat acattccgcc acagcagcct    5160
cagccgccag gtggcgggct gatgggcaag tttgtgctga aggcgtctct gaccaccccct    5220 ggcagcgagt acagcagccc ttcggtcatc agtgttagca aaggaagccc agacggcagc    5280
caccccgtgg tagtggcgcc ctacagcggt ggcccgccgc gcatgtgccc caagattaag    5340
caagaggcgg tcccgtcctg cacggtcagc cggtccctag aggcccattt gagcgctgga    5400
ccccagctca gcaacggcca ccggcccaac acacacgact cccccctggg gcggcagctc    5460
cccaccagga ctacccctac actgagtccc gaggaactgc tgaacagcag ggactgtcac    5520
cctggcctgc ctcttccccc aggattccat ccccatccgg ggcccaacta ccctcctttc    5580
ctgccagacc agatgcagtc acaagtcccc tctctccatt atcaagagct catgccaccg    5640
ggttcctgcc tgccagagga gcccaagcca agagggaa gaaggtcgtg gccccggaaa    5700
agaacagcca cccacacttg tgactatgca ggctgtggca aaacctatac caagagttct    5760
catctcaagg cacacctgcg aactcacaca ggcgagaaac cttaccactg tgactgggac    5820
ggctgtgggt ggaaattcgc ccgctccgat gaactgacca ggcactaccg caaacacaca    5880
gggcaccggc cctttcagtg ccagaagtgt gacagggcct tttccaggtc ggaccacctt    5940
gccttacaca tgaagaggca cttttaaaga tccctccccc cccctaacg ttactggccg    6000 aagccgcttg gaataaggcc ggtgtgcgtt tgtctatatg ttattttcca ccatattgcc    6060
gtcttttggc aatgtgaggg cccggaaacc tggccctgtc ttcttgacga gcattcctag    6120
```

```
gggtctttcc cctctcgcca aaggaatgca aggtctgttg aatgtcgtga aggaagcagt    6180
tcctctggaa gcttcttgaa gacaaacaac gtctgtagcg acccttttgca ggcagcggaa   6240 ccccccacct ggcgacaggt gcctctgcgg ccaaaagcca cgtgtataag atacacctgc    6300
aaaggcggca aaccccagt gccacgttgt gagttggata gttgtggaaa gagtcaaatg     6360
gctctcctca agcgtattca caagggct gaaggatgcc cagaaggtac cccattgtat      6420
gggatctgat ctggggcctc ggtgcacatg ctttacatgt gtttagtcga ggttaaaaaa    6480
acgtctaggc cccccgaacc acggggacgt ggttttcctt tgaaaaacac gatgataata    6540
tggccacaca tatgatgtat aacatgatgg agacggagct gaagccgccg ggcccgcagc    6600
aagcttcggg gggcggcggc ggaggaggca acgccacggc ggcggcgacc ggcggcaacc    6660
agaagaacag cccggaccgc gtcaagaggc ccatgaacgc cttcatggta tggtcccggg    6720
ggcagcggcg taagatggcc caggagaacc ccaagatgca caactcggag atcagcaagc    6780
gcctgggcgc ggagtggaaa cttttgtccg agaccgagaa gcggccgttc atcgacgagg    6840
ccaagcggct gcgcgctctg cacatgaagg agcacccgga ttataaatac cggccgcggc    6900
ggaaaaccaa gacgctcatg aagaaggata agtacacgct tcccggaggc ttgctggccc    6960
ccggcgggaa cagcatggcg agcggggttg gggtgggcgc cggcctgggt gcgggcgtga    7020
accagcgcat ggacagctac gcgcacatga acggctggag caacggcagc tacagcatga    7080
tgcaggagca gctgggctac ccgcagcacc cgggcctcaa cgctcacggc gcggcacaga    7140
tgcaaccgat gcaccgctac gacgtcagcg ccctgcagta caactccatg accagctcgc    7200
agacctacat gaacggctcg cccacctaca gcatgtccta ctcgcagcag ggcaccccccg   7260 gtatggcgct gggctccatg ggctctgtgg tcaagtccga ggccagctcc agcccccccg    7320
tggttacctc ttcctcccac tcagggcgc cctgccaggc cggggacctc cgggacatga    7380
tcagcatgta cctccccggc gccgaggtgc cggagcccgc tgcgcccagt agactgcaca    7440
tggcccagca ctaccagagc ggcccggtgc ccggcacggc cattaacggc acactgcccc    7500
tgtcgcacat gggtagtggg caatgtacta actacgcttt gttgaaactc gctggcgatg    7560
ttgaaagtaa ccccggtcct atggtgagca agggcgagga gataacatg gccatcatca    7620 aggagttcat gcgcttcaag gtgcacatgg agggctccgt gaacggccac gagttcgaga    7680
tcgagggcga gggcgagggc cgcccctacg agggcaccca ccgccaag ctgaaggtga     7740 ccaagggtgg ccccctgccc ttcgcctggg acatcctgtc ccctcagttc atgtacggct    7800
ccaaggccta cgtgaagcac cccgccgaca tccccgacta cttgaagctg tccttccccg    7860
agggcttcaa gtgggagcgc gtgatgaact tcgaggacgg cggcgtggtg accgtgaccc    7920
aggactcctc cctgcaggac ggcgagttca tctacaaggt gaagctgcgc ggcaccaact    7980
tcccctccga cggccccgta atgcagaaga agaccatggg ctgggaggcc tcctccgagc    8040
ggatgtaccc cgaggacggc gccctgaagg gcgagatcaa gcagaggctg aagctgaagg    8100
acggcggcca ctacgacgct gaggtcaaga ccacctacaa ggccaagaag cccgtgcagc    8160
tgcccggcgc ctacaacgtc aacatcaagt tggacatcac ctcccacaac gaggactaca    8220
ccatcgtgga acagtacgaa cgcgccgagg gccgccactc caccggcggc atggacgagc    8280
tgtacaagta aatcgataga tcctaatcaa cctctggatt acaaaatttg tgaaagattg    8340
actggtattc ttaactatgt tgctcctttt acgctatgtg gatacgctgc tttaatgcct    8400
ttgtatcatg ctattgcttc ccgtatggct ttcattttct cctccttgta taaatcctgg    8460
ttgctgtctc tttatgagga gttgtggccc gttgtcaggc aacgtggcgt ggtgtgcact    8520
```

```
gtgtttgctg acgcaacccc cactggttgg ggcattgcca ccacctgtca gctccttccc    8580
gggactttcg ctttccccct ccctattgcc acggcggaac tcatcgccgc ctgccttgcc    8640
cgctgctgga caggggctcg gctgttgggc actgacaatt ccgtggtgtt gtcgggaaa     8700 tcatcgtcct ttccttggct gctcgcctgt gttgccacct ggattctgcg cgggacgtcc    8760
ttctgctacg tcccttcggc cctcaatcca gcggaccttc cttcccgcgg cctgctgccg    8820
gctctgcggc ctcttccgcg tcttcgcctt cgccctcaga cgagtcggat ctcccttggg    8880
gccgcctccc cgcctggtac ctttaagacc aatgacttac aaggcagctg tagatcttag    8940 ccactttta aaagaaaagg ggggactgga agggctaatt cactcccaac gaagacaaga    9000
tcacctgcag acaggcgcg caggtaccat aacttcgtat aatgtatgct atacgaagtt    9060
atggcgcgcc ctgcttttg cttgtactgg gtctctctgg ttagaccaga tctgagcctg     9120
ggagctctct ggctaactag gaacccact gcttaagcct caataaagct tgccttgagt     9180
gcttcaagta gtgtgtgccc gtctgttgtg tgactctggt aactagagat ccctcagacc    9240
cttttagtca gtgtggaaaa tctctagcac ccgggcgatt aaggaaaggg ctagatcatt    9300
cttgaagacg aaagggcctc gtgatacgcc tattttata ggttaatgtc atgataataa     9360
tggtttctta gacgtcaggt ggcacttttc ggggaaatgt gcgcggaacc cctatttgtt    9420
tattttctta aatacattca aatatgtatc cgctcatgag acaataaccc tgataaatgc    9480
ttcaataata ttgaaaaagg aagagtatga gtattcaaca tttccgtgtc gcccttattc    9540 cctttttgc ggcattttgc cttcctgttt ttgctcaccc agaaacgctg gtgaaagtaa     9600
aagatgctga agatcagttg ggtgcacgag tgggttacat cgaactggat ctcaacagcg    9660
gtaagatcct tgagagttttt cgccccgaag aacgttttcc aatgatgagc acttttaaag    9720
ttctgctatg tggcgcggta ttatcccgtg ttgacgccgg gcaagagcaa ctcggtcgcc    9780
gcatacacta ttctcagaat gacttggttg agtactcacc agtcacagaa aagcatctta    9840
cggatggcat gacagtaaga gaattatgca gtgctgccat aaccatgagt gataacactg    9900
cggccaactt acttctgaca acgatcggag gaccgaagga ctaaccgct tttttgcaca    9960 acatgggga tcatgtaact cgccttgatc gttgggaacc ggagctgaat gaagccatac    10020
caaacgacga gcgtgacacc acgatgcctg tagcaatggc aacaacgttg cgcaaactat    10080
taactggcga actacttact ctagcttccc ggcaacaatt aatagactgg atggaggcgg    10140
ataaagttgc aggaccactt ctgcgctcgg cccttccggc tggctggttt attgctgata    10200
aatctggagc cggtgagcgt gggtctcgcg gtatcattgc agcactgggg ccagatggta    10260
agccctcccg tatcgtagtt atctacacga cggggagtca ggcaactatg gatgaacgaa    10320
atagacagat cgctgagata ggtgcctcac tgattaagca ttggtaactg tcagaccaag    10380
tttactcata tactttag attgatttaa aacttcattt ttaatttaaa aggatctagg     10440
tgaagatcct ttttgataat ctcatgacca aaatccctta acgtgagttt tcgttccact    10500
gagcgtcaga ccccgtagaa aagatcaaag gatcttcttg agatcctttt tttctgcgcg    10560
taatctgctg cttgcaaaca aaaaaaccac cgctaccagc ggtggtttgt ttgccggatc    10620
aagagctacc aactctttt ccgaaggtaa ctggcttcag cagagcgcag ataccaaata    10680
ctgttcttct agtgtagccg tagttaggcc accacttcaa gaactctgta gcaccgccta    10740
catacctcgc tctgctaatc ctgttaccag tggctgctgc cagtggcgat aagtcgtgtc    10800
ttaccgggtt ggactcaaga cgatagttac cggataaggc gcagcggtcg gctgaacgg     10860
```

```
ggggttcgtg cacacagccc agcttggagc gaacgaccta caccgaactg agatacctac    10920
agcgtgagct atgagaaagc gccacgcttc ccgaagggag aaaggcggac aggtatccgg    10980
taagcggcag ggtcggaaca ggagagcgca cgagggagct tccaggggga aacgcctggt    11040
atctttatag tcctgtcggg tttcgccacc tctgacttga gcgtcgattt ttgtgatgct    11100 cgtcagggg gcggagccta tggaaaaacg ccagcaacgc ggcctttta cggttcctgg     11160 ccttttgctg gccttttgct cacatgttct ttcctgcgtt atccctgat tctgtggata    11220 accgtattac cgcctttgag tgagctgata ccgctcgccg cagccgaacg accgagcgca    11280
gcgagtcagt gagcgaggaa gcggaagagc gcccaatacg caaaccgcct ctccccgcgc    11340
gttggccgat tcattaatgc agcaagctca tggctgacta atttttttta tttatgcaga    11400
ggccgaggcc gcctcggcct ctgagctatt ccagaagtag tgaggaggct tttttggagg    11460
cctaggcttt tgcaaaaagc tccccgtggc acgacaggtt tcccgactgg aaagcgggca    11520
gtgagcgcaa cgcaattaat gtgagttagc tcactcatta ggcacccag gctttacact     11580 ttatgcttcc ggctcgtatg ttgtgtggaa ttgtgagcgg ataacaattt cacacaggaa    11640
acagctatga catgattacg aatttcacaa ataaagcatt ttttcactg cattctagtt    11700 gtggtttgtc caaactcatc aatgtatctt atcatgtctg gatcaactgg ataactcaag    11760
ctaaccaaaa tcatcccaaa cttcccaccc catacctat taccactgcc aattacctgt     11820
ggtttcattt actctaaacc tgtgattcct ctgaattatt ttcattttaa agaaattgta    11880
tttgttaaat atgtactaca aacttagtag t                                   11911
```

<210> SEQ ID NO 51
<211> LENGTH: 1983
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 51

```
atgtccaatt tactgaccgt acaccaaaat ttgcctgcat taccggtcga tgcaacgagt     60
gatgaggttc gcaagaacct gatggacatg ttcagggatc gccaggcgtt ttctgagcat    120
acctggaaaa tgcttctgtc cgtttgccgg tcgtgggcgg catggtgcaa gttgaataac    180
cggaaatggt ttcccgcaga acctgaagat gttcgcgatt atcttctata tcttcaggcg    240
cgcggtctgg cagtaaaaac tatccagcaa catttgggcc agctaaacat gcttcatcgt    300
cggtccgggc tgccacgacc aagtgacagc aatgctgttt cactggttat gcggcggatc    360 cgaaagaaa acgttgatgc cggtgaacgt gcaaaacagg ctctagcgtt cgaacgcact    420
gatttcgacc aggttcgttc actcatggaa aatagcgatc gctgccagga tatacgtaat    480
ctggcatttc tggggattgc ttataacacc ctgttacgta tagccgaaat tgccaggatc    540
agggttaaag atatctcacg tactgacggt gggagaatgt taatccatat tggcagaacg    600
aaaacgctgg ttagcaccgc aggtgtagag aaggcactta gcctgggggt aactaaactg    660
gtcgagcgat ggatttccgt ctctggtgta gctgatgatc gaataacta cctgttttgc    720 cgggtcagaa aaaatggtgt tgccgcgcca tctgccacca gccagctatc aactcgcgcc    780
ctggaaggga tttttgaagc aactcatcga ttgatttacg gcgctaagga tgactctggt    840
cagagatacc tggcctggtc tggacacagt gcccgtgtcg gagccgcgcg agatatggcc    900
cgcgctggag tttcaatacc ggagatcatg caagctggtg gctggaccaa tgtaaatatt    960
```

-continued

```
gtcatgaact atatccgtaa cctggatagt gaaacagggg caatggtgcg cctgctggaa    1020
gatggcgatc tcgagccatc tgctggagac atgagagctg ccaacctttg ccaagcccg     1080 ctcatgatca aacgctctaa gaagaacagc ctggccttgt ccctgacggc cgaccagatg    1140
gtcagtgcct tgttggatgc tgagcccccc atactctatt ccgagtatga tcctaccaga    1200
cccttcagtg aagcttcgat gatgggctta ctgaccaacc tggcagacag ggagctggtt    1260
cacatgatca actgggcgaa gagggtgcca ggctttgtgg atttgaccct ccatgatcag    1320
gtccaccttc tagaatgtgc ctggctagag atcctgatga ttggtctcgt ctggcgctcc    1380
atggagcacc cagtgaagct actgtttgct cctaacttgc tcttggacag gaaccaggga    1440
aaatgtgtag agggcatggt ggagatcttc gacatgctgc tggctacatc atctcggttc    1500
cgcatgatga atctgcaggg agaggagttt gtgtgcctca aatctattat tttgcttaat    1560
tctggagtgt acacatttct gtccagcacc ctgaagtctc tggaagagaa ggaccatatc    1620
caccgagtcc tggacaagat cacagacact ttgatccacc tgatggccaa ggcaggcctg    1680
accctgcagc agcagcacca gcggctggcc cagctcctcc tcatcctctc ccacatcagg    1740
cacatgagta caaaggcat ggagcatctg tacagcatga agtgcaagaa cgtggtgccc    1800
ctctatgacc tgctgctgga ggcggcggac gcccaccgcc tacatgcgcc cactagccgt    1860
ggaggggcat ccgtggagga gacggaccaa agccacttgg ccactgcggg ctctacttca    1920
tcgcattcct tgcaaaagta ttacatcacg ggggaggcag agggtttccc tgccacagct    1980
tga                                                                  1983
```

<210> SEQ ID NO 52
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (2)..(2)
<223> OTHER INFORMATION: /replace="Ile"
<220> FEATURE:
<221> NAME/KEY: misc_feature
<222> LOCATION: (2)..(2)
<223> OTHER INFORMATION: /note="Residue given in the sequence has no
      preference with respect to that in the annotation for said
      position"
<220> FEATURE:
<221> NAME/KEY: MOD_RES
<222> LOCATION: (4)..(4)
<223> OTHER INFORMATION: Any amino acid

<400> SEQUENCE: 52

Asp Val Glu Xaa Asn Pro Gly Pro
1               5

<210> SEQ ID NO 53
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 53
tgcgggcgga catggggaga tcc                                               23

```
<210> SEQ ID NO 54
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 54
ccttcttggt ccgcccgttc tta                                         23

<210> SEQ ID NO 55
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 55
cggttcatca tggtacagtc                                             20

<210> SEQ ID NO 56
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 56
tatgactcac ttccaggggg cact                                        24

<210> SEQ ID NO 57
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 57
actcgataca ctggcctagc                                             20

<210> SEQ ID NO 58
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 58
agcgaggcat ggagagagcg gagcag                                      26

<210> SEQ ID NO 59
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
```

```
                                Synthetic primer"

<400> SEQUENCE: 59
atgggccgcc atacgacgac gctcaact                                              28

<210> SEQ ID NO 60
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
        Synthetic primer"

<400> SEQUENCE: 60
gggcactgtt cagttcagcg gatc                                                  24

<210> SEQ ID NO 61
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
        Synthetic primer"

<400> SEQUENCE: 61
cactgctcac tggagggggc ttgc                                                  24

<210> SEQ ID NO 62
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
        Synthetic primer"

<400> SEQUENCE: 62
ctttgaggtc ctggtccatc acgtgaccat                                            30

<210> SEQ ID NO 63
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
        Synthetic primer"

<400> SEQUENCE: 63
agttgtttgc tgcggagttg tcatctcgtc                                            30
```

What is claimed:

1. A lentiviral vector particle wherein the vector particle comprises a nucleic acid sequence comprising a sequence encoding:
   a. a first gene;
   b. a second gene;
   c. a third gene;
   d. fourth gene,
   wherein the four genes are Oct4, Sox2, Klf4 and cMyc, or Oct4, Sox2, Lin28, and Nanog;
   e. a first 'self-cleaving' 2A peptide;
   f. second 'self-cleaving' 2A peptide; and
   g. an internal ribosome entry site (IRES);

wherein the first 2A 'self-cleaving' peptide is positioned between at least the first and second genes and the second 'self-cleaving' 2A peptide is positioned between the third and fourth genes, wherein the first 2A 'self-cleaving' peptide and second 'self-cleaving' 2A peptide are different, wherein the nucleic acid sequence is operably linked to a promoter, wherein the IRES is between the second and third genes, and wherein the sequences encoding the first, second, third and fourth genes, first and second 'self-cleaving' 2A peptides, and the IRES are transcribed from the promoter as a multi-cistronic RNA.

2. The lentiviral vector particle of claim 1 further comprising a marker gene, wherein the marker gene encodes an optically visible protein or an enzyme.

3. The lentiviral vector particle of claim 1, wherein the first 'self-2A peptide is selected from the group consisting of F2A, E2A, T2A and P2A.

4. The lentiviral vector particle of claim 3, wherein the second 'self-cleaving' 2A peptide is selected from the group consisting of F2A, E2A, T2A and P2A.

5. The lentiviral vector particle of claim 4, wherein the second 'self-cleaving' 2A peptide is different from the first 'self-cleaving' 2A peptide.

6. The lentiviral vector particle of claim 1, wherein the order of the first, second, third and fourth genes is Oct4, Klf4, Sox2 and c-Myc.

7. The lentiviral vector particle of claim 1 further comprises a Cre-LoxP excision sequence.

* * * * *